United States Patent
Balan et al.

(10) Patent No.: US 10,577,352 B2
(45) Date of Patent: Mar. 3, 2020

(54) COT MODULATORS AND METHODS OF USE THEREOF

(71) Applicant: Gilead Sciences, Inc., Foster City, CA (US)

(72) Inventors: Gayatri Balan, Bellevue, WA (US); Chienhung Chou, Dublin, CA (US); Musong Kim, Bellevue, WA (US); Thorsten A. Kirschberg, San Carlos, CA (US); John O. Link, San Francisco, CA (US); Gary Phillips, Issaquah, WA (US); Roland D. Saito, San Mateo, CA (US); Neil H. Squires, San Francisco, CA (US); James G. Taylor, Burlingame, CA (US); William J. Watkins, Saratoga, CA (US); Nathan E. Wright, Foster City, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 16/045,518

(22) Filed: Jul. 25, 2018

(65) Prior Publication Data

US 2019/0016705 A1 Jan. 17, 2019

Related U.S. Application Data

(63) Continuation of application No. 15/634,314, filed on Jun. 27, 2017, now Pat. No. 10,059,695.

(60) Provisional application No. 62/356,926, filed on Jun. 30, 2016.

(51) Int. Cl.
*C07D 401/14* (2006.01)
*C07D 403/12* (2006.01)
*C07D 405/14* (2006.01)
*C07D 417/14* (2006.01)

(52) U.S. Cl.
CPC ......... *C07D 403/12* (2013.01); *C07D 401/14* (2013.01); *C07D 405/14* (2013.01); *C07D 417/14* (2013.01)

(58) Field of Classification Search
CPC .................................................. C07D 403/12
See application file for complete search history.

(56) References Cited

U.S. PATENT DOCUMENTS

| 7,297,795 | B2 | 11/2007 | Sutherland et al. |
| 7,432,279 | B2 | 10/2008 | Green et al. |
| 8,008,481 | B2 | 8/2011 | Ericsson et al. |
| 9,815,818 | B2 | 11/2017 | Bacon et al. |
| 9,878,995 | B2 | 1/2018 | Bacon et al. |
| 10,059,695 | B2 | 8/2018 | Balan et al. |
| 2005/0043537 | A1 | 2/2005 | Sutherland et al. |
| 2006/0264460 | A1 | 11/2006 | Green et al. |
| 2015/0297573 | A1 | 10/2015 | Dalle et al. |
| 2017/0268069 | A1 | 9/2017 | Garraway et al. |
| 2017/0362201 | A1 | 12/2017 | Bacon et al. |
| 2018/0237455 | A1 | 8/2018 | Bacon et al. |
| 2019/0016705 | A1 | 1/2019 | Balan et al. |

FOREIGN PATENT DOCUMENTS

| WO | WO-1998/43960 A1 | 10/1998 |
| WO | WO-2005/019201 A2 | 3/2005 |
| WO | WO-2006/124692 A2 | 11/2006 |
| WO | WO-2017/007689 A1 | 1/2017 |
| WO | WO-2017/007694 A1 | 1/2017 |
| WO | WO-2018/005435 A1 | 1/2018 |

OTHER PUBLICATIONS

Chemical Abstract Registry No. 1349435-18-2, indexed in the Registry File on STN CAS Online Dec. 6, 2011.
Cohen, (2009), "Targeting protein kinases for the development of anti-inflammatory drugs", Curr Opin Cell Biol., 21:317-24.
Cusack, K. et al. (2009) "Identification of a selective thieno[2,3-c]pyridine inhibitor of COT kinase and TNF-α production" *Bioorganic & Medicinal Chemistry Letters* 19:1722-25.
Detz, R. et al. (2008) "Enantioselective Copper-Catalyzed Propargylic Amination" *Angew. Chem. Int. Ed.* 47:3777-80.
Eisenberg, (2009), "Why can't we find a new treatment for SLE?", J Autoimmun, 32:223-30.
European Search Report dated Feb. 5, 2019 for EP App. No. 18186568.4, 12pgs.
Gantke, T. et al. (2010) "Regulation and function of TPL-2, an IkB kinase-regulated MAP kinase kinase kinase" Cell Res. 21(1):131-45.
Gantke, T. et al. (2011) "Regulation and function of TPL-2, an IkB kinase-regulated MAP kinase kinase kinase" Cell Res. 21:131-45.
Garofalo, A. et al.(2013) "Discovery of 4-alkylamino-7-aryl-3-cyanoquinoline LRRK2 kinase inhibitors" Bioorganic & Medicianl Chemistry Letters 23:1974-1977.
Gavrin et al. (2005) "Inhibition of Tpl2 kinase and TNF-α production with 1,7-naphthyridine-3-carbonitriles: Synthesis and structure-activity relationships" Bioorganic & Medicinal Chemistry Letters 15:5288-5292.
George, D. et al. (2008) "Discovery of thieno[2,3-c]pyridines as potent COT inhibitors" Bioorganic & Medicinal Chemistry Letters 18:4952-4955.
George, D. et al. (2009) "Cot/Tpl-2 Protein Kinase as a Target for the Treatment of Inflammatory Disease" Current Topics in Medicinal Chemistry 9:611-622.
Gianatassio, R. et al. (2016) "Strain Release Amination" Science 351(6270):241-246.
Glatthar, R. et al. (2016) "Discovery of Imidazoquinolines as a Novel Class of Potent, Selective, and in Vivo Efficacious Cancer Osaka Thyroid (COT) Kinase Inhibitors" Journal of Medicinal Chemistry 59:7544-7560.
Goyal, et al., (2011), "Models for anti-inflammatory activity of 8-substituted-4-anilino-6-aminoquinoline-3-carbonitriles", Med Chem Res, 21:1044-55.
Green, N. et al. (2007) "Inhibitors of Tumor Progression Loci-2 (Tpl2) Kinase and Tumor Necrosis Factor α (TNF-α) Production: Selectivity and in Vivo Antiinflammatory Activity of Novel 8-Substituted-4-anilino-6-aminoquinoline-3-carbonitriles" J. Med. Chem. 50:4728-4745.

(Continued)

*Primary Examiner* — Paul V Ward

(57) ABSTRACT

The present disclosure relates generally to modulators of Cot (cancer Osaka thyroid) and methods of use and manufacture thereof.

20 Claims, No Drawings

(56) References Cited

OTHER PUBLICATIONS

Hall, J. Perry et al. (2007) "Pharmacologic Inhibition of Tpl2 Blocks Inflammatory Responses in Primary Human Monocytes, Synoviocytes, and Blood" The Journal of Biological Chemistry 282:46:33295-33304.

Hirata, K. et al. (2010) Inhibition of tumor progression locus 2 protein kinase decreases lipopolysaccharide-induced tumor necrosis factor alpha production due to the inhibition of the tip-associated protein induction in RAW264.7 cells, Biol Pharm Bull 33(7):1233-7.

Hu et al. (2006) "Inhibition of Tpl2 kinase and TNFa production with quinoline-3-carbonitriles for the treatment of rheumatoid arthritis" Bioorganic & Medicinal Chemistry Letters 16:6067-6072.

Hu, Y. et al. (2011) "Discovery of indazoles as inhibitors of Tpl2 kinase" Bioorganic & Medicinal Chemistry Letters 1-4 (article in press; doi: 10.1016).

Int'l Search Report—Written Opinion dated Sep. 20, 2017 for PCT/US2017/039418.

Int'l Search Report—Written Opinion dated Aug. 16, 2016 for PCT Apppl. No. PCT/US2016/040520.

Int'l Search Report—Written Opinion dated Sep. 23, 2016 for PCT/US2016/040552.

Kaila, N. et al. (2007) "Identification of a novel class of selective Tpl2 kinase inhibitors: 4-Alkylamino-[1,7]naphthyridine-3-carbonitriles" Bioorganic & Medicinal Chemistry 15:6425-6442.

Kitamura, M. et al. (2014) "A reagent for safe and efficient diazo-transfer to primary amines: 2-azido-1,3-dimethylimidazolinium hexafluorophosphate" Org. Biomol. Chem. 12:4397-4406.

Notice of Allowance dated Oct. 25, 2017 for U.S. Appl. No. 15/429,086.

Notice of Allowance dated Jun. 19, 2017 for U.S. Appl. No. 15/199,779.

Notice of Allowance dated Apr. 26, 2018 for U.S. Appl. No. 15/634,314, (5 pages).

Office Action dated Jun. 30, 2017 for U.S. Appl. No. 15/429,086.
Office Action dated Mar. 23, 2017 for U.S. Appl. No. 15/429,086.
Office Action dated Sep. 7, 2017 for U.S. Appl. No. 15/199,534.
Office Action dated Dec. 18, 2017 for U.S. Appl. No. 15/634,314, (13 Pages).
Office Action dated Jul. 5, 2018 for U.S. Appl. No. 15/697,755, (62 pages).
Office action dated Oct. 18, 2017, for Taiwan App. No. 105121281. English translation only. 3pgs.
Restriction Requirement dated Feb. 16, 2017 for U.S. Appl. No. 15/199,534.
Restriction Requirement dated Mar. 8, 2017 for U.S. Appl. No. 15/199,779.
Restriction Requirement dated Jun. 29, 2018 for U.S. Appl. No. 15/891,163, 12pgs.
Restriction Requirement dated Mar. 26, 2018 for U.S. Appl. No. 15/697,755.
Restriction Requirement dated Feb. 8, 2019 for U.S. Appl. No. 16/045,518, 5pgs.
Restriction Requirement dated Aug. 11, 2017 for U.S. Appl. No. 15/634,314, (6 pages).

Teli, M. et al. (2011) "Pharmacophore generation and atom-based 3D-QSAR of novel quinoline-3-carbonitrile derivatives as Tpl2 kinase inhibitors" *Journal of Enzyme Inhibition and Medicinal Chemistry*, 1-13.

Wissner, A. et al. (2004) "Syntheses and EGFR kinase inhibitory activity of 6-substituted-4-anilino [1,7] and [1,8] naphthyridine-3-carbonitriles" *Bioorg Med Checm Lett*. 14(6):1411-6.

Wu, J. et al. (2009) "Selective inhibitors of tumor progression loci-2 (Tpl2) kinase with potent inhibition of TNF-$\alpha$ production in human whole blood" Bioorganic & Medicinal Chemistry Letters 19:3485-3488.

Zhu, et al., (2010), "Anti-TNF-alpha therapies in systemic lupus erythematosus", J Biomed Biotechnol., Article ID: 465898, 8pgs.

McMahon, (2000), "VEGF receptor signaling in tumor angiogenesis", Oncologist, 1:3-10.

Pinedo, et al., (2000), "Translational Research: The Role of VEGF in Tumor Angiogenesis", Department of Medical Oncology, 2pp.

Written Opinion and International Search Report for PCT/US2017/039418 dated Sep. 20, 2017.

Wu et al., (2009), "Selective inhibitors of tumor progression loci-2 (Tpl2) kinase with potent inhibition of TNF-alpha production in human whole blood", Bioorg Med Chem Lett., 19:3485-8.

COT MODULATORS AND METHODS OF USE THEREOF

CROSS-REFERENCE TO RELATED APPLICATIONS

This Application is a Continuation of application Ser. No. 15/634,314 filed on Jun. 27, 2017. Application Ser. No. 15/634,314 claims the benefit of U.S. Provisional Application 62/356,926 filed on Jun. 30, 2016. The entire contents of these applications are incorporated herein by reference in their entirety.

FIELD

The present disclosure relates generally to modulators of Cot (cancer Osaka thyroid) and methods of use and manufacture thereof.

BACKGROUND

Cot (cancer Osaka thyroid) protein is a serine/threonine kinase that is a member of the MAP kinase kinase kinase (MAP3K) family. It is also known as "Tpl2" (tumor progression locus), "MAP3K8" (mitogen-activated protein kinase kinase kinase 8) or "EST" (Ewing sarcoma transformant). Cot was identified by its oncogenic transforming activity in cells and has been shown to regulate oncogenic and inflammatory pathways.

Cot is known to be upstream in the MEK-ERK pathway and is essential for LPS induced tumor necrosis factor-α (TNF-α) production. Cot has been shown to be involved in both production and signaling of TNFα. TNFα is a pro-inflammatory cytokine and plays an important role in inflammatory diseases, such as rheumatoid arthritis (RA), multiple sclerosis (MS), inflammatory bowel disease (IBD), diabetes, sepsis, psoriasis, misregulated TNFα expression and graft rejection.

Agents and methods that modulate the expression or activity of Cot, therefore, may be useful for preventing or treating such diseases.

SUMMARY

The present disclosure provides compounds that modulate the expression or activity of Cot. The disclosure also provides compositions, including pharmaceutical compositions, kits that include the compounds, and methods of using (or administering) and making the compounds. The compounds provided herein are useful in treating diseases, disorders, or conditions that are mediated by Cot. The disclosure also provides compounds for use in therapy. The disclosure further provides compounds for use in a method of treating a disease, disorder, or condition that is mediated by Cot. Moreover, the disclosure provides uses of the compounds in the manufacture of a medicament for the treatment of a disease, disorder or condition that is mediated by (or mediated, at least in part, by) Cot.

In one aspect, provided is a compound having the structure of Formula I:

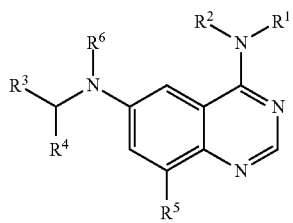

wherein
$R^1$ is $C_{1-9}$ alkyl, $C_{3-15}$ cycloalkyl, heterocyclyl, heteroaryl, or $C_{6-10}$ aryl; wherein each $C_{1-9}$ alkyl, $C_{3-15}$ cycloalkyl, heterocyclyl, heteroaryl, and $C_{6-10}$ aryl may be optionally substituted with one to four $Z^1$;
$R^2$ is hydrogen, —C(O)—$R^7$, —C(O)O—$R^7$, —C(O)N$(R^7)_2$, or $C_{1-9}$ alkyl;
$R^3$ is heterocyclyl or heteroaryl;
  wherein each heterocyclyl or heteroaryl is optionally substituted with one to four $Z^3$;
$R^4$ is aryl, heterocyclyl, or heteroaryl;
  wherein each aryl, heterocyclyl, or heteroaryl is optionally substituted with one to four $Z^4$;
$R^5$ is hydrogen, halo, cyano, —$NO_2$, —O—$R^7$, —N($R^8$)($R^9$), —S(O)—$R^7$, —S(O)$_2R^7$, —S(O)$_2$N($R^7$)$_2$, —C(O)$R^7$, —OC(O)—$R^7$, —C(O)O—$R^7$, —OC(O)O—$R^7$, —OC(O)N($R^{10}$)($R^{11}$), —C(O)N($R^7$)$_2$, —N($R^7$)C(O)($R^7$), $C_{1-9}$ alkyl, $C_{2-6}$ alkenyl, $C_{2-6}$ alkynyl, $C_{1-9}$ alkylthio, $C_{1-6}$ haloalkyl, $C_{3-15}$ cycloalkyl, aryl, heterocyclyl, or heteroaryl;
  wherein each $C_{1-9}$ alkyl, $C_{2-6}$ alkenyl, $C_{2-6}$ alkynyl, $C_{1-9}$ alkylthio, $C_{1-6}$ haloalkyl, $C_{3-15}$ cycloalkyl, aryl, heterocyclyl, and heteroaryl may be optionally substituted with one to four $Z^5$;
$R^6$ is hydrogen, —C(O)—$R^7$, —C(O)O—$R^7$, —C(O)N$(R^7)_2$, $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl;
  wherein each $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, and heteroaryl may be optionally substituted with one to four $Z^6$;
each $R^7$ is independently hydrogen, $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl;
  wherein each $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, and heteroaryl may be optionally substituted with one to four $Z^7$;
$R^8$ and $R^9$ at each occurrence are independently hydrogen, —S(O)$_2R^{10}$, —C(O)—$R^{10}$, —C(O)O—$R^{10}$, —C(O)N$(R^{10})(R^{11})$, $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl;
  wherein each $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl may be optionally substituted with one to four $Z^8$;
$R^{10}$ and $R^{11}$ at each occurrence are independently hydrogen, $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl,
  wherein each $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, and heteroaryl optionally is substituted with one to four $Z^b$;
each $Z^1$, $Z^3$, $Z^4$, $Z^5$, $Z^6$, $Z^7$ and $Z^8$ is independently hydrogen, oxo, halo, —$NO_2$, —$N_3$, cyano, thioxo, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O—$R^{12}$, —C(O)—$R^{12}$, —C(O)O—$R^{12}$, —C(O)—N($R^{13}$)($R^{14}$), —N($R^{13}$)($R^{14}$), —N($R^{13}$)$_2$($R^{14}$)$^+$, —N($R^{12}$)C(O)—$R^{12}$, —N($R^{12}$)C(O)O—$R^{12}$, —N($R^{12}$)C(O)N($R^{13}$)($R^{14}$), —N($R^{12}$)S(O)$_2$($R^{12}$), —N$R^{12}$S(O)$_2$N($R^{13}$)($R^{14}$), —N$R^{12}$S(O)$_2$O($R^{12}$), —OC(O)$R^{12}$, —OC(O)—N($R^{13}$)($R^{14}$), —P(O)(O$R^{12}$)$_2$, OP(O)(O$R^{12}$)$_2$, —CH$_2$P(O)(O$R^{12}$)$_2$, —OCH$_2$P(O)(O$R^{12}$)$_2$, —C(O)OCH$_2$P(O)(O$R^{12}$)$_2$, —P(O)($R^{12}$)(O$R^{12}$), —OP(O)($R^{12}$)(O$R^{12}$), —CH$_2$P(O)($R^{12}$)(O$R^{12}$), —OCH$_2$P(O)($R^{12}$)(O$R^{12}$). —C(O)OCH$_2$P(O)($R^{12}$)(O$R^{12}$), —P(O)(N($R^{12}$)$_2$)$_2$, —OP(O)(N($R^{12}$)$_2$)$_2$, —CH$_2$P(O)(N($R^{12}$)$_2$)$_2$, —OCH$_2$P(O)(N($R^{12}$)$_2$)$_2$, —C(O)OCH$_2$P(O)(N($R^{12}$)$_2$)$_2$. —P(O)(N($R^{12}$)$_2$)(O$R^{12}$), —OP(O)(N($R^{12}$)$_2$)(O$R^{12}$), —CH$_2$P(O)(N($R^{12}$)$_2$)(O$R^{12}$), —OCH$_2$P(O)(N($R^{12}$)$_2$)(O$R^{12}$), —C(O)OCH$_2$P(O)(N($R^{12}$)$_2$)(O$R^{12}$), —P(O)($R^{12}$)(N($R^{12}$)$_2$), —OP(O)($R^{12}$)(N($R^{12}$)$_2$), —CH$_2$P(O)($R^{12}$)(N($R^{12}$)$_2$), —OCH$_2$P(O)($R^{12}$)(N($R^{12}$)$_2$), —C(O)OCH$_2$P(O)($R^{12}$)N($R^{12}$)$_2$), —Si($R^{12}$)$_3$, —S—$R^{12}$, —S(O)$R^{12}$, —S(O)(NH)$R^{12}$, —S(O)$_2$$R^{12}$ or —S(O)$_2$N($R^{13}$)($R^{14}$);

wherein any alkyl, alkenyl, alkynyl, cycloalkyl, haloalkyl, aryl, heteroaryl or heterocyclyl is optionally substituted with one to four $Z^{1a}$ groups;

each $Z^{1a}$ is independently oxo, halo, thioxo, —NO$_2$, cyano, —N$_3$, $C_{1-9}$ alkyl, $C_{2-6}$ alkenyl, $C_{2-6}$ alkynyl, $C_{3-15}$ cycloalkyl, $C_{1-8}$ haloalkyl, $C_{1-8}$ hydroxyalkyl, aryl, heteroaryl, heterocyclyl, —O—$R^{12}$, —C(O)$R^{12}$, —C(O)O—$R^{12}$, —C(O)N($R^{13}$)($R^{14}$), —N($R^{13}$)($R^{14}$), —N($R^{13}$)$_2$($R^{14}$)$^+$, —N($R^{12}$)—C(O)$R^{12}$, —N($R^{12}$)C(O)O($R^{12}$), —N($R^{12}$)C(O)N($R^3$)($R^{14}$), —N($R^{12}$)S(O)$_2$($R^{12}$), —N($R^{12}$)S(O)$_2$—N($R^{13}$)($R^{14}$), —N($R^{12}$)S(O)$_2$O($R^{12}$), —OC(O)$R^{12}$, —OC(O)O$R^{12}$, —OC(O)—N($R^{13}$)($R^{14}$), —C(O)N($R^{12}$)—S(O)$_2$$R^{12}$, —Si($R^{12}$)$_3$, —S—$R^{12}$, —S(O)$R^{12}$, —S(O)(NH)$R^{12}$, —S(O)$_2$$R^{12}$ or —S(O)$_2$N($R^{13}$)($R^{14}$);

wherein any alkenyl, alkynyl, cycloalkyl, aryl, heteroaryl or heterocyclyl is optionally substituted with one to four $Z^{1b}$ groups;

each $R^{12}$ is independently hydrogen, $C_{1-9}$ alkyl, $C_{2-6}$ alkenyl, $C_{2-6}$ alkynyl, $C_{3-15}$ cycloalkyl, aryl, heteroaryl or heterocyclyl, wherein any alkyl, alkenyl, alkynyl, cycloalkyl, aryl, heteroaryl or heterocyclyl is optionally substituted with one to four $Z^{1b}$ groups;

$R^{13}$ and $R^{14}$ at each occurrence are each independently hydrogen, $C_{1-9}$ alkyl, $C_{2-6}$ alkenyl, $C_{2-6}$ alkynyl, $C_{3-15}$ cycloalkyl, aryl, heteroaryl or heterocyclyl;

wherein any alkyl, alkenyl, alkynyl, cycloalkyl, aryl, heteroaryl or heterocyclyl is optionally substituted with one to four $Z^{1b}$ groups, or $R^{13}$ and $R^{14}$ together with the nitrogen to which they are attached form a heterocyclyl, wherein said heterocyclyl is optionally substituted with one to four $Z^{1b}$ groups;

each $Z^{1b}$ is independently oxo, thioxo, hydroxy, halo, —NO$_2$, —N$_3$, cyano, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O($C_{1-9}$ alkyl), —O($C_{2-6}$ alkenyl), —O($C_{2-6}$ alkynyl), —O($C_{3-15}$ cycloalkyl), —O($C_{1-8}$ haloalkyl), —O(aryl), —O(heteroaryl), —O(heterocyclyl), —NH$_2$, —NH($C_{1-9}$ alkyl), —NH($C_{2-6}$ alkenyl), —NH($C_{2-6}$ alkynyl), —NH($C_{3-15}$ cycloalkyl), —NH($C_{1-8}$ haloalkyl), —NH(aryl), —NH(heteroaryl), —NH(heterocyclyl), —N($C_{1-9}$ alkyl)$_2$, —N($C_{3-15}$ cycloalkyl)$_2$, —N($C_{2-6}$ alkenyl)$_2$, —N($C_{2-6}$ alkynyl)$_2$, —N($C_{3-15}$ cycloalkyl)$_2$, —N($C_{1-4}$ haloalkyl)$_2$, —N(aryl)$_2$, —N(heteroaryl)$_2$, —N(heterocyclyl)$_2$, —N($C_{1-9}$ alkyl)($C_{3-15}$ cycloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)($C_{1-8}$ haloalkyl), —N($C_{1-9}$ alkyl)(aryl), —N($C_{1-9}$ alkyl)(heteroaryl), —N($C_{1-9}$ alkyl)(heterocyclyl), —C(O)($C_{1-9}$ alkyl), —C(O)($C_{2-6}$ alkenyl), —C(O)($C_2$ alkynyl), —C(O)($C_{3-15}$ cycloalkyl), —C(O)($C_{1-8}$ haloalkyl), —C(O)(aryl), —C(O)(heteroaryl), —C(O)(heterocyclyl), —C(O)O$C_{1-9}$ alkyl), —C(O)O($C_{2-6}$ alkenyl), —C(O)O($C_{2-6}$ alkynyl), —C(O)O($C_{3-15}$ cycloalkyl), —C(O)O($C_{1-8}$ haloalkyl), —C(O)O(aryl), —C(O)O(heteroaryl), —C(O)O(heterocyclyl), —C(O)NH$_2$, —C(O)NH($C_{1-9}$ alkyl), —C(O)NH($C_{2-6}$ alkenyl), —C(O)NH($C_{2-6}$ alkynyl), —C(O)NH($C_{3-15}$ cycloalkyl), —C(O)NH($C_{1-8}$ haloalkyl), —C(O)NH(aryl), —C(O)NH(heteroaryl), —C(O)NH(heterocyclyl), —C(O)N($C_{1-9}$ alkyl)$_2$, —C(O)N($C_{3-15}$ cycloalkyl)$_2$, —C(O)N($C_{2-6}$ alkenyl)$_2$, —C(O)N($C_{2-6}$ alkynyl)$_2$, —C(O)N($C_{3-15}$ cycloalkyl)$_2$, —C(O)N($C_{1-8}$ haloalkyl)$_2$, —C(O)N(aryl)$_2$, —C(O)N(heteroaryl)$_2$, —C(O)N(heterocyclyl)$_2$, —NHC(O)($C_{1-9}$ alkyl), —NHC(O)($C_{2-6}$ alkenyl), —NHC(O)($C_{2-6}$ alkynyl), —NHC(O)($C_{3-15}$ cycloalkyl), —NHC(O)($C_{1-4}$ haloalkyl), —NHC(O)(aryl), —NHC(O)(heteroaryl), —NHC(O)(heterocyclyl), —NHC(O)O($C_{1-9}$ alkyl), —NHC(O)O($C_{2-6}$ alkenyl), —NHC(O)O($C_{2-6}$ alkynyl), —NHC(O)O($C_{3-15}$ cycloalkyl), —NHC(O)O($C_{1-8}$ haloalkyl), —NHC(O)O(aryl), —NHC(O)O(heteroaryl), —NHC(O)O(heterocyclyl), —NHC(O)NH($C_{1-9}$ alkyl), —NHC(O)NH($C_{2-6}$ alkenyl), —NHC(O)NH($C_{2-6}$ alkynyl), —NHC(O)NH($C_{3-15}$ cycloalkyl), —NHC(O)NH($C_{1-8}$ haloalkyl), —NHC(O)NH(aryl), —NHC(O)NH(heteroaryl), —NHC(O)NH(heterocyclyl), —SH, —S($C_{1-9}$ alkyl), —S($C_{2-6}$ alkenyl), —S($C_{2-6}$ alkynyl), —S($C_{3-15}$ cycloalkyl), —S($C_{1-8}$ haloalkyl), —S(aryl), —S(heteroaryl), —S(heterocyclyl), —NHS(O)($C_{1-9}$ alkyl), —N($C_{1-9}$ alkyl)(S(O)($C_{1-9}$ alkyl), —S(O)N($C_{1-9}$ alkyl)$_2$, S(O)($C_{1-9}$ alkyl), —S(O)(NH)($C_{1-9}$ alkyl), —S(O)($C_{2-6}$ alkenyl), —S(O)($C_{2-6}$ alkynyl), —S(O)($C_{3-15}$ cycloalkyl), —S(O)($C_{1-8}$ haloalkyl), —S(O)(aryl), —S(O)(heteroaryl), —S(O)(heterocyclyl), —S(O)$_2$($C_{1-9}$ alkyl), —S(O)$_2$($C_{2-6}$ alkenyl), —S(O)$_2$($C_{2-6}$ alkynyl), —S(O)$_2$($C_{3-15}$ cycloalkyl), —S(O)$_2$($C_{1-8}$ haloalkyl), —S(O)$_2$(aryl), —S(O)$_2$(heteroaryl), —S(O)$_2$(heterocyclyl), —S(O)$_2$NH($C_{1-9}$ alkyl), or —S(O)$_2$N($C_{1-9}$ alkyl)$_2$;

wherein any alkyl, cycloalkyl, aryl, heteroaryl, or heterocyclyl is optionally substituted with one to four halo, $C_{1-9}$ alkyl, $C_{1-8}$ haloalkyl, —OH, —NH$_2$, —NH($C_{1-9}$ alkyl), —NH($C_{3-15}$ cycloalkyl), —NH($C_{1-8}$ haloalkyl), —NH(aryl), —NH(heteroaryl), —NH(heterocyclyl), —N($C_{1-9}$ alkyl)$_2$, —N($C_{3-15}$ cycloalkyl)$_2$, —NHC(O)($C_{3-15}$ cycloalkyl), —NHC(O)($C_{1-8}$ haloalkyl), —NHC(O)(aryl), —NHC(O)(heteroaryl), —NHC(O)(heterocyclyl), —NHC(O)O($C_{1-9}$ alkyl), —NHC(O)O($C_{2-4}$ alkynyl), —NHC(O)O($C_{3-15}$ cycloalkyl), —NHC(O)O($C_{1-8}$ haloalkyl), —NHC(O)O(aryl), —NHC(O)O(heteroaryl), —NHC(O)O(heterocyclyl), —NHC(O)NH($C_{1-9}$ alkyl), —S(O)(NH)($C_{1-9}$ alkyl), S(O)$_2$($C_{1-9}$ alkyl), —S(O)$_2$($C_{3-15}$ cycloalkyl), —S(O)$_2$($C_{1-8}$ haloalkyl), —S(O)$_2$(aryl), —S(O)$_2$(heteroaryl), —S(O)$_2$(heterocyclyl), —S(O)$_2$NH($C_{1-9}$ alkyl), —S(O)$_2$N($C_{1-9}$ alkyl)$_2$, —O($C_{3-15}$ cycloalkyl), —O($C_{1-8}$ haloalkyl), —O(aryl), —O(heteroaryl), —O(heterocyclyl), or —O($C_{1-9}$ alkyl);

m is 0, 1, or 2;

or a pharmaceutically acceptable salt, stereoisomer, mixture of stereoisomers, or deuterated analog thereof.

In one aspect, provided is a compound having the structure of Formula I:

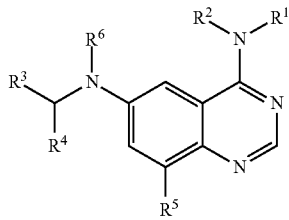

I wherein $R^1$ is $C_{1-9}$ alkyl or $C_{3-15}$ cycloalkyl; each $C_{1-9}$ alkyl and $C_{3-15}$ cycloalkyl may be optionally substituted with one to four $Z^1$; and wherein $Z^1$, $R^2$, $R^3$, $R^4$, $R^5$ and $R^6$ are as defined herein.

In certain aspects, provided are compounds of Formula II:

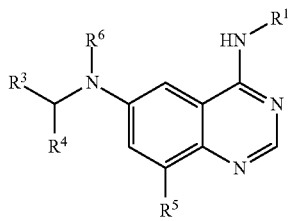

II wherein $R^1$, $R^3$, $R^4$, $R^5$ and $R^6$ are as defined herein.

In another aspect, provided are compounds of Formula IIA:

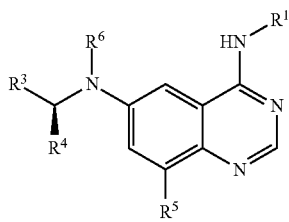

IIA wherein $R^1$, $R^3$, $R^4$, $R^5$ and $R^6$ are as defined herein.

In yet another aspect, provided are compounds of Formula IIIA:

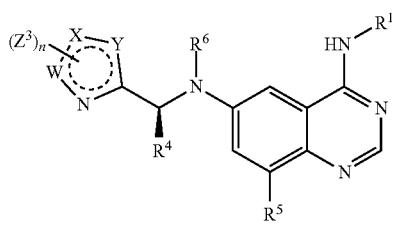

IIIA wherein $R^1$, $R^4$, $R^5$ and $R^6$ are as defined herein,
W, X and Y are each independently N or C;
n is 1, 2, or 3;
each $Z^3$ is independently hydrogen, oxo, halo, —$NO_2$, —$N_3$, cyano, thioxo, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O—$R^{12}$, —C(O)—$R^{12}$, —C(O)O—$R^{12}$, —C(O)—N($R^{13}$)($R^{14}$), —N($R^{13}$)($R^{14}$), —N($R^{13}$)$_2$($R^{14}$)$^+$, —N($R^{12}$)C(O)—$R^{12}$, —N($R^{12}$)C(O)O—$R^{12}$, —N($R^{12}$)C(O)N($R^{13}$)($R^{14}$), —N($R^{12}$)S(O)$_2$($R^{12}$), —N$R^{12}$S(O)$_2$N($R^{13}$)($R^{14}$), —N$R^{12}$S(O)$_2$O($R^{12}$), —OC(O)$R^{12}$, —OC(O)—N($R^{13}$)($R^{14}$), —P(O)($OR^{12}$)$_2$, —OP(O)($OR^{12}$)$_2$, —$CH_2$P(O)($OR^{12}$)$_2$, —$OCH_2$P(O)($OR^{12}$)$_2$, —C(O)$OCH_2$P(O)($OR^{12}$)$_2$, —P(O)($R^{12}$)($OR^{12}$), —OP(O)($R^{12}$)($OR^{12}$), —$CH_2$P(O)($R^{12}$)($OR^{12}$), —$OCH_2$P(O)($R^{12}$)($OR^{12}$), —C(O)$OCH_2$P(O)($R^{12}$)($OR^{12}$), —P(O)(N($R^{12}$)$_2$, —OP(O)(N($R^{12}$)$_2$, —$CH_2$P(O)(N($R^{12}$)$_2$, —$OCH_2$P(O)(N($R^{12}$)$_2$, —C(O)$OCH_2$P(O)(N($R^1$)$_2$)$_2$, —P(O)(N($R^{12}$)$_2$)($OR^{12}$), —OP(O)(N($R^{12}$)$_2$)($OR^{12}$), —$CH_2$P(O)(N($R^{12}$)$_2$)($OR^{12}$), —$OCH_2$P(O)(N($R^{12}$)$_2$)($OR^{12}$), —C(O)$OCH_2$P(O)(N($R^{12}$)$_2$)($OR^{12}$), —P(O)($R^{12}$)(N($R^{12}$)$_2$), —OP(O)($R^{12}$)(N($R^{12}$)$_2$), —$CH_2$P(O)($R^{12}$)(N($R^{12}$)$_2$), —$OCH_2$P(O)($R^{12}$)(N($R^{12}$)$_2$), C(O)$OCH_2$P(O)($R^{12}$($R^{12}$)$_2$), —Si($R^{12}$)$_3$, —S—$R^{12}$, —S(O)$R^{12}$, —S(O)(NH)$R^{12}$, —S(O)$_2$$R^{12}$ or —S(O)$_2$N($R^{13}$)($R^{14}$);
wherein any alkyl, alkenyl, alkynyl, cycloalkyl, haloalkyl, aryl, heteroaryl or heterocyclyl is optionally substituted with one to four $Z^{1a}$ groups;
each $Z^{1a}$ is independently oxo, halo, thioxo, —$NO_2$, cyano, —$N_3$, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O—$R^{12}$, —C(O)$R^{12}$, —C(O)O—$R^{12}$, —C(O)N($R^{13}$)($R^{14}$), —N($R^{13}$)($R^{14}$), —N($R^{13}$)$_2$($R^{14}$)$^+$, —N($R^{12}$)—C(O)$R^{12}$, —N($R^{12}$)C(O)O($R^{12}$), —N($R^{12}$)C(O)N($R^{13}$)($R^{14}$), —N($R^{12}$)S(O)$_2$($R^{12}$), —N($R^{12}$)S(O)$_2$—N($R^{13}$)($R^{14}$), —N($R^{12}$)S(O)$_2$O($R^{12}$), —OC(O)$R^{12}$, —OC(O)$OR^{12}$, —OC(O)—N($R^{13}$)($R^{14}$), —Si($R^{12}$)$_3$, —S—$R^{12}$, —S(O)$R^{12}$, —S(O)(NH)$R^{12}$, —S(O)$_2$$R^{12}$ or —S(O)$_2$N($R^{3}$)($R^{14}$);
wherein any alkenyl, alkynyl, cycloalkyl, aryl, heteroaryl or heterocyclyl is optionally substituted with one to four $Z^{1b}$ groups;
each $R^{12}$ is independently hydrogen, $C_{1-9}$ alkyl, $C_{2-6}$ alkenyl, $C_{2-6}$ alkynyl, $C_{3-15}$ cycloalkyl, aryl, heteroaryl or heterocyclyl;
wherein any alkyl, alkenyl, alkynyl, cycloalkyl, aryl, heteroaryl or heterocyclyl is optionally substituted with one to four $Z^{1b}$ groups;
$R^{13}$ and $R^{14}$ at each occurrence are each independently hydrogen, $C_{1-9}$ alkyl, $C_{2-6}$ alkenyl, $C_{2-6}$ alkynyl, $C_{3-15}$ cycloalkyl, aryl, heteroaryl or heterocyclyl;
wherein any alkyl, alkenyl, alkynyl, cycloalkyl, aryl, heteroaryl or heterocyclyl is optionally substituted with one to four $Z^{1b}$ groups, or $R^{13}$ and $R^{14}$ together with the nitrogen to which they are attached form a heterocyclyl, wherein said heterocyclyl is optionally substituted with one to four $Z^{1b}$ groups; and
each $Z^{1b}$ is independently oxo, thioxo, hydroxy, halo, —$NO_2$, —$N_3$, cyano, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O($C_{1-9}$ alkyl), —O($C_{2-6}$ alkenyl), —O($C_{2-6}$ alkynyl), —O($C_{3-15}$ cycloalkyl), —O($C_{1-8}$ haloalkyl), —O(aryl), —O(heteroaryl), —O(heterocyclyl), —$NH_2$, —NH($C_{1-9}$ alkyl), —NH($C_{2-6}$ alkenyl), —NH($C_{2-6}$ alkynyl), —NH($C_{3-15}$ cycloalkyl), —NH($C_{1-8}$ haloalkyl), —NH(aryl), —NH(heteroaryl), —NH(heterocyclyl), —N($C_{1-9}$ alkyl)$_2$, —N($C_{3-15}$ cycloalkyl)$_2$, —N($C_{2-6}$ alkenyl)$_2$, —N($C_{2-6}$ alkynyl)$_2$, —N($C_{3-15}$ cycloalkyl)$_2$, —N($C_{1-8}$ haloalkyl)$_2$, —N(aryl)$_2$, —N(heteroaryl)$_2$, —N(heterocyclyl)$_2$, —N($C_{1-9}$ alkyl)($C_{3-15}$ cycloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)($C_{1-8}$ haloalkyl), —N($C_{1-9}$ alkyl)(aryl), —N($C_{1-9}$ alkyl)(heteroaryl), —N($C_{1-9}$ alkyl)(heterocyclyl), —C(O)($C_{1-9}$ alkyl), —C(O)($C_{2-6}$ alkenyl), —C(O)($C_{2-6}$ alkynyl), —C(O)($C_{3-15}$ cycloalkyl), —C(O)($C_{1-8}$ haloalkyl), —C(O)(aryl), —C(O)(heteroaryl), —C(O)(heterocyclyl), —C(O)O($C_{1-9}$ alkyl), —C(O)O($C_{2-6}$ alkenyl), —C(O)O(C$_{2-6}$ alkynyl), —C(O)O(C$_{3-15}$ cycloalkyl), —C(O)O(C$_{1-8}$ haloalkyl), —C(O)O(aryl), —C(O)O(heteroaryl), —C(O)O(heterocyclyl), —C(O)NH$_2$, —C(O)NH(C$_{1-9}$ alkyl), —C(O)NH(C$_{2-6}$ alkenyl), —C(O)NH(C$_{2-6}$ alkynyl), —C(O)NH(C$_{3-15}$ cycloalkyl), —C(O)NH(C$_{1-8}$ haloalkyl), —C(O)NH(aryl), —C(O)NH(heteroaryl), —C(O)NH(heterocyclyl), —C(O)N(C$_{1-9}$ alkyl)$_2$, —C(O)N(C$_{3-15}$ cycloalkyl)$_2$, —C(O)N(C$_{2-6}$ alkenyl)$_2$, —C(O)N(C$_{2-6}$ alkynyl)$_2$, —C(O)N(C$_{3-15}$ cycloalkyl)$_2$, —C(O)N(C$_{1-8}$ haloalkyl)$_2$, —C(O)N(aryl)$_2$, —C(O)N(heteroaryl)$_2$, —C(O)N(heterocyclyl)$_2$, —NHC(O)(C$_{1-9}$ alkyl), —NHC(O)(C$_{2-6}$ alkenyl), —NHC(O)(C$_{2-6}$ alkynyl), —NHC(O)(C$_{3-15}$ cycloalkyl), —NHC(O)(C$_{1-8}$ haloalkyl), —NHC(O)(aryl), —NHC(O)(heteroaryl), —NHC(O)(heterocyclyl), —NHC(O)O(C$_{1-9}$ alkyl), —NHC(O)O(C$_{2-6}$ alkenyl), —NHC(O)O(C$_{2-6}$ alkynyl), —NHC(O)O(C$_{3-15}$ cycloalkyl), —NHC(O)O(C$_{1-8}$ haloalkyl), —NHC(O)O(aryl), —NHC(O)O(heteroaryl), —NHC(O)O(heterocyclyl), —NHC(O)NH(C$_{1-9}$ alkyl), —NHC(O)NH(C$_{2-6}$ alkenyl), —NHC(O)NH(C$_{2-6}$ alkynyl), —NHC(O)NH(C$_{3-15}$ cycloalkyl), —NHC(O)NH(C$_{1-8}$ haloalkyl), —NHC(O)NH(aryl), —NHC(O)NH(heteroaryl), —NHC(O)NH(heterocyclyl), —SH, —S(C$_{1-9}$ alkyl), —S(C$_{2-6}$ alkenyl), —S(C$_{2-6}$ alkynyl), —S(C$_{3-15}$ cycloalkyl), —S(C$_{1-8}$ haloalkyl), —S(aryl), —S(heteroaryl), —S(heterocyclyl), —NHS(O)(C$_{1-9}$ alkyl), —N(C$_{1-9}$ alkyl)(S(O)(C$_{1-9}$ alkyl), —S(O)N(C$_{1-9}$ alkyl)$_2$, —S(O)(C$_{1-9}$ alkyl), —S(O)(NH)(C$_{1-9}$ alkyl), —S(O)(C$_{2-6}$ alkenyl), —S(O)(C$_{2-6}$ alkynyl), —S(O)(C$_{3-15}$ cycloalkyl), —S(O)(C$_{1-8}$ haloalkyl), —S(O)(aryl), —S(O)(heteroaryl), —S(O)(heterocyclyl), —S(O)$_2$(C$_{1-9}$ alkyl), —S(O)$_2$(C$_{2-6}$ alkenyl), —S(O)$_2$(C$_{2-6}$ alkynyl), —S(O)$_2$(C$_{3-15}$ cycloalkyl), —S(O)$_2$(C$_{1-8}$ haloalkyl), —S(O)$_2$(aryl), —S(O)$_2$(heteroaryl), —S(O)$_2$(heterocyclyl), —S(O)$_2$NH(C$_{1-9}$ alkyl), or —S(O)$_2$N(C$_{1-9}$ alkyl)$_2$;

wherein any alkyl, cycloalkyl, aryl, heteroaryl, or heterocyclyl is optionally substituted with one to four halo, C$_{1-9}$ alkyl, C$_{1-8}$ haloalkyl, —OH, —NH$_2$, —NH(C$_{1-9}$ alkyl), —NH(C$_{3-15}$ cycloalkyl), —NH(C$_{1-8}$ haloalkyl), —NH(aryl), —NH(heteroaryl), —NH(heterocyclyl), —N(C$_{1-9}$ alkyl)$_2$, —N(C$_{3-15}$ cycloalkyl)$_2$, —NHC(O)(C$_{3-15}$ cycloalkyl), —NHC(O)(C$_{1-8}$ haloalkyl), —NHC(O)(aryl), —NHC(O)(heteroaryl), —NHC(O)(heterocyclyl), —NHC(O)O(C$_{1-9}$ alkyl), —NHC(O)O(C$_{2-6}$ alkynyl), —NHC(O)O(C$_{3-15}$ cycloalkyl), —NHC(O)O(C$_{1-8}$ haloalkyl), —NHC(O)O(aryl), —NHC(O)O(heteroaryl), —NHC(O)O(heterocyclyl), —NHC(O)NH(C$_{1-9}$ alkyl), —S(O)(NH)(C$_{1-9}$ alkyl), S(O)$_2$(C$_{1-9}$ alkyl), —S(O)$_2$(C$_{3-15}$ cycloalkyl), —S(O)$_2$(C$_{1-8}$ haloalkyl), —S(O)$_2$(aryl), —S(O)$_2$(heteroaryl), —S(O)$_2$(heterocyclyl), —S(O)$_2$NH(C$_{1-9}$ alkyl), —S(O)$_2$N(C$_{1-9}$ alkyl)$_2$, —O(C$_{3-15}$ cycloalkyl), —O(C$_{1-8}$ haloalkyl), —O(aryl), —O(heteroaryl), —O(heterocyclyl), or —O(C$_{1-9}$ alkyl);

or a pharmaceutically acceptable salt, stereoisomer, mixture of stereoisomers, or deuterated analog thereof.

Also provided are compounds of Formula IVA:

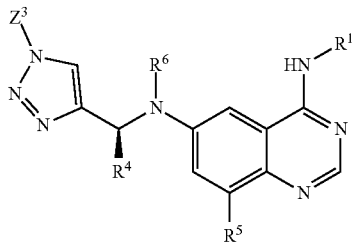

IVA wherein Z$^3$, R$^1$, R$^4$, R$^5$ and R$^6$ are as defined herein.

Some embodiments provide a method of using (or administering) the compounds of Formula I, or additional Formula(s) described throughout, in the treatment of a disease or condition in a mammal, particularly a human, that is amenable to treatment by an Cot modulator.

In certain embodiments, the disclosure provides pharmaceutical compositions comprising a therapeutically effective amount of a compound of the disclosure (e.g. a compound of Formula I or additional Formulas described throughout), and at least one pharmaceutically acceptable excipient.

DETAILED DESCRIPTION

Definitions and General Parameters

The following description sets forth exemplary methods, parameters and the like. It should be recognized, however, that such description is not intended as a limitation on the scope of the present disclosure but is instead provided as a description of exemplary embodiments.

As used in the present specification, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —C(O)NH$_2$ is attached through the carbon atom. A dash at the front or end of a chemical group is a matter of convenience; chemical groups may be depicted with or without one or more dashes without losing their ordinary meaning. A wavy line drawn through a line in a structure indicates a point of attachment of a group. Unless chemically or structurally required, no directionality is indicated or implied by the order in which a chemical group is written or named.

The prefix "C$_{u-v}$" indicates that the following group has from u to v carbon atoms. For example, "C$_{1-6}$ alkyl" indicates that the alkyl group has from 1 to 6 carbon atoms.

Reference to "about" a value or parameter herein includes (and describes) embodiments that are directed to that value or parameter per se. In certain embodiments, the term "about" includes the indicated amount ±10%. In other embodiments, the term "about" includes the indicated amount ±5%. In certain other embodiments, the term "about" includes the indicated amount ±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., C$_{1-20}$ alkyl), 1 to 8 carbon atoms (i.e., C$_{1-8}$ alkyl), 1 to 6 carbon atoms (i.e., C$_{1-6}$ alkyl), or 1 to 4 carbon atoms (i.e., C$_{1-4}$ alkyl). Examples of alkyl groups include methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, "butyl" includes n-butyl (i.e. —(CH$_2$)$_3$CH$_3$), sec-butyl (i.e. —CH(CH$_3$)CH$_2$CH$_3$), isobutyl (i.e. —CH$_2$CH (CH$_3$)$_2$) and tert-butyl (i.e. —C(CH$_3$)$_3$); and "propyl" includes n-propyl (i.e. —(CH$_2$)$_2$CH$_3$) and isopropyl (i.e. —CH(CH$_3$)$_2$).

"Alkenyl" refers to an alkyl group containing at least one carbon-carbon double bond and having from 2 to 20 carbon atoms (i.e., C$_{2-20}$ alkenyl), 2 to 8 carbon atoms (i.e., C$_{2-8}$ alkenyl), 2 to 6 carbon atoms (i.e., C$_{2-6}$ alkenyl), or 2 to 4 carbon atoms (i.e., C$_{2-4}$ alkenyl). Examples of alkenyl groups include ethenyl, propenyl, butadienyl (including 1,2-butadienyl and 1,3-butadienyl).

"Alkynyl" refers to an alkyl group containing at least one carbon-carbon triple bond and having from 2 to 20 carbon atoms (i.e., C$_{2-20}$ alkynyl), 2 to 8 carbon atoms (i.e., C$_{2-8}$ alkynyl), 2 to 6 carbon atoms (i.e., C$_{2-6}$ alkynyl), or 2 to 4 carbon atoms (i.e., C$_{2-4}$ alkynyl). The term "alkynyl" also includes those groups having one triple bond and one double bond.

"Alkoxy" refers to the group "alkyl-O—". Examples of alkoxy groups include methoxy, ethoxy, n-propoxy, isopropoxy, n-butoxy, tert-butoxy, sec-butoxy, n-pentoxy, n-hexoxy, and 1,2-dimethylbutoxy.

"Haloalkoxy" refers to an alkoxy group as defined above, wherein one or more hydrogen atoms are replaced by a halogen.

"Alkylthio" refers to the group "alkyl-S—".

"Acyl" refers to a group —C(O)R, wherein R is hydrogen, alkyl, cycloalkyl, heterocyclyl, aryl, heteroalkyl, or heteroaryl; each of which may be optionally substituted, as defined herein.

Examples of acyl include formyl, acetyl, cylcohexylcarbonyl, cyclohexylmethyl-carbonyl, and benzoyl.

"Amido" refers to both a "C-amido" group which refers to the group —C(O)NR$^y$R$^z$ and an "N-amido" group which refers to the group —NR$^y$C(O)R$^z$, wherein R$^y$ and R$^z$ are independently selected from the group consisting of hydrogen, alkyl, aryl, haloalkyl, or heteroaryl; each of which may be optionally substituted.

"Amino" refers to the group —NR$^y$R$^z$ wherein R$^y$ and R$^z$ are independently selected from the group consisting of hydrogen, alkyl, haloalkyl, aryl, or heteroaryl; each of which may be optionally substituted.

"Amidino" refers to —C(NH)(NH$_2$).

"Aryl" refers to an aromatic carbocyclic group having a single ring (e.g. monocyclic) or multiple rings (e.g. bicyclic or tricyclic) including fused systems. As used herein, aryl has 6 to 20 ring carbon atoms (i.e., C$_{6-20}$ aryl), 6 to 12 carbon ring atoms (i.e., C$_{6-12}$ aryl), or 6 to 10 carbon ring atoms (i.e., C$_{6-10}$ aryl). Examples of aryl groups include phenyl, naphthyl, fluorenyl, and anthryl. Aryl, however, does not encompass or overlap in any way with heteroaryl defined below. If one or more aryl groups are fused with a heteroaryl, the resulting ring system is heteroaryl. If one or more aryl groups are fused with a heterocyclyl, the resulting ring system is heterocyclyl.

"Azido" refers to —N$_3$.

"Carbamoyl" refers to both an "O-carbamoyl" group which refers to the group —O—C(O)NR$^y$R$^z$ and an "N-carbamoyl" group which refers to the group —NR$^y$C(O)OR$^z$, wherein R$^y$ and R$^z$ are independently selected from the group consisting of hydrogen, alkyl, aryl, haloalkyl, or heteroaryl; each of which may be optionally substituted.

"Carboxyl" refers to —C(O)OH.

"Carboxyl ester" refers to both —OC(O)R and —C(O)OR, wherein R is hydrogen, alkyl, cycloalkyl, heterocyclyl, aryl, heteroalkyl, or heteroaryl; each of which may be optionally substituted, as defined herein.

"Cyano" or "carbonitrile" refers to the group —CN.

"Cycloalkyl" refers to a saturated or partially unsaturated cyclic alkyl group having a single ring or multiple rings including fused, bridged, and spiro ring systems. The term "cycloalkyl" includes cycloalkenyl groups (i.e. the cyclic group having at least one double bond). As used herein, cycloalkyl has from 3 to 20 ring carbon atoms (i.e., C$_{3-20}$ cycloalkyl), 3 to 12 ring carbon atoms (i.e., C$_{3-12}$ cycloalkyl), 3 to 10 ring carbon atoms (i.e., C$_{3-10}$ cycloalkyl), 3 to 8 ring carbon atoms (i.e., C$_{3-8}$ cycloalkyl), or 3 to 6 ring carbon atoms (i.e., C$_{3-6}$ cycloalkyl). Examples of cycloalkyl groups include cyclopropyl, cyclobutyl, cyclopentyl, and cyclohexyl.

"Guanidino" refers to —NHC(NH)(NH$_2$).

"Hydrazino" refers to —NHNH$_2$.

"Imino" refers to a group —C(NR)R, wherein each R is alkyl, cycloalkyl, heterocyclyl, aryl, heteroalkyl, or heteroaryl; each of which may be optionally substituted, as defined herein.

"Halogen" or "halo" includes fluoro, chloro, bromo, and iodo. "Haloalkyl" refers to an unbranched or branched alkyl group as defined above, wherein one or more hydrogen atoms are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include difluoromethyl (—CHF$_2$) and trifluoromethyl (—CF$_3$).

"Heteroalkyl" refers to an alkyl group in which one or more of the carbon atoms (and any associated hydrogen atoms) are each independently replaced with the same or different heteroatomic group. The term "heteroalkyl" includes unbranched or branched saturated chain having carbon and heteroatoms. By way of example, 1, 2 or 3 carbon atoms may be independently replaced with the same or different heteroatomic group. Heteroatomic groups include, but are not limited to, —NR—, —O—, —S—, —S(O)—, —S(O)$_2$—, and the like, where R is H, alkyl, aryl, cycloalkyl, heteroalkyl, heteroaryl or heterocyclyl, each of which may be optionally substituted. Examples of heteroalkyl groups include —OCH$_3$, —CH$_2$OCH$_3$, —SCH$_3$, —CH$_2$SCH$_3$, —NRCH$_3$, and —CH$_2$NRCH$_3$, where R is hydrogen, alkyl, aryl, arylalkyl, heteroalkyl, or heteroaryl, each of which may be optionally substituted. As used herein, heteroalkyl include 1 to 10 carbon atoms, 1 to 8 carbon atoms, or 1 to 4 carbon atoms; and 1 to 3 heteroatoms, 1 to 2 heteroatoms, or 1 heteroatom.

"Heteroaryl" refers to an aromatic group having a single ring, multiple rings, or multiple fused rings, with one or more ring heteroatoms independently selected from nitrogen, oxygen, and sulfur. As used herein, heteroaryl includes 1 to 20 ring carbon atoms (i.e., C$_{1-20}$ heteroaryl), 3 to 12 ring carbon atoms (i.e., C$_{3-12}$ heteroaryl), or 3 to 8 carbon ring atoms (i.e., C$_{3-8}$ heteroaryl); and 1 to 5 heteroatoms, 1 to 4 heteroatoms, 1 to 3 ring heteroatoms, 1 to 2 ring heteroatoms, or 1 ring heteroatom independently selected from nitrogen, oxygen, and sulfur. Examples of heteroaryl groups include pyrimidinyl, purinyl, pyridyl, pyridazinyl, benzothiazolyl, and pyrazolyl. Examples of the fused-heteroaryl rings include, but are not limited to, benzo[d]thiazolyl, quinolinyl, isoquinolinyl, benzo[b]thiophenyl, indazolyl, benzo[d]imidazolyl, pyrazolo[1,5-a]pyridinyl, and imidazo[1,5-a]pyridinyl, where the heteroaryl can be bound via either ring of the fused system. Any aromatic ring, having a single or multiple fused rings, containing at least one heteroatom, is considered a heteroaryl regardless of the attachment to the remainder of the molecule (i.e., through any one of the fused rings). Heteroaryl does not encompass or overlap with aryl as defined above.

"Heterocyclyl" refers to a saturated or unsaturated cyclic alkyl group, with one or more ring heteroatoms independently selected from nitrogen, oxygen and sulfur. The term "heterocyclyl" includes heterocycloalkenyl groups (i.e. the heterocyclyl group having at least one double bond), bridged-heterocyclyl groups, fused-heterocyclyl groups, and spiro-heterocyclyl groups. A heterocyclyl may be a single ring or multiple rings wherein the multiple rings may be fused, bridged, or spiro. Any non-aromatic ring containing at least one heteroatom is considered a heterocyclyl, regardless of the attachment (i.e., can be bound through a carbon atom or a heteroatom). Further, the term heterocyclyl is intended to encompass any non-aromatic ring containing at least one heteroatom, which ring may be fused to an aryl or heteroaryl ring, regardless of the attachment to the remainder of the molecule. As used herein, heterocyclyl has 2 to 20 ring carbon atoms (i.e., $C_{2-20}$ heterocyclyl), 2 to 12 ring carbon atoms (i.e., $C_{2-12}$ heterocyclyl), 2 to 10 ring carbon atoms (i.e., $C_{2-10}$ heterocyclyl), 2 to 8 ring carbon atoms (i.e., $C_{2-8}$ heterocyclyl), 3 to 12 ring carbon atoms (i.e., $C_{3-12}$ heterocyclyl), 3 to 8 ring carbon atoms (i.e., $C_{3-8}$ heterocyclyl), or 3 to 6 ring carbon atoms (i.e., $C_{3-6}$ heterocyclyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen, and optionally one or more oxo groups. Examples of heterocyclyl groups include pyrrolidinyl, piperidinyl, piperazinyl, oxetanyl, dioxolanyl, azetidinyl, and morpholinyl. As used herein, the term "bridged-heterocyclyl" refers to a four- to ten-membered cyclic moiety connected at two non-adjacent atoms of the heterocyclyl with one or more (e.g. 1 or 2) four- to ten-membered cyclic moiety having at least one heteroatom where each heteroatom is independently selected from nitrogen, oxygen, and sulfur. As used herein, bridged-heterocyclyl includes bicyclic and tricyclic ring systems. Also used herein, the term "spiro-heterocyclyl" refers to a ring system in which a three- to ten-membered heterocyclyl has one or more additional ring, wherein the one or more additional ring is three- to ten-membered cycloalkyl or three- to ten-membered heterocyclyl, where a single atom of the one or more additional ring is also an atom of the three- to ten-membered heterocyclyl. Examples of the spiro-heterocyclyl rings include bicyclic and tricyclic ring systems, such as 2-oxa-7-azaspiro[3.5]nonanyl, 2-oxa-6-azaspiro[3.4]octanyl, and 6-oxa-1-azaspiro[3.3]heptanyl. Examples of the fused-heterocyclyl rings include, but are not limited to, 1,2,3,4-tetrahydroisoquinolinyl, 4,5,6,7-tetrahydrothieno[2,3-c]pyridinyl, indolinyl, and isoindolinyl (e.g., 2-methyl-isoquinolin-1(2H)-one), where the heterocyclyl can be bound via either ring of the fused system.

"Hydroxy" or "hydroxyl" refers to the group —OH.

"Oxo" refers to the group (═O) or (O).

"Nitro" refers to the group —NO$_2$.

"Sulfonyl" refers to the group —S(O)$_2$R, where R is alkyl, haloalkyl, heterocyclyl, cycloalkyl, heteroaryl, or aryl. Examples of sulfonyl are methylsulfonyl, ethylsulfonyl, phenylsulfonyl, and toluenesulfonyl.

"Alkylsulfonyl" refers to the group —S(O)$_2$R, where R is alkyl.

"Alkylsulfinyl" refers to the group —S(O)R, where R is alkyl.

"Thiocyanate" —SCN.

"Thiol" refers to the group —SR, where R is alkyl, haloalkyl, heterocyclyl, cycloalkyl, heteroaryl, or aryl.

"Thioxo" or "thione" refer to the group (═S) or (S).

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. Also, unless indicated explicitly otherwise, where combinations of groups are referred to herein as one moiety, e.g. arylalkyl, the last mentioned group contains the atom by which the moiety is attached to the rest of the molecule.

The terms "optional" or "optionally" means that the subsequently described event or circumstance may or may not occur, and that the description includes instances where said event or circumstance occurs and instances in which it does not. Also, the term "optionally substituted" refers to any one or more hydrogen atoms on the designated atom or group may or may not be replaced by a moiety other than hydrogen.

Some of the compounds exist as tautomers. Tautomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

Any formula or structure given herein, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl and $^{125}$I. Various isotopically labeled compounds of the present disclosure, for example those into which radioactive isotopes such as $^3$H, $^{13}$C and $^{14}$C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also includes "deuterated analogs" of compounds of Formula I in which from 1 to n hydrogens attached to a carbon atom is/are replaced by deuterium, in which n is the number of hydrogens in the molecule. Such compounds exhibit increased resistance to metabolism and are thus useful for increasing the half-life of any compound of Formula I when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound of Formula I.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

In many cases, the compounds of this disclosure are capable of forming acid and/or base salts by virtue of the presence of amino and/or carboxyl groups or groups similar thereto.

Provided are also pharmaceutically acceptable salts, hydrates, solvates, tautomeric forms, polymorphs, and prodrugs of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The term "pharmaceutically acceptable salt" of a given compound refers to salts that retain the biological effectiveness and properties of the given compound, and which are not biologically or otherwise undesirable. "Pharmaceutically acceptable salts" or "physiologically acceptable salts" include, for example, salts with inorganic acids and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts. Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like. Likewise, pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines (i.e., $NH_2$(alkyl)), dialkyl amines (i.e., HN(alkyl)$_2$), trialkyl amines (i.e., N(alkyl)$_3$), substituted alkyl amines (i.e., $NH_2$(substituted alkyl)), di(substituted alkyl) amines (i.e., HN(substituted alkyl)$_2$), tri (substituted alkyl) amines (i.e., N(substituted alkyl)$_3$), alkenyl amines (i.e., $NH_2$(alkenyl)), dialkenyl amines (i.e., HN(alkenyl)$_2$), trialkenyl amines (i.e., N(alkenyl)$_3$), substituted alkenyl amines (i.e., $NH_2$(substituted alkenyl)), di(substituted alkenyl) amines (i.e., HN(substituted alkenyl)$_2$), tri(substituted alkenyl) amines (i.e., N(substituted alkenyl)$_3$, mono-, di- or tri-cycloalkyl amines (i.e., $NH_2$(cycloalkyl), HN(cycloalkyl)$_2$, N(cycloalkyl)$_3$), mono-, di- or tri-arylamines (i.e., $NH_2$(aryl), HN(aryl)$_2$, N(aryl)$_3$), or mixed amines, etc. Specific examples of suitable amines include, by way of example only, isopropylamine, trimethyl amine, diethyl amine, tri(iso-propyl) amine, tri(n-propyl) amine, ethanolamine, 2-dimethylaminoethanol, piperazine, piperidine, morpholine, N-ethylpiperidine, and the like.

The term "substituted" means that any one or more hydrogen atoms on the designated atom or group is replaced with one or more substituents other than hydrogen, provided that the designated atom's normal valence is not exceeded. The one or more substituents include, but are not limited to, alkyl, alkenyl, alkynyl, alkoxy, acyl, amino, amido, amidino, aryl, azido, carbamoyl, carboxyl, carboxyl ester, cyano, guanidino, halo, haloalkyl, haloalkoxy, heteroalkyl, heteroaryl, heterocyclyl, hydroxy, hydrazino, imino, oxo, nitro, alkylsulfinyl, sulfonic acid, alkylsulfonyl, thiocyanate, thiol, thione, or combinations thereof. Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl)substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. Unless specified otherwise, where a group is described as optionally substituted, any substituents of the group are themselves unsubstituted. For example, in some embodiments, the term "substituted alkyl" refers to an alkyl group having one or more substituents including hydroxyl, halo, alkoxy, cycloalkyl, heterocyclyl, aryl, and heteroaryl. In other embodiments, the one or more substituents may be further substituted with halo, alkyl, haloalkyl, hydroxyl, alkoxy, cycloalkyl, heterocyclyl, aryl, or heteroaryl, each of which is substituted. In other embodiments, the substituents may be further substituted with halo, alkyl, haloalkyl, alkoxy, hydroxyl, cycloalkyl, heterocyclyl, aryl, or heteroaryl, each of which is unsubstituted.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

A "solvate" is formed by the interaction of a solvent and a compound. Solvates of salts of the compounds described herein are also provided. Hydrates of the compounds described herein are also provided.

List of Abbreviations and Acronyms

| Abbreviation | Meaning |
|---|---|
| °C | Degree Celsius |
| Ac | Acetyl |
| aq. | Aqueous |
| ATP | Adenosine triphosphate |
| br | Broad |
| BSA | Bovine serum albumin |
| Cbz | Carboxybenzyl |
| COD | Cyclooctadiene |
| COPD | Chronic obstructive pulmonary disease |
| Cot | Cancer Osaka Thyroid |
| d | Doublet |
| DCE | Dichloroethene |
| DCM | Dichloromethane |
| dd | Doublet of doublets |
| DIEA | Diisopropylethylamine |
| DMF | Dimethylformamide |
| DMSO | Dimethylsulfoxide |
| dt | Doublet-triplet |
| DTT | Dithiothreitol |
| EC$_{50}$ | The half maximal effective concentration |
| EGFR | Epidermal growth factor receptor |
| eq | Equivalents |
| ES/MS | Electrospray mass spectrometry |
| Et | Ethyl |
| FBS | Fetal bovine serum |
| g | Grams |
| HEPES | 2-[4-(2-hydroxyethyl)piperazin-1-yl]ethanesulfonic acid |
| HPLC | High pressure liquid chromatography |
| hrs | Hours |
| Hz | Hertz |
| IBD | Inflammatory bowel disease |
| i-pr | Isopropyl |
| J | Coupling constant (MHz) |
| Kg/kg | Kilogram |
| LCMS | Liquid chromatography-mass spectrometry |
| LPS | Lipopolysaccharide |
| M | Molar |
| m | multiplet |
| M+ | Mass peak |
| M + H+ | Mass peak plus hydrogen |
| Me | Methyl |
| mg | Milligram |
| MHz | Megahertz |
| ml/mL | Milliliter |
| mM | Millimolar |
| mmol | Millimole |
| MOPS | 3-Morpholinopropane-1-sulfonic acid |
| MS | Mass spectroscopy |
| Ms | Mesyl |
| nBu/Bu | Butyl |
| nL | Nanoliter |
| nm | Nanometer |
| NMR | Nuclear magnetic resonance |
| NMP | N-methylpyrrolidinone |
| NP-40 | Nonyl phenoxypolyethoxylethanol |
| Pd-C/Pd/C | Palladium on Carbon |
| pg | Pictogram |
| Ph | Phenyl |
| q | Quartet |
| q.s. | Quantity sufficient to achieve a stated function |
| RP | Reverse phase |
| RPMI | Roswell Park Memorial Institute medium |
| rt | Room temperature |
| s | Singlet |
| sat. | Saturated |
| t | Triplet |
| TEA | Triethanolamine |

-continued

| Abbreviation | Meaning |
|---|---|
| Tf | Trifluoromethanesulfonyl |
| TFA | Trifluoroacetic acid |
| THF | Tetrahydrofuran |
| Tpl2 | Tumor Progression Locus 2 |
| TR-FRET | Time-resolved fluorescence energy transfer |
| δ | Chemical shift (ppm) |
| μL/μl | Microliter |
| μM | Micromolar |

Compounds

Provided herein are compounds that function as modulators of Cot. In one aspect, provided is a compound having structure of Formula I:

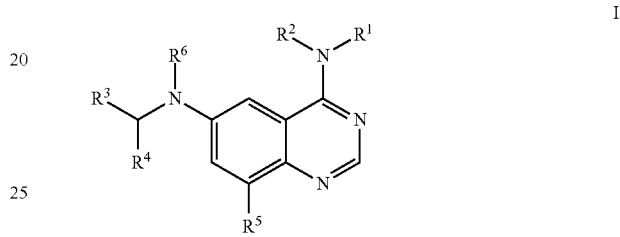

wherein
$R^1$ is $C_{1-9}$ alkyl, $C_{3-15}$ cycloalkyl, heterocyclyl, heteroaryl, or $C_{6-10}$ aryl;
  wherein each $C_{1-9}$ alkyl, $C_{3-15}$ cycloalkyl, heterocyclyl, heteroaryl, and $C_{6-10}$ aryl may be optionally substituted with one to four $Z^1$;
$R^2$ is hydrogen, —C(O)—$R^7$, —C(O)O—$R^7$, —C(O)N($R^7$)$_2$, or $C_{1-9}$ alkyl;
$R^3$ is heterocyclyl or heteroaryl;
  wherein each heterocyclyl or heteroaryl is optionally substituted with one to four $Z^3$;
$R^4$ is aryl, heterocyclyl, or heteroaryl;
  wherein each aryl, heterocyclyl, or heteroaryl is optionally substituted with one to four $Z^4$;
$R^5$ is hydrogen, halo, cyano, —NO$_2$, —O—$R^7$, —N($R^8$)($R^9$), —S(O)—$R^7$, —S(O)$_2R^7$, —S(O)$_2$N($R^7$)$_2$, —C(O)$R^7$, —OC(O)—$R^7$, —C(O)O—$R^7$, —OC(O)O—$R^7$, —OC(O)N($R^{10}$)($R^{11}$), —C(O)N($R^7$)$_2$, —N($R^7$)C(O)($R^7$), $C_{1-9}$ alkyl, $C_{2-6}$ alkenyl, $C_{2-6}$ alkynyl, $C_{1-9}$ alkylthio, $C_{1-6}$ haloalkyl, $C_{3-15}$ cycloalkyl, aryl, heterocyclyl, or heteroaryl;
  wherein each $C_{1-9}$ alkyl, $C_{2-6}$ alkenyl, $C_{2-6}$ alkynyl, $C_{1-9}$ alkylthio, $C_{1-6}$ haloalkyl, $C_{3-15}$ cycloalkyl, aryl, heterocyclyl, and heteroaryl may be optionally substituted with one to four $Z^5$;
$R^6$ is hydrogen, —C(O)—$R^7$, —C(O)O—$R^7$, —C(O)N($R^7$)$_2$, $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl;
  wherein each $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, and heteroaryl may be optionally substituted with one to four $Z^6$;
each $R^7$ is independently hydrogen, $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl;
  wherein each $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, and heteroaryl may be optionally substituted with one to four $Z^7$;

R$^8$ and R$^9$ at each occurrence are independently hydrogen, —S(O)$_2$R$^{10}$, —C(O)—R$^{10}$, —C(O)O—R$^{10}$, —C(O)N(R$^{10}$)(R$^{11}$), C$_{1-9}$ alkyl, C$_{2-6}$ alkenyl, C$_{2-6}$ alkynyl, C$_{1-6}$ haloalkyl, C$_{3-15}$ cycloalkyl, aryl, heterocyclyl, or heteroaryl;
  wherein each C$_{1-9}$ alkyl, C$_{2-6}$ alkenyl, C$_{2-6}$ alkynyl, C$_{1-6}$ haloalkyl, C$_{3-15}$ cycloalkyl, aryl, heterocyclyl, or heteroaryl may be optionally substituted with one to four Z$^8$;

R$^{10}$ and R$^{11}$ at each occurrence are independently hydrogen, C$_{1-9}$ alkyl, C$_{2-6}$ alkenyl, C$_{2-6}$ alkynyl, C$_{1-6}$ haloalkyl, C$_{3-15}$ cycloalkyl, aryl, heterocyclyl, or heteroaryl,
  wherein each C$_{1-9}$ alkyl, C$_{2-6}$ alkenyl, C$_{2-6}$ alkynyl, C$_{1-6}$ haloalkyl, C$_{3-15}$ cycloalkyl, aryl, heterocyclyl, and heteroaryl optionally is substituted with one to four Z$^b$;

each Z$^1$, Z$^3$, Z$^4$, Z$^5$, Z$^6$, Z$^7$ and Z$^8$ is independently hydrogen, oxo, halo, —NO$_2$, —N$_3$, cyano, thioxo, C$_{1-9}$ alkyl, C$_{2-6}$ alkenyl, C$_{2-6}$ alkynyl, C$_{3-15}$ cycloalkyl, C$_{1-8}$ haloalkyl, aryl, heteroaryl, heterocyclyl, —O—R$^{12}$, —C(O)—R$^{12}$, —C(O)O—R$^{12}$, —C(O)—N(R$^{13}$)(R$^{14}$), —N(R$^{13}$)(R$^{14}$), —N(R$^{13}$)$_2$(R$^{14}$)$^+$, —N(R$^{12}$)C(O)—R$^{12}$, —N(R$^{12}$)C(O)O—R$^{12}$, —N(R$^{12}$)C(O)N(R$^{13}$)(R$^{14}$), —N(R$^{12}$)S(O)$_2$(R$^{12}$), —NR$^{12}$S(O)$_2$N(R$^{13}$)(R$^{14}$), —NR$^{12}$S(O)$_2$O(R$^{12}$), —OC(O)R$^{12}$, —OC(O)—N(R$^{13}$)(R$^{14}$), —P(O)(OR$^{12}$)$_2$, —OP(O)(OR$^{12}$)$_2$, —C$_{12}$P(O)(OR$^{12}$)$_2$, —OCH$_2$P(O)(OR$^{12}$)$_2$, —C(O)OCH$_2$P(O)(OR$^{12}$)$_2$, —P(O)(R$^{12}$)(OR$^{12}$), —OP(O)(R$^{12}$)R$^{12}$), —CH$_2$P(O)(R$^{12}$)(OR$^{12}$) OCH$_2$P(O)(R$^{12}$)(OR$^{12}$), —C(O)OCH$_2$P(O)(R$^{12}$)(OR$^{12}$), —P(O)(N(R$^{12}$)$_2$)$_2$, —OP(O)(N(R$^{12}$)$_2$)$_2$, —CH$_2$P(O)(N(R$^{12}$)$_2$)$_2$, —OCH$_2$P(O)(N(R$^{12}$)$_2$)$_2$, —C(O)OCH$_2$P(O)(N(R$^{12}$)$_2$)$_2$, —P(O)(N(R$^{12}$)$_2$)(OR$^{12}$), —OP(O)(N(R$^{12}$)$_2$)(OR$^{12}$), —CH$_2$P(O)(N(R$^{12}$)$_2$)(OR$^{12}$), —OCH$_2$P(O)(N(R$^{12}$)$_2$)(OR$^{12}$), —C(O)OCH$_2$P(O)(N(R$^{12}$)$_2$)(OR$^{12}$), —P(O)(R$^{12}$)(N(R$^{12}$)$_2$), —OP(O)(R$^{12}$)(N(R$^{12}$)$_2$), —CH$_2$P(O)(R$^{12}$)(N(R$^{12}$)$_2$), —OCH$_2$P(O)(R$^{12}$)(N(R$^{12}$)$_2$), —C(O)OCH$_2$P(O)(R$^{12}$)(N(R$^{12}$)$_2$), —Si(R$^{12}$)$_3$, —S—R$^{12}$, —S(O)R$^{12}$, —S(O)(NH)R$^{12}$, —S(O)$_2$R$^{12}$ or —S(O)$_2$N(R$^{13}$)(R$^{14}$);
  wherein any alkyl, alkenyl, alkynyl, cycloalkyl, haloalkyl, aryl, heteroaryl or heterocyclyl is optionally substituted with one to four Z$^{1a}$ groups;

each Z$^{1a}$ is independently oxo, halo, thioxo, —NO$_2$, cyano, —N$_3$, C$_{1-9}$ alkyl, C$_{2-6}$ alkenyl, C$_{2-6}$ alkynyl, C$_{3-15}$ cycloalkyl, C$_{1-8}$ haloalkyl, aryl, heteroaryl, heterocyclyl, —O—R$^{12}$, —C(O)R$^{12}$, —C(O)O—R$^{12}$, —C(O)N(R$^{13}$)(R$^{14}$), —N(R$^{13}$)(R$^{14}$), —N(R$^{13}$)$_2$(R$^{14}$)$^+$, —N(R$^{12}$)—C(O)R$^{12}$, —N(R$^{12}$)C(O)O(R$^{12}$), —N(R$^{12}$)C(O)N(R$^{13}$)(R$^{14}$), —N(R$^{12}$)S(O)$_2$(R$^{12}$), —N(R$^{12}$)S(O)$_2$—N(R$^{13}$)(R$^{14}$), —N(R$^{12}$)S(O)$_2$O(R$^{12}$), —OC(O)R, —OC(O)OR$^{12}$, —OC(O)—N(R$^{13}$)(R$^{14}$), —Si(R$^{12}$)$_3$, —S—R$^{12}$, —S(O)R$^{12}$, —S(O)(NH)R$^{12}$, —S(O)$_2$R$^{12}$ or —S(O)$_2$N(R$^{13}$)(R$^{14}$);
  wherein any alkenyl, alkynyl, cycloalkyl, aryl, heteroaryl or heterocyclyl is optionally substituted with one to four Z$^{1b}$ groups;

each R$^{12}$ is independently hydrogen, C$_{1-9}$ alkyl, C$_{2-6}$ alkenyl, C$_{2-6}$ alkynyl, C$_{3-15}$ cycloalkyl, aryl, heteroaryl or heterocyclyl,
  wherein any alkyl, alkenyl, alkynyl, cycloalkyl, aryl, heteroaryl or heterocyclyl is optionally substituted with one to four Z$^{1b}$ groups;

R$^{13}$ and R$^{14}$ at each occurrence are each independently hydrogen, C$_{1-9}$ alkyl, C$_{2-6}$ alkenyl, C$_{2-6}$ alkynyl, C$_{3-15}$ cycloalkyl, aryl, heteroaryl or heterocyclyl;
  wherein any alkyl, alkenyl, alkynyl, cycloalkyl, aryl, heteroaryl or heterocyclyl is optionally substituted with one to four Z$^{1b}$ groups, or R$^{13}$ and R$^{14}$ together with the nitrogen to which they are attached form a heterocyclyl, wherein said heterocyclyl is optionally substituted with one to four Z$^{1b}$ groups;

each Z$^{1b}$ is independently oxo, thioxo, hydroxy, halo, —NO$_2$, —N$_3$, cyano, C$_{1-9}$ alkyl, C$_{2-6}$ alkenyl, C$_{2-6}$ alkynyl, C$_{3-15}$ cycloalkyl, C$_{1-8}$ haloalkyl, aryl, heteroaryl, heterocyclyl, —O(C$_{1-9}$ alkyl), —O(C$_{2-6}$ alkenyl), —O(C$_{2-6}$ alkynyl), —O(C$_{3-15}$ cycloalkyl), —O(C$_{1-8}$ haloalkyl), —O(aryl), —O(heteroaryl), —O(heterocyclyl), —NH$_2$, —NH(C$_{1-9}$ alkyl), —NH(C$_{2-6}$ alkenyl), —NH(C$_{2-6}$ alkynyl), —NH(C$_{3-15}$ cycloalkyl), —NH(C$_{1-8}$ haloalkyl), —NH(aryl), —NH(heteroaryl), —NH(heterocyclyl), —N(C$_{1-9}$ alkyl)$_2$, —N(C$_{3-15}$ cycloalkyl)$_2$, —N(C$_{2-6}$ alkenyl)$_2$, —N(C$_{2-6}$ alkynyl)$_2$, —N(C$_{3-15}$ cycloalkyl)$_2$, —N(C$_{1-8}$ haloalkyl)$_2$, —N(aryl)$_2$, —N(heteroaryl)$_2$, —N(heterocyclyl)$_2$, —N(C$_{1-9}$ alkyl)(C$_{3-15}$ cycloalkyl), —N(C$_{1-9}$ alkyl)(C$_{2-6}$ alkenyl), —N(C$_{1-9}$ alkyl)(C$_{2-6}$ alkynyl), —N(C$_{1-9}$ alkyl)(C$_{3-15}$ cycloalkyl), —N(C$_{1-9}$ alkyl)(C$_{1-8}$ haloalkyl), —N(C$_{1-9}$ alkyl)(aryl), —N(C$_{1-9}$ alkyl)(heteroaryl), —N(C$_{1-9}$ alkyl)(heterocyclyl), —C(O)(C$_{1-9}$ alkyl), —C(O)(C$_{2-6}$ alkenyl), —C(O)(C$_{2-6}$ alkynyl), —C(O)(C$_{3-15}$ cycloalkyl), —C(O)(C$_{1-8}$ haloalkyl), —C(O)(aryl), —C(O)(heteroaryl), —C(O)(heterocyclyl), —C(O)O(C$_{1-9}$ alkyl), —C(O)O(C$_{2-6}$ alkenyl), —C(O)O(C$_{2-6}$ alkynyl), —C(O)O(C$_{3-15}$ cycloalkyl), —C(O)O(C$_{1-8}$ haloalkyl), —C(O)O(aryl), —C(O)O(heteroaryl), —C(O)O(heterocyclyl), —C(O)NH$_2$, —C(O)NH(C$_{1-9}$ alkyl), —C(O)NH(C$_{2-6}$ alkenyl), —C(O)NH(C$_{2-6}$ alkynyl), —C(O)NH(C$_{3-15}$ cycloalkyl), —C(O)NH(C$_{1-8}$ haloalkyl), —C(O)NH(aryl), —C(O)NH(heteroaryl), —C(O)NH(heterocyclyl), —C(O)N(C$_{1-9}$ alkyl)$_2$, —C(O)N(C$_{3-15}$ cycloalkyl)$_2$, —C(O)N(C$_{2-6}$ alkenyl)$_2$, —C(O)N(C$_{2-6}$ alkynyl)$_2$, —C(O)N(C$_{3-15}$ cycloalkyl)$_2$, —C(O)N(C$_{1-8}$ haloalkyl)$_2$, —C(O)N(aryl)$_2$, —C(O)N(heteroaryl)$_2$, —C(O)N(heterocyclyl)$_2$, —NHC(O)(C$_{1-9}$ alkyl), —NHC(O)(C$_{2-6}$ alkenyl), —NHC(O)(C$_{2-6}$ alkynyl), —NHC(O)(C$_{3-15}$ cycloalkyl), —NHC(O)(C$_{1-8}$ haloalkyl), —NHC(O)(aryl), —NHC(O)(heteroaryl), —NHC(O)(heterocyclyl), —NHC(O)O(C$_{1-9}$ alkyl), —NHC(O)O(C$_{2-6}$ alkenyl), —NHC(O)O(C$_{2-6}$ alkynyl), —NHC(O)O(C$_{3-15}$ cycloalkyl), —NHC(O)O(C$_{1-8}$ haloalkyl), —NHC(O)O(aryl), —NHC(O)O(heteroaryl), —NHC(O)O(heterocyclyl), —NHC(O)NH(C$_{1-9}$ alkyl), —NHC(O)NH(C$_{2-6}$ alkenyl), —NHC(O)NH(C$_{2-6}$ alkynyl), —NHC(O)NH(C$_{3-15}$ cycloalkyl), —NHC(O)NH(C$_{1-8}$ haloalkyl), —NHC(O)NH(aryl), —NHC(O)NH(heteroaryl), —NHC(O)NH(heterocyclyl), —SH, —S(C$_{1-9}$ alkyl), —S(C$_{2-6}$ alkenyl), —S(C$_{2-6}$ alkynyl), —S(C$_{3-15}$ cycloalkyl), —S(C$_{1-8}$ haloalkyl), —S(aryl), —S(heteroaryl), —S(heterocyclyl), —NHS(O)(C$_{1-9}$ alkyl), —N(C$_{1-9}$ alkyl)(S(O)(C$_{1-9}$ alkyl), —S(O)N(C$_{1-9}$ alkyl)$_2$, —S(O)(C$_{1-9}$ alkyl), —S(O)(NH)(C$_{1-9}$ alkyl), —S(O)(C$_{2-6}$ alkenyl), —S(O)(C$_{2-6}$ alkynyl), —S(O)(C$_{3-15}$ cycloalkyl), —S(O)(C$_{1-8}$ haloalkyl), —S(O)(aryl), —S(O)(heteroaryl), —S(O)(heterocyclyl), —S(O)$_2$(C$_{1-9}$ alkyl), —S(O)$_2$(C$_{2-6}$ alkenyl), —S(O)$_2$(C$_{2-6}$ alkynyl), —S(O)$_2$(C$_{3-15}$ cycloalkyl), —S(O)$_2$(C$_{1-8}$ haloalkyl), —S(O)$_2$(aryl), —S(O)$_2$(heteroaryl), —S(O)$_2$(heterocyclyl), —S(O)$_2$NH(C$_{1-9}$ alkyl), or —S(O)$_2$N(C$_{1-9}$ alkyl)$_2$;
  wherein any alkyl, cycloalkyl, aryl, heteroaryl, or heterocyclyl is optionally substituted with one to four halo, C$_{1-9}$ alkyl, C$_{1-8}$ haloalkyl, —OH, —NH$_2$, —NH(C$_{1-9}$ alkyl), —NH(C$_{3-15}$ cycloalkyl), —NH(C$_{1-8}$ haloalkyl), —NH(aryl), —NH(heteroaryl), —NH(heterocyclyl), —N(C$_{1-9}$ alkyl)$_2$, —N(C$_{3-15}$ cycloalkyl)$_2$, —NHC(O)(C$_{3-15}$ cycloalkyl), —NHC(O)(C$_{1-8}$ haloalkyl), —NHC(O)(aryl), —NHC(O)(heteroaryl), —NHC(O)(heterocyclyl), —NHC(O)O(C$_{1-9}$ alkyl), —NHC(O)O(C$_{2-6}$ alkynyl), —NHC(O)O($C_{3-15}$ cycloalkyl), —NHC(O)O ($C_{1-8}$ haloalkyl), —NHC(O)O(aryl), —NHC(O)O(heteroaryl), —NHC(O)O(heterocyclyl), —NHC(O)NH ($C_{1-9}$ alkyl), —S(O)(NH)($C_{1-9}$ alkyl), S(O)$_2$($C_{1-9}$ alkyl), —S(O)$_2$($C_{3-15}$ cycloalkyl), —S(O)$_2$($C_{1-8}$ haloalkyl), —S(O)$_2$(aryl), —S(O)$_2$(heteroaryl), —S(O)$_2$(heterocyclyl), —S(O)$_2$NH($C_{1-9}$ alkyl), —S(O)$_2$N($C_{1-9}$ alkyl)$_2$, —O($C_{3-15}$ cycloalkyl), —O($C_{1-8}$ haloalkyl), —O(aryl), —O(heteroaryl), —O(heterocyclyl), or —O($C_{1-9}$ alkyl);

m is 0, 1, or 2;

or a pharmaceutically acceptable salt, stereoisomer, mixture of stereoisomers, or deuterated analog thereof.

In one aspect, provided is a compound having the structure of Formula I:

wherein
$R^1$ is $C_{1-9}$ alkyl or $C_{3-15}$ cycloalkyl;
  wherein each $C_{1-9}$ alkyl and $C_{3-15}$ cycloalkyl may be optionally substituted with one to four $Z^1$; $R^2$ is hydrogen, —C(O)—$R^7$, —C(O)O—$R^7$, —C(O)N($R^7$)$_2$, or $C_{1-9}$ alkyl;
$R^3$ is heterocyclyl or heteroaryl;
  wherein each heterocyclyl or heteroaryl is optionally substituted with one to four $Z^3$;
$R^4$ is aryl, heterocyclyl, or heteroaryl;
  wherein each aryl, heterocyclyl, or heteroaryl is optionally substituted with one to four $Z^4$;
$R^5$ is hydrogen, halo, cyano, —NO$_2$, —O—$R^7$, —N($R^8$)($R^9$), —S(O)—$R^7$, —S(O)$_2$$R^7$, —S(O)$_2$N($R^7$)$_2$, —C(O)$R^7$, —OC(O)—$R^7$, —C(O)O—$R^7$, —OC(O)O—$R^7$, —OC(O)N($R^{10}$)($R^{11}$), —C(O)N($R^7$)$_2$, —N($R^7$)C(O)($R^7$), $C_{1-9}$ alkyl, $C_{2-6}$ alkenyl, $C_{2-6}$ alkynyl, $C_{1-9}$ alkylthio, $C_{1-6}$ haloalkyl, $C_{3-15}$ cycloalkyl, aryl, heterocyclyl, or heteroaryl;
  wherein each $C_{1-9}$ alkyl, $C_{2-6}$ alkenyl, $C_{2-6}$ alkynyl, $C_{1-9}$ alkylthio, $C_{1-6}$ haloalkyl, $C_{3-15}$ cycloalkyl, aryl, heterocyclyl, and heteroaryl may be optionally substituted with one to four $Z^5$;
$R^6$ is hydrogen, —C(O)—$R^7$, —C(O)O—$R^7$, —C(O)N ($R^7$)$_2$, $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl;
  wherein each $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, and heteroaryl may be optionally substituted with one to four $Z^6$;
each $R^7$ is independently hydrogen, $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl;
  wherein each $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, and heteroaryl may be optionally substituted with one to four $Z^7$;

$R^8$ and $R^9$ at each occurrence are independently hydrogen, —S(O)$_2$$R^{10}$, —C(O)—$R^{10}$, —C(O)O—$R^{10}$, —C(O)N ($R^{10}$)($R^{11}$), $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl;
  wherein each $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl may be optionally substituted with one to four $Z^8$;
$R^{10}$ and $R^{11}$ at each occurrence are independently hydrogen, $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl,
  wherein each $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, and heteroaryl optionally is substituted with one to four $Z^b$;
each $Z^1$, $Z^3$, $Z^4$, $Z^5$, $Z^6$, $Z^7$ and $Z^8$ is independently hydrogen, oxo, halo, —NO$_2$, —N$_3$, cyano, thioxo, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O—$R^{12}$, —C(O)—$R^{12}$, —C(O)O—$R^{12}$, —C(O)—N($R^{13}$)($R^{14}$), —N($R^{13}$)($R^{14}$), —N($R^{13}$)$_2$($R^{14}$)$^+$, —N($R^{12}$)C(O)—$R^{12}$, —N($R^{12}$)C(O) O—$R^{12}$, —N($R^{12}$)C(O)N($R^{13}$)($R^{14}$), N($R^{12}$)S(O)$_2$($R^{12}$), —NR$^{12}$S(O)$_2$N($R^{13}$)($R^{14}$), —NR$^{12}$S(O)$_2$O($R^{12}$), —OC (O)$R^{12}$, —OC(O)—N($R^{13}$)($R^{14}$), —P(O)(OR$^{12}$), —OP (O)(OR$^{12}$)$_2$, —CH$_2$P(O)(OR$^{12}$)$_2$, —OCH$_2$P(O)(OR$^{12}$)$_2$, —C(O)OCH$_2$P(O)(OR$^{12}$)$_2$, —P(O)(R$^{12}$)(OR$^{12}$), —OP (O)(R$^{12}$)(OR$^{12}$), —CH$_2$P(O)(R$^{12}$)OR$^{12}$), —OCH$_2$P(O) (R$^{12}$)(OR$^{12}$), —C(O)OCH$_2$P(O)(R$^{12}$)(OR$^{12}$). —P(O)(N (R$^{12}$)$_2$, —OP(O)(N(R$^{12}$)$_2$)$_2$, —CH$_2$P(O)(N(R$^{12}$)$_2$)$_2$, —OCH$_2$P(O)(N(R$^{12}$)$_2$, —C(O)OCH$_2$P(O)(N(R$^{12}$)$_2$), —P(O)(N(R$^{12}$)$_2$)(OR$^{12}$), —OP(O)(N(R$^{12}$)$_2$)(OR$^{12}$), —CH$_2$P(O)(N(R$^{12}$)$_2$)(OR$^{12}$), —OCH$_2$P(O)(N(R$^{13}$)$_2$) (OR$^{12}$), —C(O)OCH$_2$P(O)(N(R$^{12}$)$_2$)(OR$^{12}$). —P(O)(R$^{12}$) (N(R$^{12}$)$_2$), —OP(O)(R$^{12}$)(N(R$^2$)$_2$), —CH$_2$P(O)(R$^{12}$)(N (R$^{12}$)$_2$), —OCH$_2$P(O)(R$^{12}$)$_2$)(N(R$^{12}$)$_2$), —C(O)OCH$_2$P (O)(R$^{12}$)(N(R$^{12}$)$_2$), —Si(R$^{12}$)$_3$, —S—R$^{12}$, —S(O)R$^{12}$, —S(O)(NH)R$^{12}$, —S(O)$_2$R$^{12}$ or —S(O)$_2$N(R$^{13}$)(R$^{14}$);
  wherein any alkyl, alkenyl, alkynyl, cycloalkyl, haloalkyl, aryl, heteroaryl or heterocyclyl is optionally substituted with one to four $Z^{1a}$ groups;
each $Z^{1a}$ is independently oxo, halo, thioxo, —NO$_2$, cyano, —N$_3$, $C_{1-9}$ alkyl, $C_{2-6}$ alkenyl, $C_{2-6}$ alkynyl, $C_{3-15}$ cycloalkyl, $C_{1-8}$ haloalkyl, $C_{1-8}$ hydroxyalkyl, aryl, heteroaryl, heterocyclyl, —O—R$^{12}$, —C(O)R$^{12}$, —C(O) O—R$^{12}$, —C(O)N(R$^{13}$)(R$^{14}$), —N(R$^{13}$)(R$^{14}$), —N(R$^{13}$)$_2$ (R$^{14}$)$^+$, —N(R$^{12}$)—C(O)R$^{12}$, —N(R$^{12}$)C(O)O(R$^{12}$), —N(R$^{12}$)C(O)N(R$^{13}$)(R$^{14}$), —N(R$^{12}$)S(O)$_2$(R$^{12}$), —N(R$^{12}$)S(O)$_2$—N(R$^{13}$)(R$^{14}$), —N(R$^{12}$)S(O)$_2$O(R$^2$), —OC(O)R$^{12}$, —OC(O)OR$^{12}$, —OC(O)—N(R$^{13}$)(R$^{14}$), —C(O)N(R$^{12}$)—S(O)$_2$R$^{12}$, —Si(R$^{12}$)$_3$, —S—R$^{12}$, —S(O)R$^{12}$, —S(O)(NH)R$^{12}$, —S(O)$_2$R$^{12}$ or —S(O)$_2$N (R$^{13}$)(R$^{14}$);
  wherein any alkenyl, alkynyl, cycloalkyl, aryl, heteroaryl or heterocyclyl is optionally substituted with one to four $Z^{1b}$ groups;
each $R^{12}$ is independently hydrogen, $C_{1-9}$ alkyl, $C_{2-6}$ alkenyl, $C_{2-6}$ alkynyl, $C_{3-15}$ cycloalkyl, aryl, heteroaryl or heterocyclyl,
  wherein any alkyl, alkenyl, alkynyl, cycloalkyl, aryl, heteroaryl or heterocyclyl is optionally substituted with one to four $Z^{1b}$ groups;
$R^{13}$ and $R^{14}$ at each occurrence are each independently hydrogen, $C_{1-9}$ alkyl, $C_{2-6}$ alkenyl, $C_{2-6}$ alkynyl, $C_{3-15}$ cycloalkyl, aryl, heteroaryl or heterocyclyl;
  wherein any alkyl, alkenyl, alkynyl, cycloalkyl, aryl, heteroaryl or heterocyclyl is optionally substituted with one to four $Z^{1b}$ groups, or $R^{13}$ and $R^{14}$ together with the nitrogen to which they are attached form a heterocyclyl, wherein said heterocyclyl is optionally substituted with one to four $Z^{1b}$ groups;

each $Z^{1b}$ is independently oxo, thioxo, hydroxy, halo, —NO₂, —N₃, cyano, C₁₋₉ alkyl, C₂₋₆ alkenyl, C₂₋₆ alkynyl, C₃₋₁₅ cycloalkyl, C₁₋₈ haloalkyl, aryl, heteroaryl, heterocyclyl, —O(C₁₋₉ alkyl), —O(C₂₋₆ alkenyl), —O(C₂₋₆ alkynyl), —O(C₃₋₁₅ cycloalkyl), —O(C₁₋₈ haloalkyl), —O(aryl), —O(heteroaryl), —O(heterocyclyl), —NH₂, —NH(C₁₋₉ alkyl), —NH(C₂₋₆ alkenyl), —NH(C₂₋₆ alkynyl), —NH(C₃₋₁₅ cycloalkyl), —NH(C₁₋₈ haloalkyl), —NH(aryl), —NH(heteroaryl), —NH(heterocyclyl), —N(C₁₋₉ alkyl)₂, —N(C₃₋₁₅ cycloalkyl)₂, —N(C₂₋₆ alkenyl)₂, —N(C₂₋₆ alkynyl)₂, —N(C₃₋₁₅ cycloalkyl)₂, —N(C₁₋₈ haloalkyl)₂, —N(aryl)₂, —N(heteroaryl)₂, —N(heterocyclyl)₂, —N(C₁₋₉ alkyl)(C₃₋₁₅ cycloalkyl), —N(C₁₋₉ alkyl)(C₂₋₆ alkenyl), —N(C₁₋₉ alkyl)(C₂₋₆ alkynyl), —N(C₁₋₉ alkyl)(C₃₋₁₅ cycloalkyl), —N(C₁₋₉ alkyl)(C₁₋₈ haloalkyl), —N(C₁₋₉ alkyl)(aryl), —N(C₁₋₉ alkyl)(heteroaryl), —N(C₁₋₉ alkyl)(heterocyclyl), —C(O)(C₁₋₉ alkyl), —C(O)(C₂₋₆ alkenyl), —C(O)(C₂₋₆ alkynyl), —C(O)(C₃₋₁₅ cycloalkyl), —C(O)(C₁₋₈ haloalkyl), —C(O)(aryl), —C(O)(heteroaryl), —C(O)(heterocyclyl), —C(O)O(C₁₋₉ alkyl), —C(O)O(C₂₋₆ alkenyl), —C(O)O(C₂₋₆ alkynyl), —C(O)O(C₃₋₁₅ cycloalkyl), —C(O)O(C₁₋₈ haloalkyl), —C(O)O(aryl), —C(O)O(heteroaryl), —C(O)O(heterocyclyl), —C(O)NH₂, —C(O)NH(C₁₋₉ alkyl), —C(O)NH(C₂₋₆ alkenyl), —C(O)NH(C₂₋₆ alkynyl), —C(O)NH(C₃₋₁₅ cycloalkyl), —C(O)NH(C₁₋₈ haloalkyl), —C(O)NH(aryl), —C(O)NH(heteroaryl), —C(O)NH(heterocyclyl), —C(O)N(C₁₋₉ alkyl)₂, —C(O)N(C₃₋₁₅ cycloalkyl)₂, —C(O)N(C₂₋₆ alkenyl)₂, —C(O)N(C₂₋₆ alkynyl)₂, —C(O)N(C₃₋₁₅ cycloalkyl)₂, —C(O)N(C₁₋₈ haloalkyl)₂, —C(O)N(aryl)₂, —C(O)N(heteroaryl)₂, —C(O)N(heterocyclyl)₂, —NHC(O)(C₁₋₉ alkyl), —NHC(O)(C₂₋₆ alkenyl), —NHC(O)(C₂₋₆ alkynyl), —NHC(O)(C₃₋₁₅ cycloalkyl), —NHC(O)(C₁₋₈ haloalkyl), —NHC(O)(aryl), —NHC(O)(heteroaryl), —NHC(O)(heterocyclyl), —NHC(O)O(C₁₋₉ alkyl), —NHC(O)O(C₂₋₆ alkenyl), —NHC(O)O(C₂₋₆ alkynyl), —NHC(O)O(C₃₋₁₅ cycloalkyl), —NHC(O)O(C₁₋₈ haloalkyl), —NHC(O)O(aryl), —NHC(O)O(heteroaryl), —NHC(O)O(heterocyclyl), —NHC(O)NH(C₁₋₉ alkyl), —NHC(O)NH(C₂₋₆ alkenyl), —NHC(O)NH(C₂₋₆ alkynyl), —NHC(O)NH(C₃₋₁₅ cycloalkyl), —NHC(O)NH(C₁₋₈ haloalkyl), —NHC(O)NH(aryl), —NHC(O)NH(heteroaryl), —NHC(O)NH(heterocyclyl), —SH, —S(C₁₋₉ alkyl), —S(C₂₋₆ alkenyl), —S(C₂₋₆ alkynyl), —S(C₃₋₁₅ cycloalkyl), —S(C₁₋₈ haloalkyl), —S(aryl), —S(heteroaryl), —S(heterocyclyl), —NHS(O)(C₁₋₉ alkyl), —N(C₁₋₉ alkyl)(S(O)(C₁₋₉ alkyl), —S(O)N(C₁₋₉ alkyl)₂, —S(O)(C₁₋₉ alkyl), —S(O)(NH)(C₁₋₉ alkyl), —S(O)(C₂₋₆ alkenyl), —S(O)(C₂₋₆ alkynyl), —S(O)(C₃₋₁₅ cycloalkyl), —S(O)(C₁₋₈ haloalkyl), —S(O)(aryl), —S(O)(heteroaryl), —S(O)(heterocyclyl), —S(O)₂(C₁₋₉ alkyl), —S(O)₂(C₂₋₆ alkenyl), —S(O)₂(C₂₋₆ alkynyl), —S(O)₂(C₃₋₁₅ cycloalkyl), —S(O)₂(C₁₋₈ haloalkyl), —S(O)₂(aryl), —S(O)₂(heteroaryl), —S(O)₂(heterocyclyl), —S(O)₂NH(C₁₋₉ alkyl), or —S(O)₂N(C₁₋₉ alkyl)₂;

wherein any alkyl, cycloalkyl, aryl, heteroaryl, or heterocyclyl is optionally substituted with one to four halo, C₁₋₉ alkyl, C₁₋₈ haloalkyl, —OH, —NH₂, —NH(C₁₋₉ alkyl), —NH(C₃₋₁₅ cycloalkyl), —NH(C₁₋₈ haloalkyl), —NH(aryl), —NH(heteroaryl), —NH(heterocyclyl), —N(C₁₋₉ alkyl)₂, —N(C₃₋₁₅ cycloalkyl)₂, —NHC(O)(C₃₋₁₅ cycloalkyl), —NHC(O)(C₁₋₈ haloalkyl), —NHC(O)(aryl), —NHC(O)(heteroaryl), —NHC(O)(heterocyclyl), —NHC(O)O(C₁₋₉ alkyl), —NHC(O)O(C₂₋₆ alkynyl), —NHC(O)O(C₃₋₁₅ cycloalkyl), —NHC(O)O(C₁₋₈ haloalkyl), —NHC(O)O(aryl), —NHC(O)O(heteroaryl), —NHC(O)O(heterocyclyl), —NHC(O)NH(C₁₋₉ alkyl), —S(O)(NH)(C₁₋₉ alkyl), S(O)₂(C₁₋₉ alkyl), —S(O)₂(C₃₋₁₅ cycloalkyl), —S(O)₂(C₁₋₈ haloalkyl), —S(O)₂(aryl), —S(O)₂(heteroaryl), —S(O)₂(heterocyclyl), —S(O)₂NH(C₁₋₉ alkyl), —S(O)₂N(C₁₋₉ alkyl)₂, —O(C₃₋₁₅ cycloalkyl), —O(C₁₋₅ haloalkyl), —O(aryl), —O(heteroaryl), —O(heterocyclyl), or —O(C₁₋₉ alkyl);

m is 0, 1, or 2;

or a pharmaceutically acceptable salt, stereoisomer, mixture of stereoisomers, or deuterated analog thereof.

In certain embodiments, R² is hydrogen.

Also provided herein are compounds of Formula II:

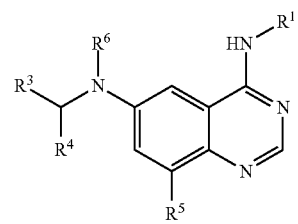

II wherein R¹, R³, R⁴, R⁵ and R⁶ are as defined herein.

Also provided herein are compounds of Formula IIA:

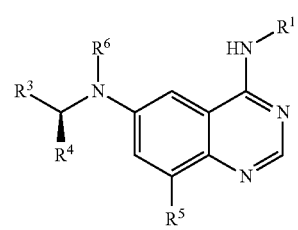

IIA wherein R¹, R³, R⁴, R⁵ and R⁶ are as defined herein.

Also provided herein are compounds of Formula III:

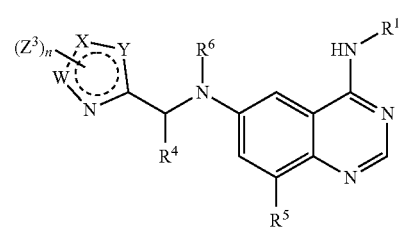

III wherein R¹, R⁴, R⁵ and R⁶ are as defined in herein,

W, X and Y are each independently N or C;

n is 1, 2, or 3;

each Z³ is independently hydrogen, oxo, halo, —NO₂, —N₃, cyano, thioxo, C₁₋₉ alkyl, C₂₋₆ alkenyl, C₂₋₆ alkynyl, C₃₋₁₅ cycloalkyl, C₁₋₈ haloalkyl, aryl, heteroaryl, heterocyclyl, —O—R$^{12}$, —C(O)—R$^{12}$, —C(O)O—R$^{12}$, —C(O)—N(R$^{13}$)(R$^{14}$), —N(R$^{13}$)(R$^{14}$), N(R$^{13}$)$_2$(R$^{14}$)$^+$, —N(R$^{13}$)$_2$(R$^{12}$)C(O)—R$^{12}$, —N(R$^{12}$)C(O)O—R$^{12}$, —N(R$^{12}$)C(O)N(R$^{13}$)(R$^{14}$), —N(R$^{12}$)S(O)$_2$(R$^{12}$), —NR$^{12}$S(O)$_2$N(R$^{13}$)(R$^{14}$), —NR$^{12}$S(O)$_2$O(R$^{12}$), —OC(O)R$^{12}$, —OC(O)—N(R$^{13}$)(R$^{14}$), —P(O)(OR$^{12}$)$_2$, —OP(O)(OR$^{12}$)$_2$, —CH$_2$P(O)(R$^{12}$)$_2$, —OCH$_2$P(O)(OR$^{12}$)$_2$, —C(O)OCH$_2$P(O)(OR$^{12}$)$_2$, —P(O)(R$^{12}$)(OR$^{12}$), —OP(O)(R$^{12}$)(OR$^{12}$), —CH$_2$P(O)(R$^{12}$)(OR$^{12}$), —OCH$_2$P(O)(R$^{12}$)(OR$^{12}$), —C(O)OCH$_2$P(O)(R$^{12}$)(OR$^{12}$), —P(O)(N(R$^{12}$)$_2$)$_2$, —OP(O)(N(R$^{12}$)$_2$)$_2$, —CH$_2$P(O)(N(R$^{12}$)$_2$)$_2$, —OCH$_2$P(O)(N(R$^{12}$)$_2$)$_2$, —C(O)OCH$_2$P((O)(N(R$^{12}$)$_2$)$_2$, —P(O)(N(R$^{12}$)$_2$)(OR$^{12}$), —OP(O)(N(R$^{12}$)$_2$)(OR$^{12}$), —CH$_2$P(O)(N(R$^{12}$)$_2$)(OR$^{12}$), —OCH$_2$P(O)(N(R$^{12}$)$_2$)(OR$^{12}$), —C(O)OCH$_2$P(O)(N(R$^{12}$)$_2$)(OR$^{12}$), —P(O)(R$^{12}$)(N(R$^{12}$)$_2$), —OP(O)(R$^{12}$)(N(R$^{12}$)$_2$), —CH$_2$P(O)(R$^{12}$)(N(R$^{12}$)$_2$), —OCH$_2$P(O)(R$^{12}$)(N(R$^{12}$)$_2$), —C(O)OCH$_2$P(O)(R$^{12}$)(N(R$^{12}$)$_2$), —Si(R$^{12}$)$_3$, —S—R$^{12}$, —S(O)R$^{12}$, —S(O)(NH)R$^{12}$, —S(O)$_2$R$^2$ or —S(O)$_2$N(R$^{13}$)(R$^{14}$);

wherein any alkyl, alkenyl, alkynyl, cycloalkyl, haloalkyl, aryl, heteroaryl or heterocyclyl is optionally substituted with one to four Z$^{1a}$ groups;

each Z$^{1a}$ is independently oxo, halo, thioxo, —NO$_2$, cyano, —N$_3$, C$_{1-9}$ alkyl, C$_{2-6}$ alkenyl, C$_{2-6}$ alkynyl, C$_{3-15}$ cycloalkyl, C$_{1-8}$ haloalkyl, aryl, heteroaryl, heterocyclyl, —O—R$^{12}$, —C(O)R$^{12}$, —C(O)O—R$^{12}$, —C(O)N(R$^{13}$)(R$^{14}$), —N(R$^{13}$)(R$^{14}$), —N(R$^{13}$)$_2$(R$^{14}$)$^+$, —N(R$^{12}$)—C(O)R$^{12}$, —N(R$^{12}$)C(O)O(R$^{12}$), —N(R$^{12}$)C(O)N(R$^{13}$)(R$^{14}$), —N(R$^{12}$)S(O)$_2$(R$^{12}$), —N(R$^{12}$)S(O)$_2$—N(R$^{13}$)(R$^{14}$), —N(R$^{12}$)S(O)$_2$O(R$^{12}$), —OC(O)R, —OC(O)OR$^{12}$, —OC(O)—N(R$^{13}$)(R$^{14}$), —Si(R$^{12}$)$_3$, —S—R$^{12}$, —S(O)R$^{12}$, —S(O)(NH)R$^{12}$, —S(O)$_2$R$^{12}$ or —S(O)$_2$N(R$^{13}$)(R$^{14}$);

wherein any alkenyl, alkynyl, cycloalkyl, aryl, heteroaryl or heterocyclyl is optionally substituted with one to four Z$^{1b}$ groups;

each R$^{12}$ is independently hydrogen, C$_{1-9}$ alkyl, C$_{2-6}$ alkenyl, C$_{2-6}$ alkynyl, C$_{3-15}$ cycloalkyl, aryl, heteroaryl or heterocyclyl;

wherein any alkyl, alkenyl, alkynyl, cycloalkyl, aryl, heteroaryl or heterocyclyl is optionally substituted with one to four Z$^{1b}$ groups;

R$^{13}$ and R$^{14}$ at each occurrence are each independently hydrogen, C$_{1-9}$ alkyl, C$_{2-6}$ alkenyl, C$_{2-6}$ alkynyl, C$_{3-15}$ cycloalkyl, aryl, heteroaryl or heterocyclyl;

wherein any alkyl, alkenyl, alkynyl, cycloalkyl, aryl, heteroaryl or heterocyclyl is optionally substituted with one to four Z$^{1b}$ groups, or R$^{13}$ and R$^{14}$ together with the nitrogen to which they are attached form a heterocyclyl, wherein said heterocyclyl is optionally substituted with one to four Z$^{1b}$ groups; and each Z$^{1b}$ is independently oxo, thioxo, hydroxy, halo, —NO$_2$, —N$_3$, cyano, C$_{1-9}$ alkyl, C$_{2-6}$ alkenyl, C$_{2-6}$ alkynyl, C$_{3-15}$ cycloalkyl, C$_{1-8}$ haloalkyl, aryl, heteroaryl, heterocyclyl, —O(C$_{1-9}$ alkyl), —O(C$_{2-6}$ alkenyl), —O(C$_{2-6}$ alkynyl), —O(C$_{3-15}$ cycloalkyl), —O(C$_{1-8}$ haloalkyl), —O(aryl), —O(heteroaryl), —O(heterocyclyl), —NH$_2$, —NH(C$_{1-9}$ alkyl), —NH(C$_{2-6}$ alkenyl), —NH(C$_{2-6}$ alkynyl), —NH(C$_{3-15}$ cycloalkyl), —NH(C$_{1-8}$ haloalkyl), —NH(aryl), —NH(heteroaryl), —NH(heterocyclyl), —N(C$_{1-9}$ alkyl)$_2$, —N(C$_{3-15}$ cycloalkyl)$_2$, —N(C$_{2-6}$ alkenyl)$_2$, —N(C$_{2-6}$ alkynyl)$_2$, —N(C$_{3-15}$ cycloalkyl)$_2$, —N(C$_{1-8}$ haloalkyl)$_2$, —N(aryl)$_2$, —N(heteroaryl)$_2$, —N(heterocyclyl)$_2$, —N(C$_{1-9}$ alkyl)(C$_{3-15}$ cycloalkyl), —N(C$_{1-9}$ alkyl)(C$_{2-6}$ alkenyl), —N(C$_{1-9}$ alkyl)(C$_{2-6}$ alkynyl), —N(C$_{1-9}$ alkyl)(C$_{3-15}$ cycloalkyl), —N(C$_{1-9}$ alkyl)(C$_{1-8}$ haloalkyl), —N(C$_{1-9}$ alkyl)(aryl), —N(C$_{1-9}$ alkyl)(heteroaryl), —N(C$_{1-9}$ alkyl)(heterocyclyl), —C(O)(C$_{1-9}$ alkyl), —C(O)(C$_{2-6}$ alkenyl), —C(O)(C$_{2-6}$ alkynyl), —C(O)(C$_{3-15}$ cycloalkyl), —C(O)(C$_{1-8}$ haloalkyl), —C(O)(aryl), —C(O)(heteroaryl), —C(O)(heterocyclyl), —C(O)O(C$_{1-9}$ alkyl), —C(O)O(C$_{2-6}$ alkenyl), —C(O)O(C$_{2-6}$ alkynyl), —C(O)O(C$_{3-15}$ cycloalkyl), —C(O)O(C$_{1-8}$ haloalkyl), —C(O)O(aryl), —C(O)O(heteroaryl), —C(O)O(heterocyclyl), —C(O)NH$_2$, —C(O)NH(C$_{1-9}$ alkyl), —C(O)NH(C$_{2-6}$ alkenyl), —C(O)NH(C$_{2-6}$ alkynyl), —C(O)NH(C$_{3-15}$ cycloalkyl), —C(O)NH(C$_{1-8}$ haloalkyl), —C(O)NH(aryl), —C(O)NH(heteroaryl), —C(O)NH(heterocyclyl), —C(O)N(C$_{1-9}$ alkyl)$_2$, —C(O)N(C$_{3-15}$ cycloalkyl)$_2$, —C(O)N(C$_{2-6}$ alkenyl)$_2$, —C(O)N(C$_{2-6}$ alkynyl)$_2$, —C(O)N(C$_{3-15}$ cycloalkyl)$_2$, —C(O)N(C$_{1-8}$ haloalkyl)$_2$, —C(O)N(aryl)$_2$, —C(O)N(heteroaryl)$_2$, —C(O)N(heterocyclyl)$_2$, —NHC(O)(C$_{1-9}$ alkyl), —NHC(O)(C$_{2-6}$ alkenyl), —NHC(O)(C$_{2-6}$ alkynyl), —NHC(O)(C$_{3-15}$ cycloalkyl), —NHC(O)(C$_{1-8}$ haloalkyl), —NHC(O)(aryl), —NHC(O)(heteroaryl), —NHC(O)(heterocyclyl), —NHC(O)O(C$_{1-9}$ alkyl), —NHC(O)O(C$_{2-6}$ alkenyl), —NHC(O)O(C$_{2-6}$ alkynyl), —NHC(O)O(C$_{3-15}$ cycloalkyl), —NHC(O)O(C$_{1-8}$ haloalkyl), —NHC(O)O(aryl), —NHC(O)O(heteroaryl), —NHC(O)O(heterocyclyl), —NHC(O)NH(C$_{1-9}$ alkyl), —NHC(O)NH(C$_{2-6}$ alkenyl), —NHC(O)NH(C$_{2-6}$ alkynyl), —NHC(O)NH(C$_{3-15}$ cycloalkyl), —NHC(O)NH(C$_{1-8}$ haloalkyl), —NHC(O)NH(aryl), —NHC(O)NH(heteroaryl), —NHC(O)NH(heterocyclyl), —SH, —S(C$_{1-9}$ alkyl), —S(C$_{2-6}$ alkenyl), —S(C$_{2-6}$ alkynyl), —S(C$_{3-15}$ cycloalkyl), —S(C$_{1-8}$ haloalkyl), —S(aryl), —S(heteroaryl), —S(heterocyclyl), —NHS(O)(C$_{1-9}$ alkyl), —N(C$_{1-9}$ alkyl)(S(O)(C$_{1-9}$ alkyl), —S(O)N(C$_{1-9}$ alkyl)$_2$, —S(O)(C$_{1-9}$ alkyl), —S(O)(NH)(C$_{1-9}$ alkyl), —S(O)(C$_{2-6}$ alkenyl), —S(O)(C$_{2-6}$ alkynyl), —S(O)(C$_{3-15}$ cycloalkyl), —S(O)(C$_{1-8}$ haloalkyl), —S(O)(aryl), —S(O)(heteroaryl), —S(O)(heterocyclyl), —S(O)$_2$(C$_{1-9}$ alkyl), —S(O)$_2$(C$_{2-6}$ alkenyl), —S(O)$_2$(C$_{2-6}$ alkynyl), —S(O)$_2$(C$_{3-15}$ cycloalkyl), —S(O)$_2$(C$_{1-8}$ haloalkyl), —S(O)$_2$(aryl), —S(O)$_2$(heteroaryl), —S(O)$_2$(heterocyclyl), —S(O)$_2$NH(C$_{1-9}$ alkyl), or —S(O)$_2$N(C$_{1-9}$ alkyl)$_2$;

wherein any alkyl, cycloalkyl, aryl, heteroaryl, or heterocyclyl is optionally substituted with one to four halo, C$_{1-9}$ alkyl, C$_{1-8}$ haloalkyl, —OH, —NH$_2$, —NH(C$_{1-9}$ alkyl), —NH(C$_{3-15}$ cycloalkyl), —NH(C$_{1-8}$ haloalkyl), —NH(aryl), —NH(heteroaryl), —NH(heterocyclyl), —N(C$_{1-9}$ alkyl)$_2$, —N(C$_{3-15}$ cycloalkyl)$_2$, —NHC(O)(C$_{3-15}$ cycloalkyl), —NHC(O)(C$_{1-8}$ haloalkyl), —NHC(O)(aryl), —NHC(O)(heteroaryl), —NHC(O)(heterocyclyl), —NHC(O)O(C$_{1-9}$ alkyl), —NHC(O)O(C$_{2-6}$ alkynyl), —NHC(O)O(C$_{3-15}$ cycloalkyl), —NHC(O)O(C$_{1-8}$ haloalkyl), —NHC(O)O(aryl), —NHC(O)O(heteroaryl), —NHC(O)O(heterocyclyl), —NHC(O)NH(C$_{1-9}$ alkyl), —S(O)(NH)(C$_{1-9}$ alkyl), S(O)$_2$(C$_{1-9}$ alkyl), —S(O)$_2$(C$_{3-15}$ cycloalkyl), —S(O)$_2$(C$_{1-8}$ haloalkyl), —S(O)$_2$(aryl), —S(O)$_2$(heteroaryl), —S(O)$_2$(heterocyclyl), —S(O)$_2$NH(C$_{1-9}$ alkyl), —S(O)$_2$N(C$_{1-9}$ alkyl)$_2$, —O(C$_{3-15}$ cycloalkyl), —O(C$_{1-8}$ haloalkyl), —O(aryl), —O(heteroaryl), —O(heterocyclyl), or —O(C$_{1-9}$ alkyl);

or a pharmaceutically acceptable salt, stereoisomer, mixture of stereoisomers, or deuterated analog thereof.

Also provided herein are compounds of Formula IIIA:

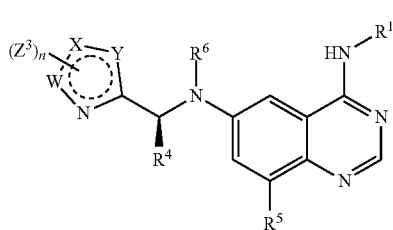

IIIA wherein W, X, Y, $Z^3$, n, $R^1$, $R^4$, $R^5$ and $R^6$ are as defined in herein.

In certain embodiments, W is N, X is N—$Z^3$, and Y is C—$Z^3$. In certain embodiments, W is C—$Z^3$, X is N—$Z^3$, and Y is C—$Z^3$.

In certain embodiments, the compound of Formula I is represented by Formula IV or V:

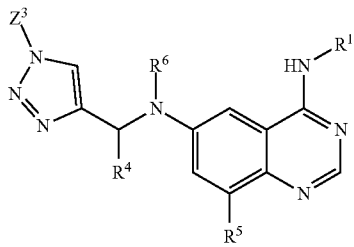

IV

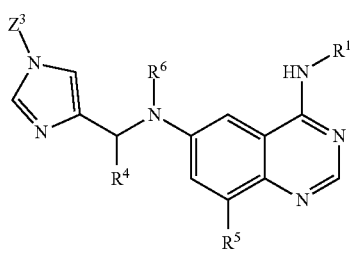

V wherein $Z^3$, $R^1$, $R^4$, $R^5$ and $R^6$ are as defined herein.

In certain embodiments, the compound of Formula I is represented by Formula IVA or VA:

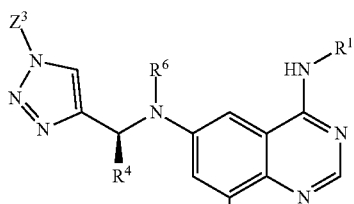

IVA

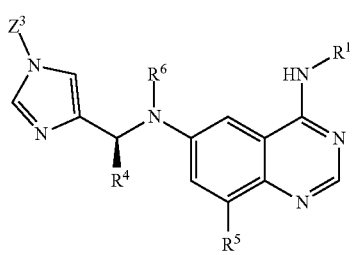

VA wherein $Z^3$, $R^1$, $R^4$, $R^5$ and $R^6$ are as defined herein.

In certain embodiments, the compound of Formula I is represented by Formula VI:

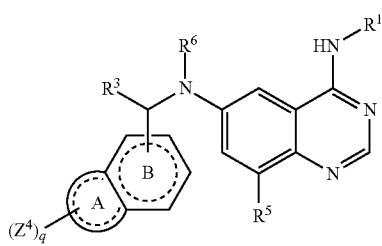

VI wherein $R^1$, $R^3$, $R^5$, $R^6$ and $Z^4$ are as defined herein, q is 0, 1, 2, 3 or 4, ring A is a 5- or 6-membered cycloalkyl, heterocyclyl or heteroaryl ring, and ring B is a 6-membered cycloalkyl, heterocyclyl or heteroaryl ring, provided that at least one heteroatom is present in ring A or ring B such that $R^4$ is an optionally substituted bicyclic heterocyclyl or optionally substituted bicyclic heteroaryl. In the above, the wavy line indicates the point of attachment to the remainder of the molecule, where the attachment can through either ring (i.e., ring A or ring B) of the optionally substituted bicyclic heterocyclyl or optionally substituted bicyclic heteroaryl. In some embodiments, ring A and/or ring B comprises an oxo (=O).

In certain embodiments, provided is a compound of Formula VIA:

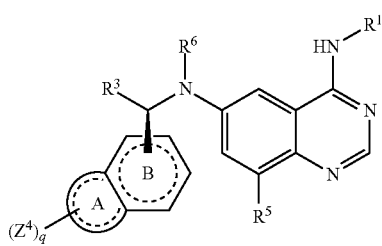

VIA wherein $R^1$, $R^3$, $R^5$, $R^6$, $Z^4$, q, ring A and ring B are as defined herein.

In certain embodiments, provided is a compound of Formula VII:

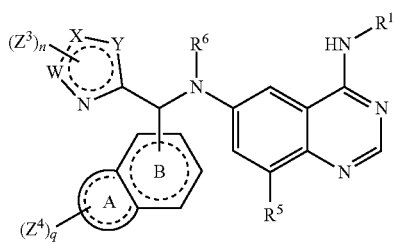

VII wherein W, X, Y, $R^1$, $R^5$, $R^6$, $Z^3$, $Z^4$, q, n, ring A and ring B are as defined herein.

In certain embodiments, provided is a compound of Formula VIIA:

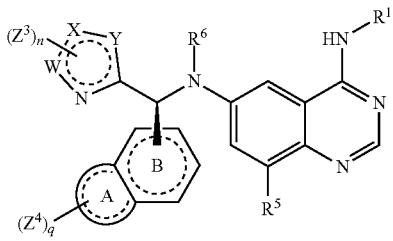

VIIA wherein W, X, Y, $R^1$, $R^5$, $R^6$, $Z^3$, $Z^4$, q, n, ring A and ring B are as defined herein.

In certain embodiments, the compound of Formula I is represented by Formula VIII:

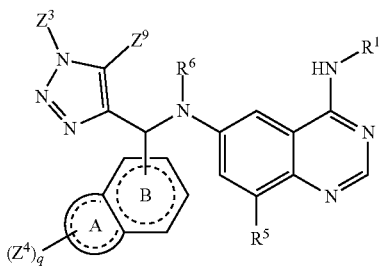

VIII wherein $R^1$, $R^5$, $R^6$, $Z^3$, $Z^4$, q, n, ring A and ring B are as defined herein and $Z^9$ is hydrogen, halo, —CN, or —O—$R^{12}$.

In certain embodiments, the compound of Formula I is represented by Formula VIIIA:

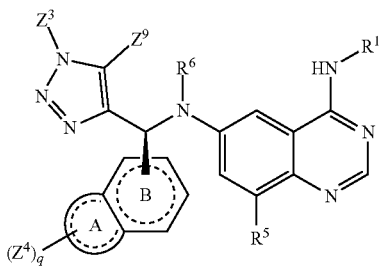

VIIIA wherein $R^1$, $R^5$, $R^6$, $Z^3$, $Z^4$, q, n, ring A and ring B are as defined herein and $Z^9$ is hydrogen, halo, —CN, or —O—$R^{12}$.

In certain embodiments, the compound of Formula I is represented by Formula IX:

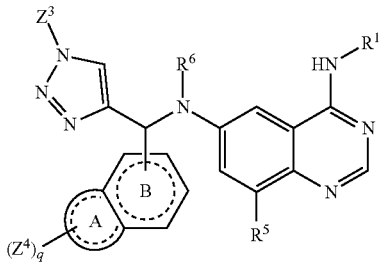

IX wherein $R^1$, $R^5$, $R^6$, $Z^3$, $Z^4$, q, n, ring A and ring B are as defined herein.

In certain embodiments, the compound of Formula I is represented by Formula IXA:

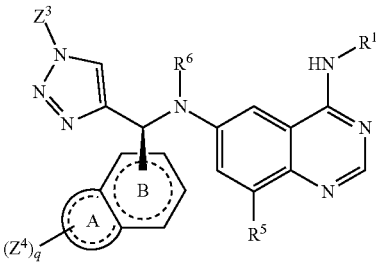

IXA wherein $R^1$, $R^5$, $R^6$, $Z^3$, $Z^4$, q, n, ring A and ring B are as defined herein.

In certain embodiments, $Z^3$ is hydrogen, $C_{1-9}$ alkyl, $C_{3-15}$ cycloalkyl, heterocyclyl, aryl, or heteroaryl;
wherein said $C_{1-9}$ alkyl, $C_{3-15}$ cycloalkyl, heterocyclyl, aryl, or heteroaryl, may be optionally substituted with one to four substituents independently selected from the group consisting of cyano, halo, —O—$R^{12}$, —C(O)—$R^{12}$, —OC(O)—$R^{12}$, —C(O)O—$R^{12}$, —C(O)—N($R^{13}$)($R^{14}$), —N($R^{13}$)($R^{14}$), —N($R^{13}$)$_2$($R^{14}$)$^+$, —S(O)$_2$—$R^{12}$, —Si($R^{12}$)$_3$, $C_{1-9}$ alkyl, $C_{1-9}$ haloalkyl, $C_{3-15}$ cycloalkyl, aryl, heterocyclyl, and heteroaryl; and
wherein said $C_{1-9}$ alkyl, $C_{3-15}$ cycloalkyl, heterocyclyl, or aryl may be optionally substituted with one to three substituents independently selected from the group consisting of halo, —O($C_{1-9}$ alkyl), —C(O)N($C_{1-9}$ alkyl)$_2$, $C_{1-9}$ alkyl, and heterocyclyl.

In certain embodiments, $Z^3$ is hydrogen or $C_{1-9}$ alkyl;
wherein said $C_{1-9}$ alkyl may be optionally substituted with one to four substituents independently selected from the group consisting of cyano, halo, —O—$R^{12}$, —C(O)—$R^{12}$, —OC(O)—$R^{12}$, —C(O)O—$R^{12}$, —C(O)—N($R^{13}$)($R^{14}$), —N($R^{13}$)($R^{14}$), —N($R^{13}$)$_2$($R^{14}$)$^+$, —S(O)$_2$—$R^{12}$, —Si($R^{12}$)$_3$, $C_{1-9}$ haloalkyl, $C_{3-15}$ cycloalkyl, aryl, heterocyclyl, and heteroaryl; and
wherein said $C_{3-15}$ cycloalkyl, aryl, heterocyclyl, and heteroaryl may be optionally substituted with one to three substituents independently selected from the group consisting of halo, —O($C_{1-9}$ alkyl), —C(O)N($C_{1-9}$ alkyl)$_2$, $C_{1-9}$ alkyl, and heterocyclyl.

In certain embodiments, $Z^3$ is hydrogen or $C_{1-9}$ alkyl optionally substituted with one to four substituents independently selected from the group consisting of cyano, halo, —O—$R^{12}$, —C(O)O—$R^{12}$, —OC(O)—$R^{12}$, —N($R^{13}$)($R^{14}$), —N($R^{13}$)$_2$($R^{14}$)$^+$, $C_{1-9}$ haloalkyl, heterocyclyl, and heteroaryl.

In certain embodiments, $Z^3$ is $C_{3-15}$ cycloalkyl, heterocyclyl, aryl, or heteroaryl;
wherein said $C_{3-15}$ cycloalkyl, heterocyclyl, aryl, or heteroaryl, may be optionally substituted with one to four substituents independently selected from the group consisting of cyano, halo, —O—$R^{12}$, —C(O)—$R^{12}$, —OC(O)—$R^{12}$, —C(O)O—$R^{12}$, —C(O)—N($R^{13}$)($R^{14}$), —N($R^{13}$)($R^{14}$), —N($R^{13}$)$_2$($R^{14}$)$^+$, —S(O)$_2$—$R^{12}$, —Si($R^{12}$)$_3$, $C_{1-9}$ alkyl, $C_{1-9}$ haloalkyl, $C_{3-15}$ cycloalkyl, aryl, heterocyclyl, and heteroaryl; and
wherein said $C_{1-9}$ alkyl, $C_{3-15}$ cycloalkyl, aryl, heterocyclyl, and heteroaryl may be optionally substituted with one to three substituents independently selected from the group consisting of halo, —O(C$_{1-9}$ alkyl), —C(O)N(C$_{1-9}$ alkyl)$_2$, C$_{1-9}$ alkyl, and heterocyclyl.

In certain embodiments, wherein Z$^3$ is C$_{3-15}$ cycloalkyl optionally substituted with one to four substituents independently selected from the group consisting of cyano, halo, —O—R$^{12}$, —C(O)O—R$^{12}$, —OC(O)—R$^{12}$, —N(R$^{13}$)(R$^{14}$), —N(R$^{13}$)$_2$(R$^{14}$)$^+$, C$_{1-9}$ alkyl, C$_{1-9}$ haloalkyl, heterocyclyl, and heteroaryl.

In certain embodiments, Z$^3$ is hydrogen, C$_{1-9}$ alkyl, C$_{3-15}$ cycloalkyl, heterocyclyl, aryl, or heteroaryl;
   wherein said C$_{1-9}$ alkyl, C$_{3-15}$ cycloalkyl, heterocyclyl, aryl, or heteroaryl may be optionally substituted with one to four substituents independently selected from the group consisting of cyano, halo, —O—R$^{12}$, —C(O)—R$^{12}$, —OC(O)—R$^{12}$, —C(O)O—R$^{12}$, —C(O)—N(R$^{13}$)(R$^{14}$), —N(R$^{13}$)(R$^{14}$), —N(R$^{13}$)$_2$(R$^{14}$)$^+$, —S(O)$_2$—R$^{12}$, —Si(R$^{12}$)$_3$, C$_{1-9}$ alkyl, C$_{1-9}$ haloalkyl, C$_{3-15}$ cycloalkyl, aryl, heterocyclyl, and heteroaryl;
      wherein said C$_{1-9}$ alkyl, C$_{3-15}$ cycloalkyl, aryl, heterocyclyl, and heteroaryl may be optionally substituted with one to three substituents independently selected from the group consisting of halo, —O(C$_{1-9}$ alkyl), —C(O)—N(C$_{1-9}$ alkyl)$_2$, C$_{1-9}$ alkyl, and heterocyclyl;

R$^1$ is C$_{1-9}$ alkyl;
   wherein said C$_{1-9}$ alkyl may be optionally substituted with one to three substituents independently selected from the group consisting of cyano, halo, —O—R$^{12}$, —N(R$^{13}$)(R$^{14}$), —N(R$^{12}$)C(O)O—R$^{12}$, —S(O)$_2$—R$^{12}$, —Si(R$^{12}$)$_3$, C$_{1-9}$ alkyl, C$_{3-5}$ cycloalkyl, heterocyclyl, aryl, and heteroaryl;
      wherein said C$_{1-9}$ alkyl, C$_{3-15}$ cycloalkyl, aryl, or heteroaryl may be optionally substituted with one to three substituents independently selected from the group consisting of cyano, halo, —O—R$^{12}$, —N(R$^{13}$)(R$^{14}$), C$_{1-9}$ alkyl, C$_{3-15}$ cycloalkyl, and aryl;

R$^4$ is aryl, heterocyclyl, or heteroaryl;
   wherein said aryl, heterocyclyl, or heteroaryl is optionally substituted with one to three substituents independently selected from the group consisting of cyano, halo, —O—R$^{12}$, —C(O)—R$^{12}$, —C(O)O—R$^{12}$, —S(O)$_2$—R$^{12}$, —N(R$^{12}$)C(O)—R$^{12}$, —N(R$^{12}$)S(O)$_2$R$^{12}$, —C(O)N(R$^{13}$)(R$^{14}$), —N(R$^{13}$)(R$^{14}$), C$_{1-9}$ alkyl, heterocyclyl, aryl, and heteroaryl;
      wherein said C$_{1-9}$ alkyl, or heteroaryl may be optionally substituted with one to three substituents independently selected from the group consisting of halo, —O—R$^{12}$, —N(R$^{13}$)(R$^{14}$), C$_{1-9}$ alkyl, and heterocyclyl;

R$^5$ is cyano, halo, —O—R$^7$, —C(O)R$^7$, —N(R$^8$)C(O)(R$^7$), —C(O)N(R$^8$)(R$^9$), C$_{1-9}$ alkyl, C$_{2-6}$ alkynyl, C$_{3-15}$ cycloalkyl, aryl, or heteroaryl;
   wherein said C$_{1-9}$ alkyl, aryl, or heteroaryl may be optionally substituted with one to three substituents independently selected from the group consisting of halo, —O—R$^{12}$, and C$_{1-9}$ alkyl;

each R$^7$ is independently hydrogen, C$_{1-9}$ alkyl, C$_{3-15}$ cycloalkyl, heterocyclyl, or aryl;
   wherein said C$_{1-9}$ alkyl, C$_{3-15}$ cycloalkyl, heterocyclyl, or aryl may be optionally substituted with one to three substituents independently selected from the group consisting of halo, —O—R$^{12}$, —N(R$^{13}$)(R$^{14}$), C$_{1-9}$ alkyl, aryl, and heteroaryl;

each R$^{12}$ is independently hydrogen, C$_{1-9}$ alkyl, C$_{3-15}$ cycloalkyl, heterocyclyl, or aryl;
   wherein said C$_{1-9}$ alkyl, C$_{3-15}$ cycloalkyl, heterocyclyl, or aryl may be optionally substituted with one to three substituents independently selected from the group consisting of halo, hydroxy, —O(C$_{1-9}$ alkyl), —N(C$_{1-9}$ alkyl)$_2$, C$_{1-9}$ alkyl, aryl, and heteroaryl; and each R$^{13}$ and R$^{14}$ are independently hydrogen, C$_{1-9}$ alkyl, C$_{3-15}$ cycloalkyl, heterocyclyl, or aryl;
   wherein said C$_{1-9}$ alkyl, C$_{3-15}$ cycloalkyl, heterocyclyl, or aryl may be optionally substituted with one to three substituents independently selected from the group consisting of halo, hydroxy, —O(C$_{1-9}$ alkyl), —N(C$_{1-9}$ alkyl)$_2$, C$_{1-9}$ alkyl, aryl, and heteroaryl.

In certain embodiments, Z$^3$ is cyclopropyl optionally substituted with C$_{1-9}$ haloalkyl.

In certain embodiments, Z$^3$ is cyclopropyl, 1-(fluoromethyl)cyclopropyl, 1-(difluoromethyl)cyclopropyl, 1-(trifluoromethyl)cyclopropyl, 1-cyanocyclopropyl, bicyclo[1.1.1]pentan-1-yl, or carboxymethyl.

In certain embodiments, R$^1$ is C$_{1-9}$ alkyl optionally substituted with one to four substituents independently selected the group consisting of cyano, aryl and heterocyclyl. In one embodiment, R$^1$ is C$_{1-9}$ alkyl optionally substituted with one to two substituents independently selected the group consisting of cyano, phenyl and tetrahydro-2H-pyran. In another embodiment, R$^1$ is 2,2-dimethylpropyl, (4-methyltetrahydro-2H-pyran-4-yl)methyl, or 3-cyano-1-phenylpropyl.

In certain embodiments, R$^4$ is optionally substituted bicyclic heterocyclyl or optionally substituted bicyclic heteroaryl. In certain embodiments, R$^4$ is

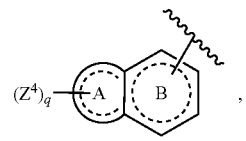

where Z$^4$ is as defined herein, q is 0, 1, 2, 3 or 4, ring A is a 5- or 6-membered cycloalkyl, heterocyclyl or heteroaryl ring, and ring B is a 6-membered cycloalkyl, heterocyclyl or heteroaryl ring, provided that at least one heteroatom is present in ring A or ring B such that R$^4$ is an optionally substituted bicyclic heterocyclyl or optionally substituted bicyclic heteroaryl. In the above, the wavy line indicates the point of attachment to the remainder of the molecule, where the attachment can through either ring (i.e., ring A or ring B) of the optionally substituted bicyclic heterocyclyl or optionally substituted bicyclic heteroaryl. In some embodiments, ring A and/or ring B comprises an oxo (=O).

In certain embodiments, R$^4$ is optionally substituted bicyclic heteroaryl. In certain embodiments, R$^4$ is an optionally substituted bicyclic heteroaryl selected from the group consisting of

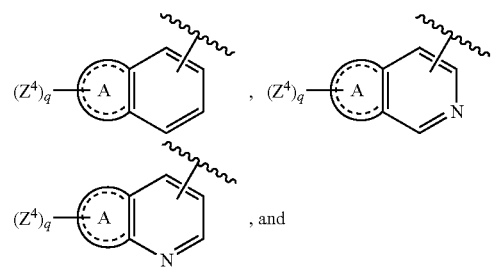

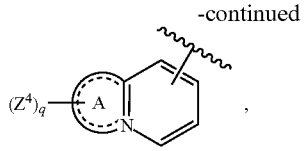

where $Z^4$ is as defined herein, q is 0, 1, 2, 3 or 4 and ring A is a 5- or 6-membered heterocyclyl or heteroaryl ring. In some embodiments, ring A comprises an oxo (=O).

In certain embodiments, $R^4$ is optionally substituted monocyclic heteroaryl. In certain embodiments, $R^4$ is

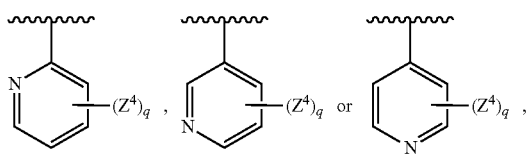

where $Z^4$ is as defined herein and q is 0, 1, 2, 3 or 4.

In certain embodiments, $R^4$ is optionally substituted monocyclic heteroaryl. In certain embodiments, $R^4$ is

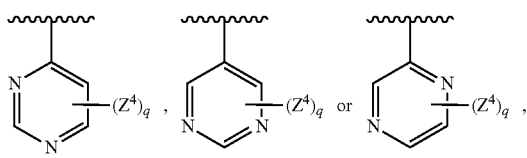

where $Z^4$ is as defined herein and q is 0, 1, 2, 3 or 4.

In certain embodiments, $R^4$ is aryl or heteroaryl, wherein said aryl or heteroaryl may be optionally substituted with one to three substituents independently selected from the group consisting of cyano, halo and $C_{1-9}$ alkyl. In one embodiment, $R^4$ is 6-fluoro-2-methylpyridin-3-yl, 2-chlorophenyl, 4-fluorophenyl, 3-cyanophenyl, 6-fluoro-2-methylpyridin-3-yl, 2-methyl-1-oxo-1,2-dihydroisoquinolin-5-yl, or benzo[d]thiazol-7-yl.

In certain embodiments, $R^5$ is hydrogen, cyano, or halo. In one embodiment, $R^5$ is hydrogen, cyano, chloro, or bromo.

In certain embodiments, $R^6$ is hydrogen or $C_{1-9}$ alkyl. In one embodiment, $R^6$ is hydrogen or ethyl. In certain embodiments, $R^6$ is hydrogen.

In general, the specific compounds exemplified herein are named using ChemBioDraw Ultra. However, it is understood that other names may be used to identify compounds of the same structure. In particular, the compounds may also be named using other nomenclature systems and symbols that are commonly recognized in the art of chemistry including, for example, Chemical Abstract Service (CAS) and International Union of Pure and Applied Chemistry (IUPAC). Other compounds or radicals may be named with common names, or systematic or non-systematic names.

In certain embodiments, provided are optical isomers, racemates, or other mixtures thereof of the compounds described herein or a pharmaceutically acceptable salt or a mixture thereof. In those situations, the single enantiomer or diastereomer, i.e., optically active form, can be obtained by asymmetric synthesis or by resolution. Resolution can be accomplished, for example, by conventional methods such as crystallization in the presence of a resolving agent, or chromatography, using for example, a chiral high pressure liquid chromatography (HPLC) column.

Compositions provided herein that include a compound described herein or pharmaceutically acceptable salts, isomer, or a mixture thereof may include racemic mixtures, or mixtures containing an enantiomeric excess of one enantiomer or single diastereomers or diastereomeric mixtures. All such isomeric forms of these compounds are expressly included herein the same as if each and every isomeric form were specifically and individually listed.

A composition comprising a mixture of enantiomers (or diastereomers) of a compound described herein or a pharmaceutically acceptable salt thereof, is also provided herein. In some embodiments, the composition comprises a single enantiomer of the compound and is substantially free of the other enantiomer. In certain embodiments, the compound of Formula I (or another Formula as described herein) contains one or more additional stereogenic atom(s) (e.g., at $R^1$ and/or $R^3$). In such instances, the composition may contain a mixture of diastereomers. In some embodiments, the composition comprises a single enantiomer of the compound and is substantially free (i.e., having less than or about 40%, 30%, 25%, 20%, 15%, 10%, 5%, 1%, 0.05%, or 0.01%) of one or more diastereomers.

Accordingly, in certain embodiments, provided is a composition comprising a mixture of Formula IA, or a pharmaceutically acceptable salt thereof, and Formula IB, or a pharmaceutically acceptable salt thereof.

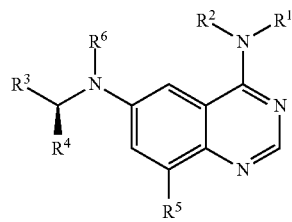

IA

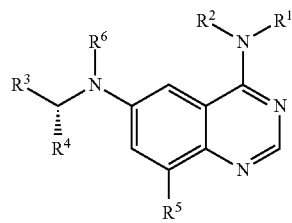

IB wherein m, $R^1$, $R^2$, $R^3$, $R^4$, $R^5$, and $R^6$ are as defined herein.

In one embodiment, the mixture is a racemic mixture. In other embodiments, the composition comprises a mixture of Formula IA, or a pharmaceutically acceptable salt thereof, and Formula IB, or a pharmaceutically acceptable salt thereof, wherein Formula IA is present in excess of over Formula IB, or a pharmaceutically acceptable salt thereof. In certain embodiments, provided is a composition substantially free of Formula IB, having less than or about 40%, 30%, 25%, 20%, 15%, 10%, 5%, 1%, 0.05%, or 0.01% of compounds of Formula IB.

In certain embodiments, provided here in is a composition comprising a mixture of stereoisomers of a compound of Formula I:

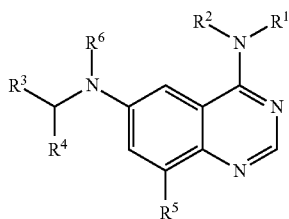

wherein the mixture comprises compounds of Formula IA and IB in a ratio of at least about 3:1:

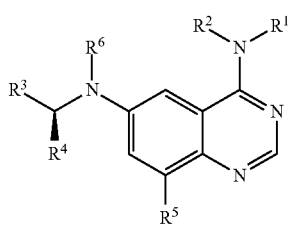

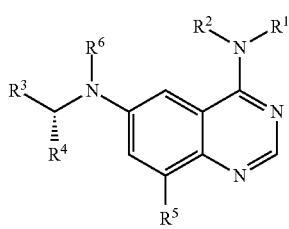

wherein m, $R^1$, $R^2$, $R^3$, $R^4$, $R^5$, and $R^6$ are as defined herein.

The stereochemistry of the $R^4$ group depicted in Formula IA may be represented in an alternative way, provided that the configuration of the carbon atom to which it is attached is not altered. For example, compounds of Formula 1A may be depicted in any one of the equivalent representations of Formula IA shown below.

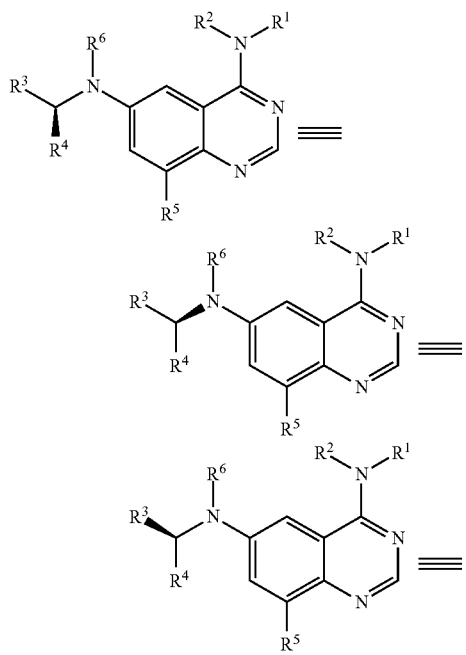

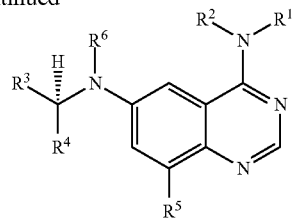

In other embodiments, the mixture comprises compounds of Formula IA and IB in a a molar ratio of at least or about 3:1, at least or about 4:1, at least or about 5:1, at least or about 6:1, at least or about 7:1, at least or about 8:1, at least or about 9:1, at least or about 10:1, at least or about 11:1, at least or about 12:1, at least or about 20:1, at least or about 30:1, at least or about 40:1, at least or about 80:1, at least or about 160:1, or at least or about 320:1, respectively.

In certain embodiments, provided are also chelates, non-covalent complexes, and mixtures thereof, of the compounds described herein or a pharmaceutically acceptable salt, tautomer, stereoisomer, mixture of stereoisomers, prodrug, or deuterated analog thereof. A "chelate" is formed by the coordination of a compound to a metal ion at two (or more) points. A "non-covalent complex" is formed by the interaction of a compound and another molecule wherein a covalent bond is not formed between the compound and the molecule. For example, complexation can occur through van der Waals interactions, hydrogen bonding, and electrostatic interactions (also called ionic bonding).

In certain embodiments, provided are prodrugs of the compounds described herein. "Prodrug" refers to any compound that when administered to a biological system generates the drug substance, or active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically active compound. Non-limiting examples of prodrugs include ester moieties, quaternary ammonium moieties, glycol moieties, and the like.

In certain embodiments, provided is a compound of Formula I, IA, IB, II, III, IV, V, VI, VII or VIII, wherein $R^1$ is

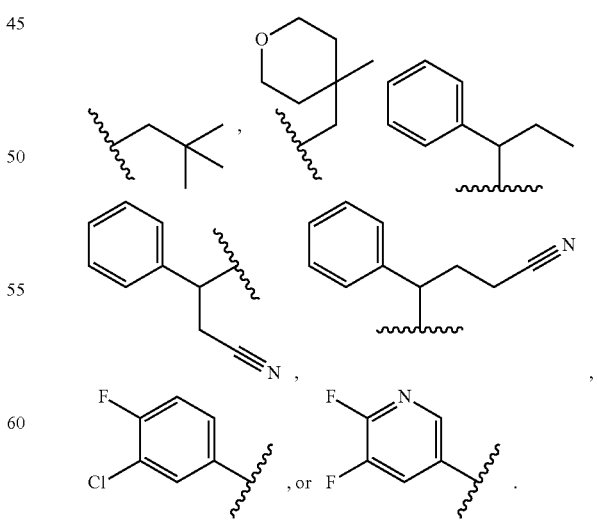

In certain embodiments, provided is a compound of Formula I, IA, IB, II, III, IV, V, VI, VII or VIII, wherein $R^2$ is hydrogen.

In certain embodiments, provided is a compound of Formula I, IA, IB, II, III, IV, V, or VII, wherein $R^3$ is

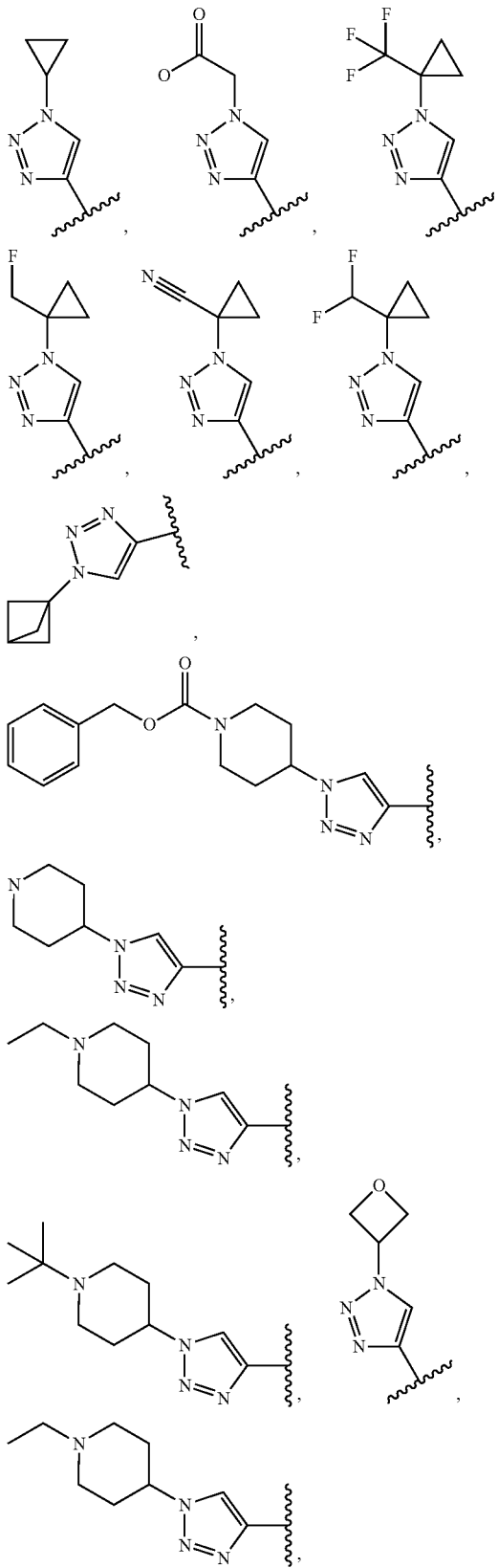

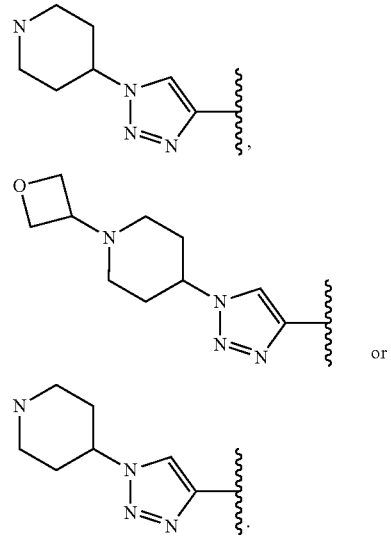

In certain embodiments, provided is a compound of Formula I, IA, IB, II, III, IV, V, VI, VII or VIII, wherein $R^4$ is

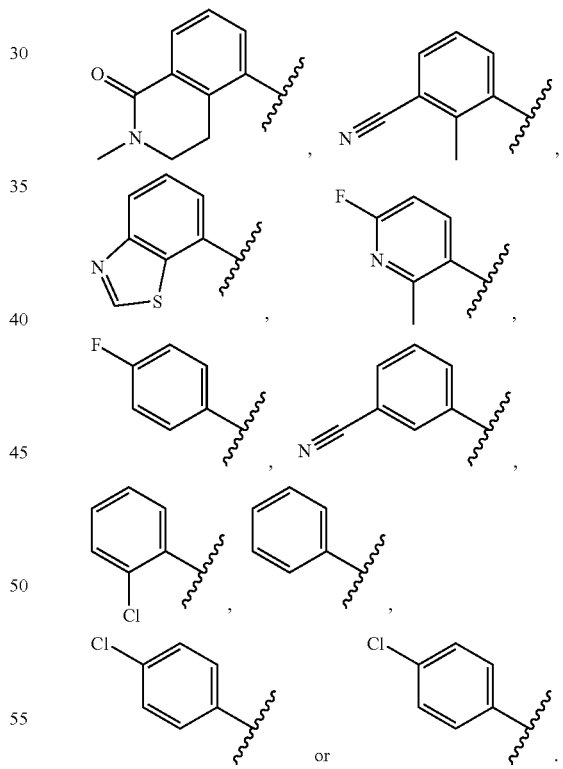

In certain embodiments, provided is a compound of Formula I, IA, IB, II, III, IV, V, VI, VII or VIII, wherein $R^5$ is hydrogen, halo or cyano. In certain embodiments, provided is a compound of Formula I, IA, IB, II, III, IV, V, VI, VII or VIII, wherein $R^6$ is hydrogen or alkyl.

In certain embodiments, provided is a compound of Formula III, IIIA, IV, V, IVA, VA, VII, VIIA, VIII, VIIIA, IX or IXA wherein $Z^3$ is

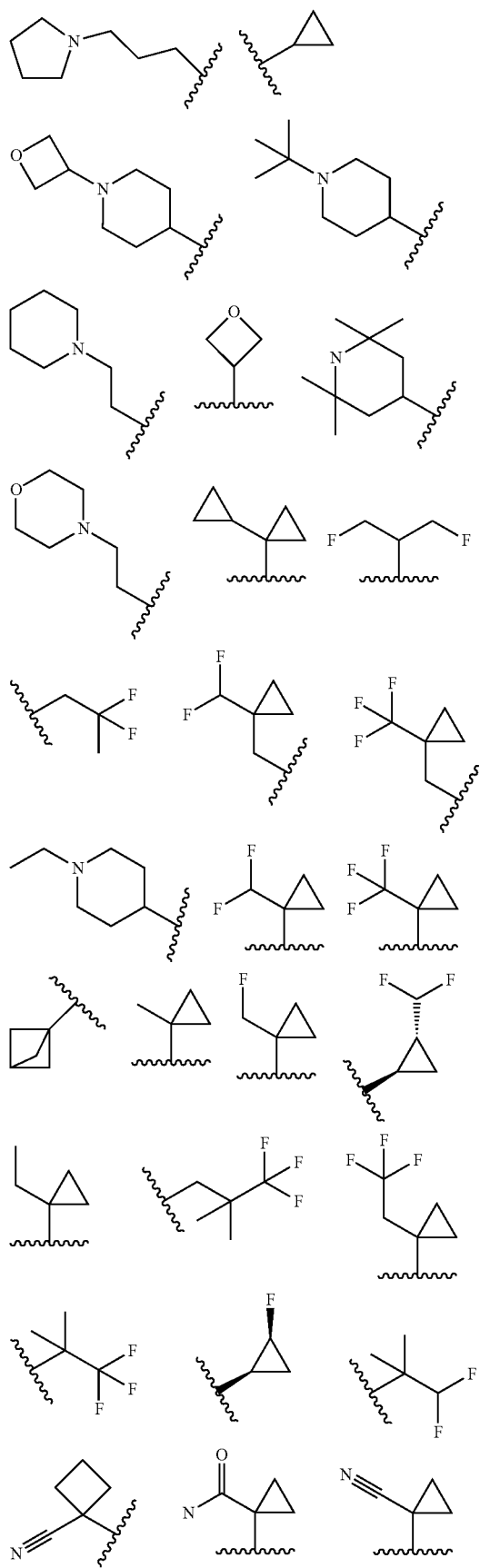
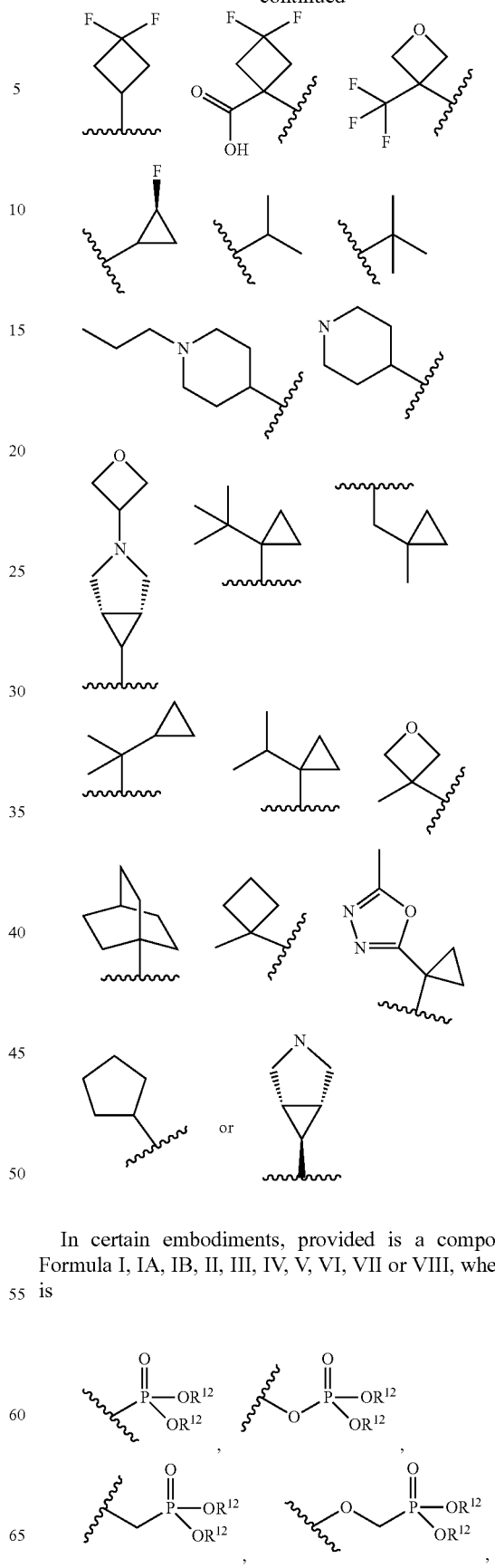
In certain embodiments, provided is a compound of Formula I, IA, IB, II, III, IV, V, VI, VII or VIII, wherein $R^6$ is
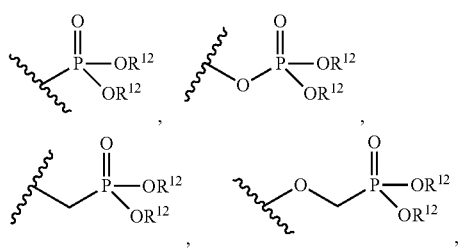

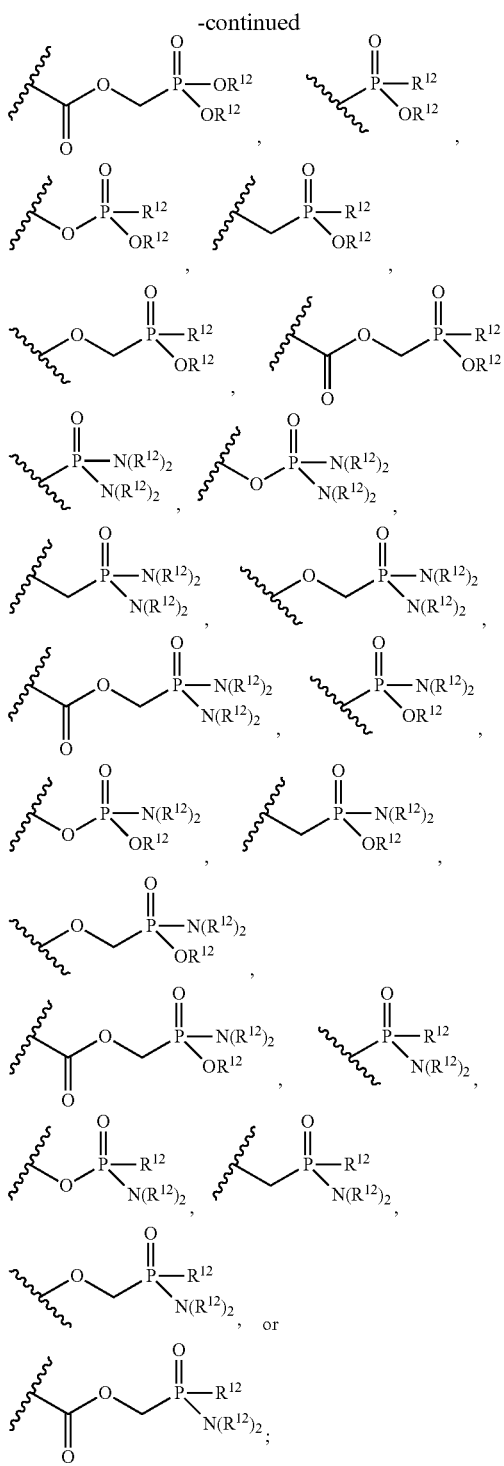

where each $R^{12}$ is independently hydrogen, $C_{1-9}$ alkyl, $C_{2-6}$ alkenyl, $C_{2-6}$ alkynyl, $C_{3-15}$ cycloalkyl, aryl, heteroaryl or heterocyclyl;
wherein any alkyl, alkenyl, alkynyl, cycloalkyl, aryl, heteroaryl or heterocyclyl is optionally substituted with one to four $Z^{1b}$ groups; and
each $Z^{1b}$ is independently oxo, thioxo, hydroxy, halo, —$NO_2$, —$N_3$, cyano, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O($C_{1-9}$ alkyl), —O($C_{2-6}$ alkenyl), —O($C_{2-6}$ alkynyl), —O($C_{3-15}$ cycloalkyl), —O($C_{1-8}$ haloalkyl), —O(aryl), —O(heteroaryl), —O(heterocyclyl), —$NH_2$, —NH($C_{1-9}$ alkyl), —NH($C_{2-6}$ alkenyl), —NH($C_{2-6}$ alkynyl), —NH($C_{3-15}$ cycloalkyl), —NH($C_{1-8}$ haloalkyl), —NH(aryl), —NH(heteroaryl), —NH(heterocyclyl), —N($C_{1-9}$ alkyl)$_2$, —N($C_{3-15}$ cycloalkyl)$_2$, —N($C_{2-6}$ alkenyl)$_2$, —N($C_{2-6}$ alkynyl)$_2$, —N($C_{3-15}$ cycloalkyl)$_2$, —N($C_{1-8}$ haloalkyl)$_2$, —N(aryl)$_2$, —N(heteroaryl)$_2$, —N(heterocyclyl)$_2$, —N($C_{1-9}$ alkyl)($C_{3-15}$ cycloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)($C_{1-8}$ haloalkyl), —N($C_{1-9}$ alkyl)(aryl), —N($C_{1-9}$ alkyl)(heteroaryl), —N($C_{1-9}$ alkyl)(heterocyclyl), —C(O)($C_{1-9}$ alkyl), —C(O)($C_{2-6}$ alkenyl), —C(O)($C_{2-6}$ alkynyl), —C(O)($C_{3-15}$ cycloalkyl), —C(O)($C_{1-8}$ haloalkyl), —C(O)(aryl), —C(O)(heteroaryl), —C(O)(heterocyclyl), —C(O)O($C_{1-9}$ alkyl), —C(O)O($C_{2-6}$ alkenyl), —C(O)O($C_{2-6}$ alkynyl), —C(O)O($C_{3-15}$ cycloalkyl), —C(O)O($C_{1-8}$ haloalkyl), —C(O)O(aryl), —C(O)O(heteroaryl), —C(O)O(heterocyclyl), —C(O)$NH_2$, —C(O)NH($C_{1-9}$ alkyl), —C(O)NH($C_{2-6}$ alkenyl), —C(O)NH($C_{2-6}$ alkynyl), —C(O)NH($C_{3-15}$ cycloalkyl), —C(O)NH($C_{1-8}$ haloalkyl), —C(O)NH(aryl), —C(O)NH(heteroaryl), —C(O)NH(heterocyclyl), —C(O)N($C_{1-9}$ alkyl)$_2$, —C(O)N($C_{3-15}$ cycloalkyl)$_2$, —C(O)N($C_{2-6}$ alkenyl)$_2$, —C(O)N($C_{2-6}$ alkynyl)$_2$, —C(O)N($C_{3-15}$ cycloalkyl)$_2$, —C(O)N($C_{1-8}$ haloalkyl)$_2$, —C(O)N(aryl)$_2$, —C(O)N(heteroaryl)$_2$, —C(O)N(heterocyclyl)$_2$, —NHC(O)($C_{1-9}$ alkyl), —NHC(O)($C_{2-6}$ alkenyl), —NHC(O)($C_{2-6}$ alkynyl), —NHC(O)($C_{3-15}$ cycloalkyl), —NHC(O)($C_{1-8}$ haloalkyl), —NHC(O)(aryl), —NHC(O)(heteroaryl), —NHC(O)(heterocyclyl), —NHC(O)O($C_{1-9}$ alkyl), —NHC(O)O($C_{2-6}$ alkenyl), —NHC(O)O($C_{2-6}$ alkynyl), —NHC(O)O($C_{3-15}$ cycloalkyl), —NHC(O)O($C_{1-8}$ haloalkyl), —NHC(O)O(aryl), —NHC(O)O(heteroaryl), —NHC(O)O(heterocyclyl), —NHC(O)NH($C_{1-9}$ alkyl), —NHC(O)NH($C_{2-6}$ alkenyl), —NHC(O)NH($C_{2-6}$ alkynyl), —NHC(O)NH($C_{3-15}$ cycloalkyl), —NHC(O)NH($C_{1-8}$ haloalkyl), —NHC(O)NH(aryl), —NHC(O)NH(heteroaryl), —NHC(O)NH(heterocyclyl), —SH, —S($C_{1-9}$ alkyl), —S($C_{2-6}$ alkenyl), —S($C_{2-6}$ alkynyl), —S($C_{3-15}$ cycloalkyl), —S($C_{1-8}$ haloalkyl), —S(aryl), —S(heteroaryl), —S(heterocyclyl), —NHS(O)($C_{1-9}$ alkyl), —N($C_{1-9}$ alkyl)(S(O)($C_{1-9}$ alkyl), —S(O)N($C_{1-9}$ alkyl)$_2$, —S(O)($C_{1-9}$ alkyl), —S(O)(NH)($C_{1-9}$ alkyl), —S(O)($C_{2-6}$ alkenyl), —S(O)($C_{2-6}$ alkynyl), —S(O)($C_{3-15}$ cycloalkyl), —S(O)($C_{1-8}$ haloalkyl), —S(O)(aryl), —S(O)(heteroaryl), —S(O)(heterocyclyl), —S(O)$_2$($C_{1-9}$ alkyl), —S(O)$_2$($C_{2-6}$ alkenyl), —S(O)$_2$($C_{2-6}$ alkynyl), —S(O)$_2$($C_{3-15}$ cycloalkyl), —S(O)$_2$($C_{1-8}$ haloalkyl), —S(O)$_2$(aryl), —S(O)$_2$(heteroaryl), —S(O)$_2$(heterocyclyl), —S(O)$_2$NH($C_{1-9}$ alkyl), or —S(O)$_2$N($C_{1-9}$ alkyl)$_2$;
wherein any alkyl, cycloalkyl, aryl, heteroaryl, or heterocyclyl is optionally substituted with one to four halo, $C_{1-9}$ alkyl, $C_{1-8}$ haloalkyl, —OH, —$NH_2$, —NH($C_{1-9}$ alkyl), —NH($C_{3-15}$ cycloalkyl), —NH($C_{1-8}$ haloalkyl), —NH(aryl), —NH(heteroaryl), —NH(heterocyclyl), —N($C_{1-9}$ alkyl)$_2$, —N($C_{3-15}$ cycloalkyl)$_2$, —NHC(O)($C_{3-15}$ cycloalkyl), —NHC(O)($C_{1-8}$ haloalkyl), —NHC(O)(aryl), —NHC(O)(heteroaryl), —NHC(O)(heterocyclyl), —NHC(O)O($C_{1-9}$ alkyl), —NHC(O)O($C_{2-6}$ alkynyl), —NHC(O)O($C_{3-15}$ cycloalkyl), —NHC(O)O($C_{1-8}$ haloalkyl), —NHC(O)O(aryl), —NHC(O)O(heteroaryl), —NHC(O)O(heterocyclyl), —NHC(O)NH($C_{1-9}$ alkyl), —S(O)(NH)($C_{1-9}$ alkyl), S(O)$_2$($C_{1-9}$ alkyl), —S(O)$_2$($C_{3-15}$ cycloalkyl), —S(O)$_2$($C_{1-8}$ haloalkyl), —S(O)$_2$(aryl), —S(O)$_2$(heteroaryl), —S(O)$_2$(heterocyclyl), —S(O)$_2$NH(C$_{1-9}$ alkyl), —S(O)$_2$N(C$_{1-9}$ alkyl)$_2$, —O(C$_{3-15}$ cycloalkyl), —O(C$_{1-8}$ haloalkyl), —O(aryl), —O(heteroaryl), —O(heterocyclyl), or —O(C$_{1-9}$ alkyl).

In certain embodiments, R$^6$ is

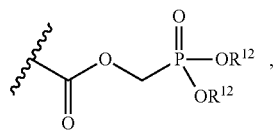

and each R$^{12}$ is independently as defined herein.

In certain embodiments, R$^6$ is

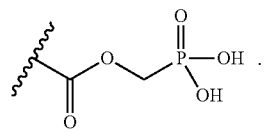 [SMILES: *C(=O)OCP(=O)(O)O]

R$^6$ also includes all individual stereoisomers, and mixtures thereof, including but not limited to, chirality at the phosphorous atom such as in the exemplary moieties shown above.

Also provided herein are the in vivo metabolic products of the compounds described herein. Such products may result, for example, from the oxidation, reduction, hydrolysis, amidation, esterification, and the like, of the administered compound, primarily due to enzymatic processes.

Therapeutic Uses of the Compounds

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

"Subject" refers to an animal, such as a mammal (including a human), that has been or will be the object of treatment, observation or experiment. The methods described herein may be useful in human therapy and/or veterinary applications. In some embodiments, the subject is a mammal. In one embodiment, the subject is a human.

The term "therapeutically effective amount" or "effective amount" of a compound described herein or a pharmaceutically acceptable salt, tautomer, stereoisomer, mixture of stereoisomers, prodrug, or deuterated analog thereof means an amount sufficient to effect treatment when administered to a subject, to provide a therapeutic benefit such as amelioration of symptoms or slowing of disease progression. For example, a therapeutically effective amount may be an amount sufficient to decrease a symptom of a disease or condition responsive to inhibition of Cot activity. The therapeutically effective amount may vary depending on the subject, and disease or condition being treated, the weight and age of the subject, the severity of the disease or condition, and the manner of administering, which can readily be determined by one or ordinary skill in the art.

The term "inhibition" indicates a decrease in the baseline activity of a biological activity or process. "Inhibition of activity of Cot" or variants thereof refers to a decrease in activity in Cot as a direct or indirect response to the presence of a compound of the present application relative to the activity Cot in the absence of the compound of the present application. "Inhibition of Cot" refers to a decrease in Cot activity as a direct or indirect response to the presence of a compound described herein relative to the activity of Cot in the absence of the compound described herein. In some embodiments, the inhibition of Cot activity may be compared in the same subject prior to treatment, or other subjects not receiving the treatment.

The methods described herein may be applied to cell populations in vivo or ex vivo. "In vivo" means within a living individual, as within an animal or human. In this context, the methods described herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine, and saliva. Exemplary tissue samples include tumors and biopsies thereof. In this context, the compounds and compositions described herein may be used for a variety of purposes, including therapeutic and experimental purposes. For example, the compounds and compositions described herein may be used ex vivo to determine the optimal schedule and/or dosing of administration of a Cot inhibitor for a given indication, cell type, individual, and other parameters. Information gleaned from such use may be used for experimental purposes or in the clinic to set protocols for in vivo treatment. Other ex vivo uses for which the compounds and compositions described herein may be suited are described below or will become apparent to those skilled in the art. The selected compounds may be further characterized to examine the safety or tolerance dosage in human or non-human subjects. Such properties may be examined using commonly known methods to those skilled in the art.

The compounds disclosed herein are useful for the treatment of diseases or conditions mediated by Cot. Non-limiting examples of diseases or conditions mediated by Cot include, without limitation, cancer, diabetes, and inflammatory diseases such as rheumatoid arthritis (RA), multiple sclerosis (MS), inflammatory bowel disease (IBD), sepsis, psoriasis, misregulated TNF expression and graft rejection.

In further embodiments, the methods are provided for alleviating a symptom of a disease or disorder mediated by Cot. In some embodiments, the methods include identifying a mammal having a symptom of a disease or disorder mediated by Cot, and providing to the mammal an amount of a compound as described herein effective to ameliorate (i.e., lessen the severity of) the symptom.

In some embodiments, the disease or condition mediated by Cot is a solid tumor. In particular embodiments, the solid tumor is from pancreatic cancer, bladder cancer, colorectal cancer, breast cancer, prostate cancer, renal cancer, hepatocellular cancer, lung cancer, ovarian cancer, cervical cancer, gastric cancer, esophageal cancer, head and neck cancer, melanoma, neuroendocrine cancers, CNS cancers, brain tumors (e.g., glioma, anaplastic oligodendroglioma, adult glioblastoma multiforme, and adult anaplastic astrocytoma), bone cancer, or soft tissue sarcoma. In some embodiments, the solid tumor is from non-small cell lung cancer, small-cell lung cancer, colon cancer, CNS cancer, melanoma, ovarian cancer, renal cancer, prostate cancer, or breast cancer.

In some embodiments, the disease or condition mediated by Cot is diabetes, which includes any metabolic disorder characterized by impaired insulin production and glucose tolerance. In some embodiments, diabetes includes type 1 and type 2 diabetes, gestational diabetes, prediabetes, insulin resistance, metabolic syndrome, impaired fasting glycaemia and impaired glucose tolerance. Type 1 diabetes is also known as Insulin Dependent Diabetes Mellitus (IDDM). Type 2 is also known as Non-Insulin-Dependent Diabetes Mellitus (NIDDM).

In some embodiments, the disease or condition mediated by Cot is an inflammatory disease or LPS induced endotoxin shock. In some embodiments, the disease is an autoimmune disease. In particular embodiments, the autoimmune disease is systemic lupus erythematosus (SLE), myestenia gravis, rheumatoid arthritis (RA), acute disseminated encephalomyelitis, idiopathic thrombocytopenic purpura, multiple sclerosis (MS), inflammatory bowel disease (IBD), sepsis, psoriasis, Sjoegren's syndrome, psoriasis, autoimmune hemolytic anemia, asthma, or chronic obstructive pulmonary disease (COPD). In other embodiments, the disease is inflammation. In yet other embodiments, the disease is excessive or destructive immune reactions, such as asthma, rheumatoid arthritis, multiple sclerosis, chronic obstructive pulmonary disease (COPD), and lupus.

In some embodiments, the disease or condition mediated by Cot is inflammatory bowel disease (IBD). The term "inflammatory bowel disease" or "IBD" as used herein is a collective term describing inflammatory disorders of the gastrointestinal tract, the most common forms of which are ulcerative colitis and Crohn's disease. Other forms of IBD that can be treated with the presently disclosed compounds, compositions and methods include diversion colitis, ischemic colitis, infectious colitis, chemical colitis, microscopic colitis (including collagenous colitis and lymphocytic colitis), atypical colitis, pseudomembranous colitis, fulminant colitis, autistic enterocolitis, indeterminate colitis, Behçet's disease, gastroduodenal CD, jejunoileitis, ileitis, ileocolitis, Crohn's (granulomatous) colitis, irritable bowel syndrome, mucositis, radiation induced enteritis, short bowel syndrome, celiac disease, stomach ulcers, diverticulitis, pouchitis, proctitis, and chronic diarrhea.

Treating or preventing IBD also includes ameliorating or reducing one or more symptoms of IBD. As used herein, the term "symptoms of IBD" refers to detected symptoms such as abdominal pain, diarrhea, rectal bleeding, weight loss, fever, loss of appetite, and other more serious complications, such as dehydration, anemia and malnutrition. A number of such symptoms are subject to quantitative analysis (e.g. weight loss, fever, anemia, etc.). Some symptoms are readily determined from a blood test (e.g. anemia) or a test that detects the presence of blood (e.g. rectal bleeding). The term "wherein said symptoms are reduced" refers to a qualitative or quantitative reduction in detectable symptoms, including but not limited to a detectable impact on the rate of recovery from disease (e.g. rate of weight gain). The diagnosis is typically determined by way of an endoscopic observation of the mucosa, and pathologic examination of endoscopic biopsy specimens.

The course of IBD varies, and is often associated with intermittent periods of disease remission and disease exacerbation. Various methods have been described for characterizing disease activity and severity of IBD as well as response to treatment in subjects having IBD. Treatment according to the present methods are generally applicable to a subject having IBD of any level or degree of disease activity.

In some embodiments, the disease or condition treated by the administration of a compound of composition described herein includes acute gout and ankylosing spondylitis, allergic disorders, Alzheimer's disease, Amyotrophic lateral sclerosis (ALS), Amyotrophic lateral sclerosis and multiple sclerosis, atherosclerosis, bacterial infections, bone cancer pain and pain due to endometriosis, BRAF resistant melanoma, brain stem glioma or pituitary adenomas, burns, bursitis, cancer of the anal region, cancer of the endocrine system, cancer of the kidney or ureter (e.g. renal cell carcinoma carcinoma of the renal pelvis), cancer of the penis, cancer of the small intestine, cancer of the thyroid, cancer of the urethra, cancers of the blood such as acute myeloid leukemia, cancers of the tongue, carcinoma of the cervix, carcinoma of the endometrium, carcinoma of the fallopian tubes, carcinoma of the renal pelvis, carcinoma of the vagina or carcinoma of the vulva, chronic mueloid leukemia, chronic or acute leukemia, chronic pain, classic Bartter syndrome, common cold conjunctivitis, coronary heart disease, cutaneous or intraocular melanoma, dermatitis, dysmenorrhea, eczema, endometriosis, familial adenomatous polyposis, fibromyalgia, fungal infections, gout, gynecologic tumors, uterine sarcomas, carcinoma of the fallopian tubes, headache, hemophilic arthropathy, Parkinson's disease, AIDS, herpes zoster, Hodgkin's disease, Huntington's, hyperprostaglandin E syndrome, influenza, iritis, juvenile arthritis, juvenile onset rheumatoid arthritis, juvenile rheumatoid arthritis, low back and neck pain, lynphocytic lymphomas, myofascial disorders, myositis, neuralgia, neurodegenerative disorders such as Alzheimer's disease, neuroinflammatory disorders, neuropathic pain, carcinoma of the vulva, Parkinson's disease, pediatric malignancy, pulmonary fibrosis rectal cancer, rhinitis, sarcoidosis, sarcomas of soft tissues, scleritis, skin cancer, solid tumors of childhood, spinal axis tumors, sprains and strains, stomach cancer, stroke, subacute and chronic musculoskeletal pain syndromes such as bursitis, surgical or dental procedures, symptoms associated with influenza or other viral infections, synovitis, toothache, ulcers, uterine cancer, uterine sarcomas, uveitis, vasculitis, viral infections, viral infections {e.g. influenza) and wound healing.

Criteria useful for assessment of disease activity in subjects with ulcerative colitis can be found in, e.g., Truelove et al. (1955) Br Med J 2:1041-1048.) Using these criteria, disease activity can be characterized in a subject having IBD as mild disease activity or severe disease activity. Subjects who do not meet all the criteria for severe disease activity, and who exceed the criteria for mild disease activity are classified as having moderate disease activity.

The presently disclosed treatment methods can also be applied at any point in the course of the disease. In certain embodiments, the methods are applied to a subject having IBD during a time period of remission (i.e., inactive disease). In such embodiments, the present methods provide benefit by extending the time period of remission (e.g., extending the period of inactive disease) or by preventing, reducing, or delaying the onset of active disease. In other embodiments, methods may be applied to a subject having IBD during a period of active disease. Such methods provide benefit by reducing the duration of the period of active disease, reducing or ameliorating one or more symptoms of IBD, or treating IBD.

Measures for determining efficacy of treatment of IBD in clinical practice have been described and include, for example, the following: symptom control; fistula closure; extent of corticosteroid therapy required; and, improvement in quality of life. Heath-related quality of life (HRQL) can be assessed using the Inflammatory Bowel Disease Questionnaire (IBDQ), which is extensively used in clinical practice to assess quality of life in a subject with IBD. (See Guyatt et al. (1989) Gastroenterology 96:804-810.) Improvements in any of the foregoing response criteria are specifically provided by the methods of the present disclosure.

Combination Therapies

In one embodiment, the compounds disclosed herein may be used in combination with one or more additional therapeutic agent that are being used and/or developed to treat inflammatory disorders (e.g., IBD). The one or more additional therapeutic agent may be a α4β7 inhibitor, a steroid, a MMP-9 antibody, a S1P1 agonist, a TNF biologic, or any combination thereof.

In some embodiments, the one or more additional therapeutic agent may be a α4β7 integrin inhibitor, or an agent that inhibits the expression and/or activity of α4β7 integrin. The inhibitor can be small molecule or biologic. For example, the α4β7 integrin inhibitor can be natalizumab or vedolizumab.

In some embodiments, the one or more additional therapeutic agent may be a steroid, including but not limited to, corticosteroids. Corticosteroids may be administered by various routes, including intravenously (i.e., methylprednisolone, hydrocortisone), orally (i.e., prednisone, prednisolone, budesonide, dexamethasone), or topically (i.e., enema, suppository, or foam preparations).

In some embodiments, the one or more additional therapeutic agent may be an MMP9 inhibitor, or an agent that inhibits the expression and/or activity of MMP9. A representative protein sequence for MMP9 is GenBank Accession No. NP_004985. The inhibitor can be small molecule or biologic. For instance, Gu et al., *The Journal of Neuroscience*, 25(27): 6401-6408 (2005) discloses a specific MMP9 inhibitor, SB-3CT (CAS 292605-14-2). Further, siRNA, antisense RNA and antibodies have also been demonstrated to inhibit the expression or activity of MMP9 and are within the scope of the present disclosure. In one embodiment, an MMP9 inhibitor is a monoclonal anti-MMP9 antibody. In some embodiment, the one or more additional therapeutic agent includes an MMP9 inhibitor and a nucleoside analog such as gemcitabine.

In some embodiments, the one or more additional therapeutic agent may be a Sphingosine 1-Phosphate Receptor (S1P1) inhibitor, or an agent that inhibits the expression and/or activity of S1P1. The inhibitor can be small molecule or biologic. For example, the S1P1 inhibitor can be RPC1063.

In some embodiments, the one or more additional therapeutic agent may be a TNF inhibitor, or an agent that inhibits the expression and/or activity of TNF. The inhibitor can be small molecule or biologic. For example, the TNF inhibitor can be golimumab.

In some embodiments, the one or more additional therapeutic agent is being used and/or developed to treat ulcerative colitis (UC) and/or Crohn disease (CD). The agent can be a biologic or small molecule. In some embodiments, the agent is a modulator (e.g., agonist or antagonist) of S1P1, IL-6, CX3CL1, DHODH, α4, β7, JAK, TNF, CB, IL-12/IL-23, CCL20, TLR9, MAdCAM, CCR9, CXCL10, Smad7, PDE4, MC, VLA-1, GC, GATA-3, Eotaxin, FFA2, LIGHT, FMS, MMP9, CD40, Steroid, 5-ASA, Immunomod, STAT3, and/or EP4.

Non-limiting examples of agents being used and/or developed to treat ulcerative colitis (UC) include GSK3050002 (CCL20 modulator, by GSK), GS-5745 (MMP9 modulator, by Gilead), AVX-470 (TNF modulator, by Avaxia), Bertilimumab (Eotaxin modulator, by Immune Pharma), Simponi (TNF modulator, by Johnson & Johnson and Merck), RX-10001 (by Resolvyx), IBD-98 (5-ASA modulator, by Holy Stone), SP-333 (GC modulator, by Synergy), KAG-308 (EP4 modulator, by Kaken), SB012 (GATA-3 modulator, by Sterna), AJM300 (a4 modulator, by Ajinomoto), BL-7040 (TLR9 modulator, by BiolineRx), TAK-114 (SAT3 modulator, by Takeda), CyCol (by Sigmoid), GWP-42003 (CB modulator, by GW Pharma), ASP3291 (MC modulator, by Drais), GLPG0974 (FFA2 modulator, by Galapagos), Ozanimod (S1P1 modulator, by Receptos), ASP015K (JAK modulator, by Astellas), Apremilast (PDE4 modulator, by Celgene), Zoenasa (by Altheus), Kappaproct (TLR9 modulator, by InDex), Phosphatidylcholine (by Dr Falk/Lipid Tx), Tofacitinib (JAk modulator, by Pfizer), Cortment (Steroid modulator, by Ferring), Uceris (Steroid modulator, by Salix), and 5-ASA modulators such as Delzicol (by Actavis), Canasa (by Aptalis), Asacol (by Actavis), Pentasa (by Shire/Ferring), Lialda (by Shire), Mezavant (by Shire), Apriso (by Salix), Colazal (by Salix), Giazo (by Salix), and Salofalk (by Dr Falk). Non-limiting examples of agents being used and/or developed to treat Crohn disease (CD) include FFP102 (CD40 modulator, by Fast Forward), E6011 (CX3CL1 modulator, by Eisai), PF-06480605 (by Pfizer), QBECO SSI (Immunomod modulator, by Qu Biologics), PDA-001 (by Celgene), BI 655066 (IL-12/IL-23 modulator, by Boehringer), TNFα kinoid (TNF modulator, by Neovacs), AMG 139/MEDI-2070 (IL-12/IL-23 modulator, by AstraZeneca), PF-04236921 (IL-6 modulator, by Pfizer), Tysabri (β7 modulator, marketed by Biogen Idec in the U.S.), Cimzia (marketed by UCB in the U.S.), JNJ-40346527 (FMS modulator, by J&J), SGX-203 (Steroid modulator, by Solgenix), CyCron (by Sigmoid), CCX507 (CCR9 modulator, by ChemoCentryx), MT1303 (S1P1 modulator, by Mitsubishi), 6-MP (by Teva), ABT-494 (JAk modulator, by Abbvie), Tofacitinib (JAk modulator, by Pfizer), GLPG0634 (JAk modulator, by Galapagos), TRK-170 (β7 modulator, by Toray), Mongersen (Smad7 modulator, by Celgene), RHB-104 (by Redhill), Rifaxmin EIR (by Salix), Budenofalk (by Dr Falk), and Entocort (by AstraZeneca).

Non-limiting examples of agents being used and/or developed to treat ulcerative colitis (UC) and Crohn disease (CD) include PF-06410293 (by Pfizer), SAN-300 (VLA-1 modulator, by Salix), SAR252067 (LIGHT modualtor, by Sanofi), PF-00547659 (MAdCAM modualtor, by Pfizer), Eldelumab (Smad7 modulator, by BMS), AMG 181/MEDI-7183 (β7 modulator, by Amgen/AstraZeneca), Etrolizumab (β7 modulator, by Roche), Ustekinumab (IL-12/IL-23 modulator, by J&J), Remicade (TNF modulator, by J&J and Merck), Entyvio (β7 modulator, by Takeda), Humira (TNF modulator, by Abbvie), Infliximab (by Celtrion), PF-06651600 (by Pfizer), GSK2982772 (by GSK), GLPG1205 (FFA2 modulator, by Galapagos), AG014 (by Intrexon) and Vidofludimus (DHODH modulator, by 4SC).

In some embodiments, the one or more additional therapeutic agent may be a JAK inhibitor, particularly a JAK-1 selective inhibitor. The inhibitor can be small molecule or biologic. For example, the JAK inhibitor can be Filgotinib, GLPG0634 (JAK modulator, by Galápagos).

Kits

Provided herein are also kits that include a compound of Formula I, or a pharmaceutically acceptable salt, tautomer, stereoisomer, mixture of stereoisomers, prodrug, or deuterated analog thereof, and suitable packaging. In one embodiment, a kit further includes instructions for use. In one aspect, a kit includes a compound of Formula I (or any other Formula described herein), or a pharmaceutically acceptable salt, tautomer, stereoisomer, mixture of stereoisomers, prodrug, or deuterated analog thereof, and a label and/or instructions for use of the compounds in the treatment of the indications, including the diseases or conditions, described herein.

Provided herein are also articles of manufacture that include a compound described herein or a pharmaceutically acceptable salt, tautomer, stereoisomer, mixture of stereoisomers, prodrug, or deuterated analog thereof in a suitable container. The container may be a vial, jar, ampoule, preloaded syringe, and intravenous bag.

Pharmaceutical Compositions and Modes of Administration

Compounds provided herein are usually administered in the form of pharmaceutical compositions. Thus, provided herein are also pharmaceutical compositions that contain one or more of the compounds described herein or a pharmaceutically acceptable salt, tautomer, stereoisomer, mixture of stereoisomers, prodrug, or deuterated analog thereof and one or more pharmaceutically acceptable vehicles selected from carriers, adjuvants and excipients. Suitable pharmaceutically acceptable vehicles may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.).

The pharmaceutical compositions may be administered in either single or multiple doses. The pharmaceutical composition may be administered by various methods including, for example, rectal, buccal, intranasal and transdermal routes. In certain embodiments, the pharmaceutical composition may be administered by intra-arterial injection, intravenously, intraperitoneally, parenterally, intramuscularly, subcutaneously, orally, topically, or as an inhalant.

One mode for administration is parenteral, for example, by injection. The forms in which the pharmaceutical compositions described herein may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Oral administration may be another route for administration of the compounds described herein. Administration may be via, for example, capsule or enteric coated tablets. In making the pharmaceutical compositions that include at least one compound described herein or a pharmaceutically acceptable salt, tautomer, stereoisomer, mixture of stereoisomers, prodrug, or deuterated analog thereof, the active ingredient is usually diluted by an excipient and/or enclosed within such a carrier that can be in the form of a capsule, sachet, paper or other container. When the excipient serves as a diluent, it can be in the form of a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include lubricating agents such as talc, magnesium stearate, and mineral oil; wetting agents; emulsifying and suspending agents; preserving agents such as methyl and propylhydroxy-benzoates; sweetening agents; and flavoring agents.

The compositions that include at least one compound described herein or a pharmaceutically acceptable salt, tautomer, stereoisomer, mixture of stereoisomers, prodrug, or deuterated analog thereof can be formulated so as to provide quick, sustained or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods disclosed herein employ transdermal delivery devices ("patches"). Such transdermal patches may be used to provide continuous or discontinuous infusion of the compounds described herein in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

For preparing solid compositions such as tablets, the principal active ingredient may be mixed with a pharmaceutical excipient to form a solid preformulation composition containing a homogeneous mixture of a compound described herein or a pharmaceutically acceptable salt, tautomer, stereoisomer, mixture of stereoisomers, prodrug, or deuterated analog thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can include an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation may include solutions and suspensions in pharmaceutically acceptable, aqueous or organic solvents, or mixtures thereof, and powders. The liquid or solid compositions may contain suitable pharmaceutically acceptable excipients as described herein. In some embodiments, the compositions are administered by the oral or nasal respiratory route for local or systemic effect. In other embodiments, compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

Dosing

The specific dose level of a compound of the present application for any particular subject will depend upon a variety of factors including the activity of the specific compound employed, the age, body weight, general health, sex, diet, time of administration, route of administration, and rate of excretion, drug combination and the severity of the particular disease in the subject undergoing therapy. For example, a dosage may be expressed as a number of milligrams of a compound described herein per kilogram of the subject's body weight (mg/kg). Dosages of between about 0.1 and 150 mg/kg may be appropriate. In some embodiments, about 0.1 and 100 mg/kg may be appropriate. In other embodiments a dosage of between 0.5 and 60 mg/kg may be appropriate. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject.

The daily dosage may also be described as a total amount of a compound described herein administered per dose or per day. Daily dosage of a compound of Formula I may be between about 1 mg and 4,000 mg, between about 2,000 to 4,000 mg/day, between about 1 to 2,000 mg/day, between about 1 to 1,000 mg/day, between about 10 to 500 mg/day, between about 20 to 500 mg/day, between about 50 to 300 mg/day, between about 75 to 200 mg/day, or between about 15 to 150 mg/day.

When administered orally, the total daily dosage for a human subject may be between 1 mg and 1,000 mg, between about 1,000-2,000 mg/day, between about 10-500 mg/day, between about 50-300 mg/day, between about 75-200 mg/day, or between about 100-150 mg/day.

The compounds of the present application or the compositions thereof may be administered once, twice, three, or four times daily, using any suitable mode described above. Also, administration or treatment with the compounds may be continued for a number of days; for example, commonly treatment would continue for at least 7 days, 14 days, or 28 days, for one cycle of treatment. Treatment cycles are well known in cancer chemotherapy, and are frequently alternated with resting periods of about 1 to 28 days, commonly about 7 days or about 14 days, between cycles. The treatment cycles, in other embodiments, may also be continuous.

In a particular embodiment, the method comprises administering to the subject an initial daily dose of about 1 to 800 mg of a compound described herein and increasing the dose by increments until clinical efficacy is achieved. Increments of about 5, 10, 25, 50, or 100 mg can be used to increase the dose. The dosage can be increased daily, every other day, twice per week, or once per week.

Synthesis of the Compounds of Formula I

The compounds may be prepared using the methods disclosed herein and routine modifications thereof, which will be apparent given the disclosure herein and methods well known in the art. Conventional and well-known synthetic methods may be used in addition to the teachings herein. The synthesis of typical compounds described herein may be accomplished as described in the following examples. If available, reagents may be purchased commercially, e.g., from Sigma Aldrich or other chemical suppliers.

General Synthesis

Typical embodiments of compounds described herein may be synthesized using the general reaction schemes described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Given a desired product for which the substituent groups are defined, the necessary starting materials generally may be determined by inspection. Starting materials are typically obtained from commercial sources or synthesized using published methods. For synthesizing compounds which are embodiments described in the present disclosure, inspection of the structure of the compound to be synthesized will provide the identity of each substituent group. The identity of the final product will generally render apparent the identity of the necessary starting materials by a simple process of inspection, given the examples herein. In general, compounds described herein are typically stable and isolatable at room temperature and pressure.

Synthetic Reaction Parameters

The compounds of this disclosure can be prepared from readily available starting materials using, for example, the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts (1999) Protecting Groups in Organic Synthesis, 3rd Edition, Wiley, New York, and references cited therein.

Furthermore, the compounds of this disclosure may contain one or more chiral centers. Accordingly, if desired, such compounds can be prepared or isolated as pure stereoisomers, i.e., as individual enantiomers or diastereomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures or obvious modifications thereof, described in standard reference texts such as Fieser and Fieser's Reagents for Organic Synthesis, Volumes 1-15

(John Wiley, and Sons, 1991), Rodd's Chemistry of Carbon Compounds, Volumes 1-5, and Supplementals (Elsevier Science Publishers, 1989) organic Reactions, Volumes 1-40 (John Wiley, and Sons, 1991), March's Advanced Organic Chemistry, (John Wiley, and Sons, 5th Edition, 2001), and Larock's Comprehensive Organic Transformations (VCH Publishers Inc., 1989).

The term "solvent" generally refers to a solvent inert under the conditions of the reaction being described in conjunction therewith (including, for example, benzene, toluene, acetonitrile, tetrahydrofuran (THF), dimethylformamide (DMF), chloroform, methylene chloride (or dichloromethane), diethyl ether, methanol, and the like). Unless specified to the contrary, the solvents are inert organic solvents, and the reactions may carried out under an inert gas, preferably argon or nitrogen.

In Scheme 1, 1-a is reacted with a suitable amine under standard nucleophilic aromatic substitution conditions in the presence of a base (e.g., $NEt_3$, etc.) and at elevated temperature (e.g., 150° C.) to obtain 1-b. Compounds of Formula I where $R^5$ is cyano are provided by employing a suitable cyanating agent (e.g., CuCN, $Zn(CN)_2$, etc.) in the presence of a catalyst (e.g., palladium, nickel, copper, etc.). Reduction of the nitro moiety on compound 1-b using a suitable reducing agent provides compound 1-c (e.g., Fe, $SnCl_2$, etc.). The synthesis of 1-c can also be done in one pot from 1-a using a suitable solvent (i.e., ethanol). Various compounds of formula 1-a for use in the methods provided herein can be purchased from commercial sources or synthesized by known methods.

Scheme 2 shows the synthesis of compounds 2-d and 2-e, where $R^4$ is as defined herein.

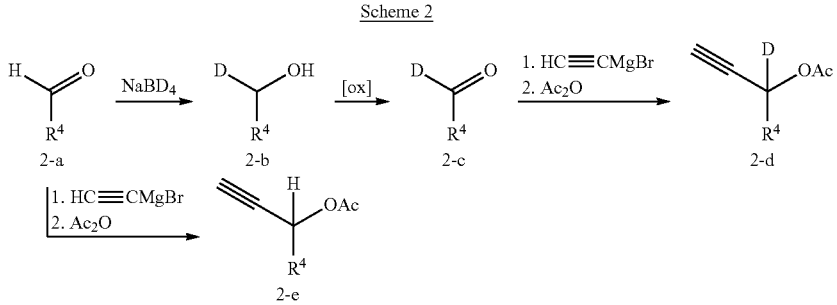

The term "q.s." means adding a quantity sufficient to achieve a stated function, e.g., to bring a solution to the desired volume (i.e., 100%).

The compounds of Formula I may prepared by first providing the substituted quinazoline core, and optionally further modifying the core as desired to provide the substituents disclosed herein. Scheme 1 shows the preparation of the quinazoline core to provide compounds of Formula 1-c, where m, $R^1$, $R^2$, and $R^5$ are as defined herein, or is a functional group that may be converted thereto using standard reaction conditions.

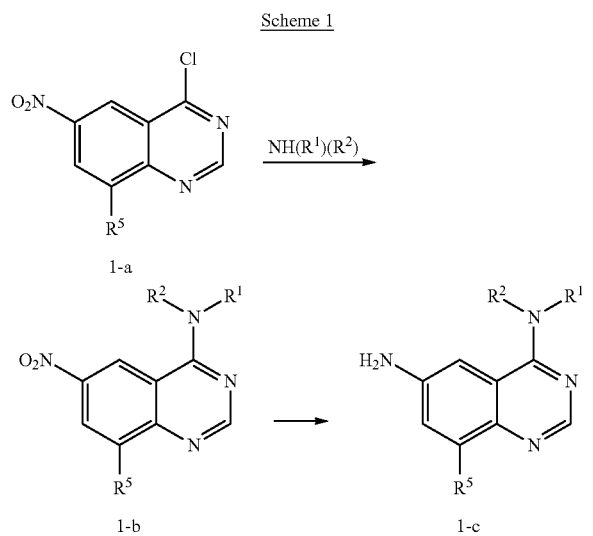

In Scheme 2, deuterated 2-c is provided by reducing suitably substituted aldehyde 2-a with a deuteride-containing reducing agent (e.g., $NaBD_4$), followed by oxidation of 2-b to the corresponding aldehyde 2-c under standard oxidizing conditions (e.g., $MnO_2$, $Fe_2O_3$, NiO, CuO, ZnO, $ZrO_2$, $La_2O_3$, $Sm_2O_3$, $Eu_2O_3$, $Yb_2O_3$, etc.). 2-d is obtained in two steps by reaction of 2-c with ethynyl Grignard, followed by acylation of the resulting alcohol with acetic anhydride in the presence of a base (e.g., pyridine, TEA, etc.). 2-e is provided in a similar two-step process by reacting suitably substituted aldehyde 2-a with ethynyl Grignard, followed by acylation of the resulting alcohol with acetic anhydride.

Scheme 3 shows the synthesis of suitably protected azide compounds of Formula 3-b, where Lg is a leaving group and $Z^3$ is as defined herein.

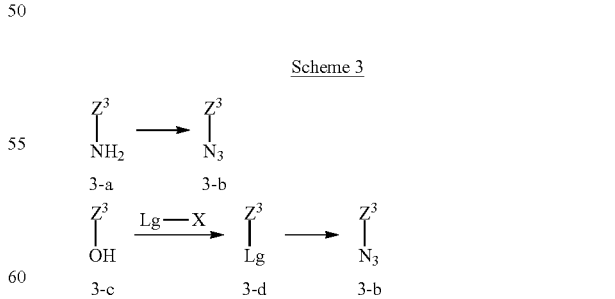

In Scheme 3, suitably substituted amine 3-a is treated with a diazo transfer agent (e.g., imidazole-1-sulfonyl azide hydrochloride) to afford corresponding 3-b. Alternatively, 3-b may be obtained in two steps from alcohol 3-c by conversion of the hydroxyl moiety to a suitable leaving group (Lg) (e.g., TsO-, MsO-, NsO-, TfO—, etc.) followed by nucleophilic displacement with azide.

Scheme 4 shows the synthesis of intermediate compounds of Formula 4-c, where $R^{50}$ is alkyl and $Z^3$ is as defined herein.

corresponding aldehyde 4-c under standard carbonyl deprotection conditions (e.g., aqueous acid).

Scheme 5 shows a general synthesis of exemplary compounds of Formula I, where $Z^3$, m, $R^1$, $R^2$, $R^4$, and $R^5$ and are as defined herein.

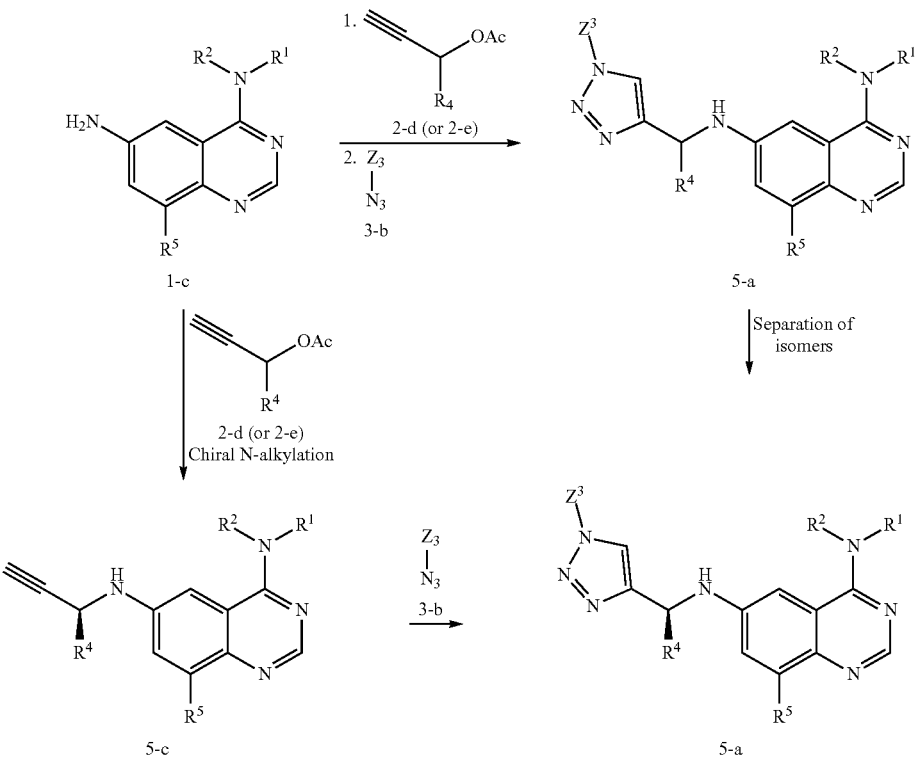

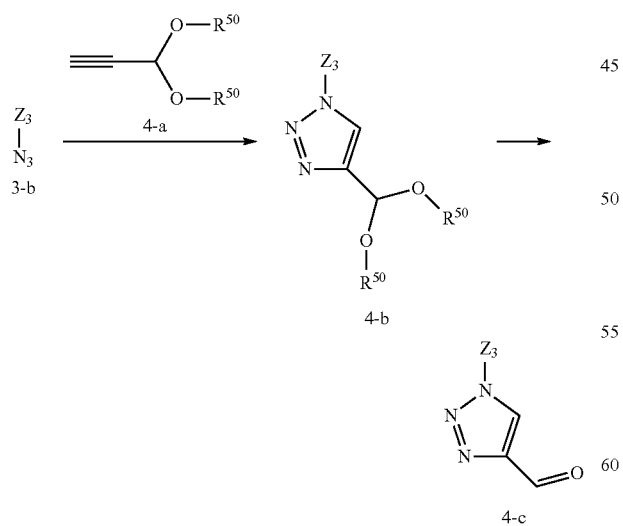

In Scheme 4, suitably substituted triazole 4-b is obtained by reaction of 3-b with 4-a using standard 1,3-dipolar cycloaddition conditions. Acetal 4-b is converted to the In Scheme 5, compounds of Formula 5-c can be provided via N-alkylation of amine 1-c with 2-d (or 2-e), followed by cyclization with azide 3-b under standard 1,3-dipolar cycloaddition conditions. Separation of the isomers of Formula 5-a to give compounds of Formula 5-b can be performed using standard chiral separation/resolution techniques (e.g., chiral chromatography, crystallization, etc.). Alternatively, compounds of Formula 5-b can be provided via enantioselective N-alkylation of 1-c with 2-d (or 2-e) using a chiral metal complex (e.g., [Cu(CH$_3$CN)$_4$]PF$_6$, CuOTf.benzene, Cu(OAc)$_2$, or Cu(I)I, etc., with a chiral ligand). Suitable reaction conditions and exemplary chiral ligands/complexes can be found in the literature (see, e.g., Detz, et al. Angew. Chem. Int. Ed. 2008, 47, 3777-3780). Contacting 5-c with azide 3-b under standard 1,3-dipolar cycloaddition conditions provide 5-b. 5-c may or may not be isolated prior to the addition of 3-b.

Scheme 6 shows an alternate synthesis of compounds of Formula I via imine formation and subsequent nucleophilic addition, where $Z^3$, m, $R^1$, $R^2$, $R^3$, $R^4$, and $R^5$ are as defined herein.

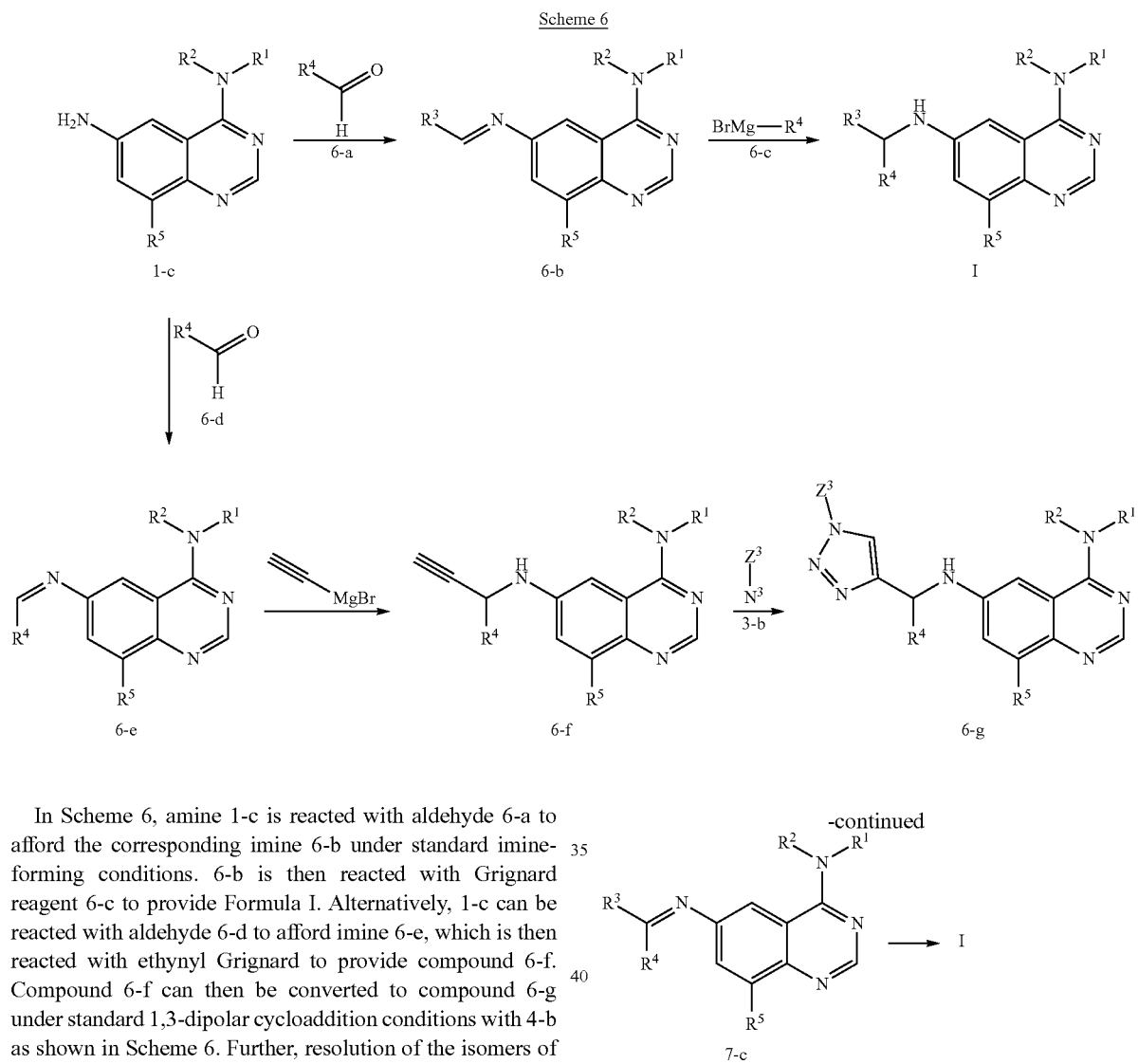

In Scheme 6, amine 1-c is reacted with aldehyde 6-a to afford the corresponding imine 6-b under standard imine-forming conditions. 6-b is then reacted with Grignard reagent 6-c to provide Formula I. Alternatively, 1-c can be reacted with aldehyde 6-d to afford imine 6-e, which is then reacted with ethynyl Grignard to provide compound 6-f. Compound 6-f can then be converted to compound 6-g under standard 1,3-dipolar cycloaddition conditions with 4-b as shown in Scheme 6. Further, resolution of the isomers of Formula I or compound 6-g can be performed using standard chiral separation/resolution conditions (e.g., chiral chromatography, crystallization, etc.).

Scheme 7 shows another alternate general synthesis of compounds of Formula I, where LG, m, $R^1$, $R^2$, $R^3$, $R^4$, and $R^5$ are as defined herein.

In Scheme 7, amine 1-c is reacted with appropriately substituted 7-a under nucleophilic substitution conditions, where Lg is a suitable leaving group, such as a halide (e.g., fluoro, chloro, bromo, iodo) or an activated alcohol (e.g., AcO—, TsO-, TfO-, MsO-, etc.) in the presence of a base, to provide compound of Formula I. Alternatively, amine 1-c is reacted with ketone 7-b to provide 7-c, which is subsequently reduced to provide compound of Formula I. Resolution of the isomers of Formula I can be performed using standard chiral separation/resolution conditions (e.g., chiral chromatography, crystallization, etc.).

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

Preparation of Azides from Amines

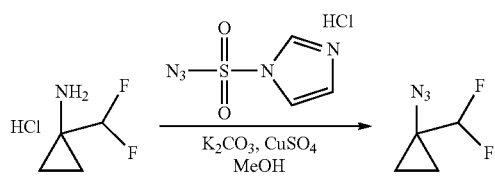 [SMILES: Cl ; Cl ; NC1(C(F)F)CC1 ; [N-]=[N+]=NS(=O)(=O)n1ccnc1 ; [N-]=[N+]=NC1(C(F)F)CC1]

1-(difluoromethyl)cyclopropan-1-amine hydrochloride (175 mg, 1.22 mmol) was added to a suspension of 1H-imidazole-1-sulfonyl azide hydrochloride (307 mg, 1.46 mmol), potassium carbonate (421 mg, 3.05 mmol), and copper (II) sulfate pentahydrate (15 mg, 0.06 mmol) in methanol (2.0 mL). The blue mixture was stirred at room temperature for 24 hours. Acetic acid (183 mg, 3.05 mmol) was added and the mixture used for click chemistry as such. See E. D. Goddard, et. al., Org. Lett., 2007, p. 3797.

Preparation of Azides from Alcohols

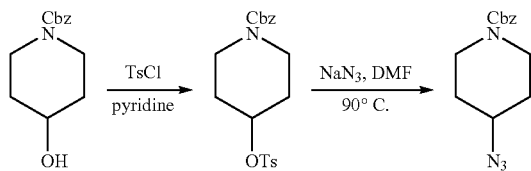

Benzyl 4-(tosyloxy)piperidine-1-carboxylate

Benzyl 4-hydroxypiperidine-1-carboxylate (17.2 g, 73.1 mmol) and p-toluenesulfonyl chloride (15.3 g, 80.4 mmol) were dissolved in pyridine (50 mL) and stirred at room temperature. After 23 hrs, the pyridine was removed under reduced pressure and the residue was dissolved in EtOAc (300 mL). The organic phase was washed with water (2×150 mL) and saturated ammonium chloride (100 mL), dried over sodium sulfate and the solvent was removed under reduced pressure. The residue was subjected to flash chromatography (elutent: ethyl acetate/hexanes). The fractions containing product were combined and the solvent was removed under reduced pressure, providing benzyl 4-(tosyloxy)piperidine-1-carboxylate (20.5 g, 72%).

Benzyl 4-azidopiperidine-1-carboxylate

Sodium azide (2.48 g, 38.2 mmol) was added to a solution of benzyl 4-(tosyloxy)piperidine-1-carboxylate (12.4 g, 31.8 mmol) in dimethylformamide (100 mL). The mixture was heated at 90° C. for 30 minutes. The mixture was cooled and diluted with ethyl acetate (250 mL) and washed with water (2×15 mL), 5% aqueous lithium chloride (10 mL) and brine (10 mL). The organic phase was dried over sodium sulfate and concentrated (NOT to dryness) providing the desired material. The yield was assumed to 100% and all material was used in the next step.

General Procedure 1

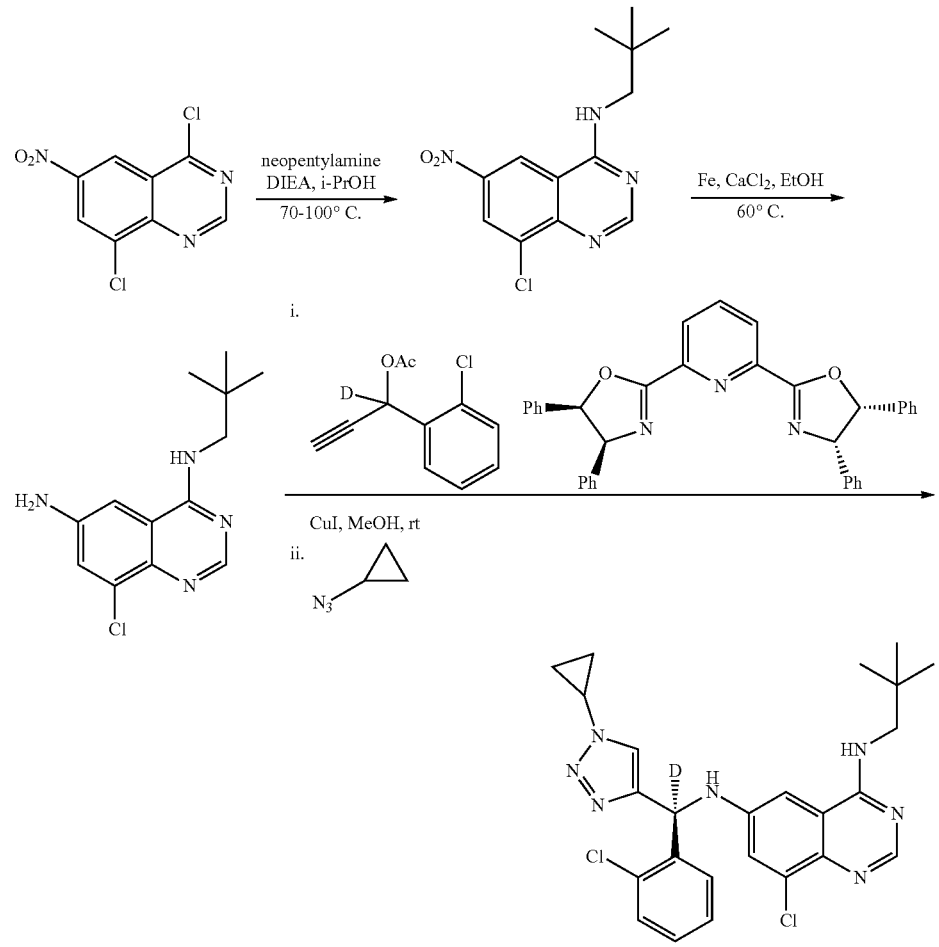

8-chloro-N-neopentyl-6-nitroquinazolin-4-amine 4,8-dichloro-6-nitroquinazoline (200 mg, 0.82 mmol) (Enamine Building Block), neopentylamine (79 mg, 0.90 mmol) and N,N-Diisopropylethylamine (127 mg, 0.98 mmol) in iso-propanol (7 mL) were heated to 90° C. overnight. The reaction was cooled to room temperature and the solvent evaporated. Used in next step as is presuming quantitative yield. ES/MS (M+H$^+$) 295.17.

8-chloro-N4-neopentylquinazoline-4,6-diamine 8-chloro-N-neopentyl-6-nitroquinazolin-4-amine (242 mg, 0.82 mmol), calcium chloride (137 mg, 1.23 mmol), iron powder (137 mg, 2.46 mmol) were heated in ethanol (10 mL)/water (1 mL) at 65° C. overnight. The reaction was cooled to room temperature and solids were removed via filtration. The solids were washed with EtOAc and the combined organic layers were washed with water, brine, and dried over sodium sulfate. Filtration and evaporation of all volatiles yielded the product as the crude amine. ES/MS (M+H$^+$) 265.09.

(S)-8-chloro-N6-((2-chlorophenyl)(1-cyclopropyl-1H-1,2,3-triazol-4-yl)methyl-d)-N4-neopentylquinazoline-4,6-diamine 8-chloro-N4-neopentylquinazoline-4,6-diamine (100 mg, 0.38 mmol), CuI (7 mg, 0.04 mmol) and oxazoline ligand (20 mg, 0.04 mmol) were sonicated in MeOH (3 mL) for ~1 minute. Alkynyl acetate (95 mg, 0.45 mmol) in MeOH (1 mL) and di-isopropyl ethyl amine (81 mg, 0.62 mmol) were added and the reaction was stirred overnight. Azidocyclopropane (19 mg, 0.23 mmol) was added and the reaction was stirred overnight at room temperature. Reaction mixture was filtered over celite and solvents were removed in vacuo. The crude material was purified via RP-HPLC (eluent: water/MeCN*0.1% TFA) to yield the product as a trifluoro acetate salt (19 mg, 0.03 mmol). $^1$H NMR (400 MHz, DMSO-d$_6$) δ 9.39 (s, 1H), 8.51 (s, 1H), 8.07 (s, 1H), 7.63 (d, J=2.2 Hz, 1H), 7.53 (s, 1H), 7.51-7.45 (m, 2H), 7.38-7.29 (m, 3H), 3.96 (td, J=7.3, 3.7 Hz, 1H), 3.64 (dd, J=13.0, 6.6 Hz, 1H), 3.51 (dd, J=12.9, 6.0 Hz, 1H), 1.19-1.04 (m, 4H), 0.92 (s, 9H). ES/MS (M+H$^+$) 497.33.

Alternatively, the product of the initial N-alkylation step can be isolated and subjected to [3+2] cycloaddition reactions in a separate reaction as in example procedures 8 and 9.

General Procedure 2

(S)—N4-(3-chloro-4-fluorophenyl)-N6-((4-chlorophenyl)(1-(piperidin-4-yl)-1H-1,2,3-triazol-4-yl)methyl)quinazoline-4,6-diamine To (S)-tert-butyl 4-(4-(((4-((3-chloro-4-fluorophenyl)amino)quinazolin-6-yl)amino)(4-chlorophenyl)methyl)-1H-1,2,3-triazol-1-yl)piperidine-1-carboxylate (made by general procedure 1; 310 mg, 0.47 mmol) in methylene chloride (5 mL) was added trifluoroacetic acid (1.06 g, 9.34 mmol) slowly. The reaction mixture was stirred at room temperature for 6 hours. The solvent was evaporated and the residue was quenched with saturated sodium bicarbonate. The resulting emulsion was filtered through a pad of celite. Filtrate layers were separated and aqueous layer extracted with methylene chloride (×2). Combined organics washed with brine and dried (Na$_2$SO$_4$). Filtration and evaporation of volatiles gave the crude material which was purified by RP-HPLC (eluent: water/MeCN*0.1% TFA) to yield the product as a trifluoro acetate salt. 1H NMR (400 MHz, DMSO-d$_6$) δ 8.71 (s, 1H), 8.48 (s, 1H), 8.06 (s, 1H), 8.00 (dd, J=6.8, 2.6 Hz, 1H), 7.74-7.61 (m, 3H), 7.59-7.50 (m, 5H), 7.47-7.40 (m, 2H), 6.16 (d, J=8.7 Hz, 1H), 4.86-4.73 (m, 1H), 3.42 (d, J=13.4 Hz, 2H), 3.10 (t, J=11.6 Hz, 2H), 2.27 (d, J=13.2 Hz, 2H), 2.12 (d, J=12.5 Hz, 2H). ES/MS (M+H$^+$) 563.14.

General Procedure 3:

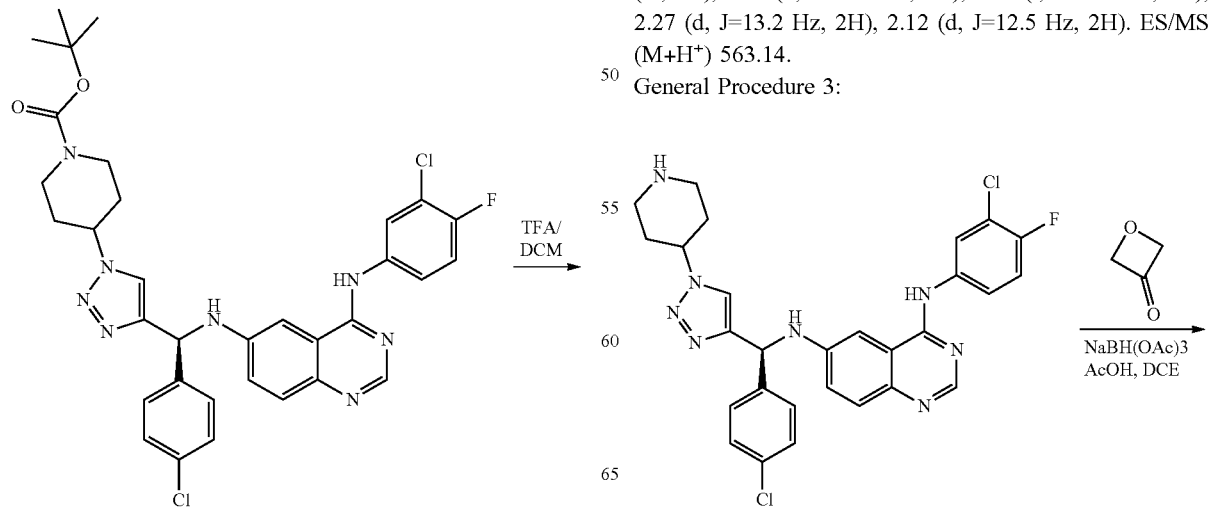

-continued

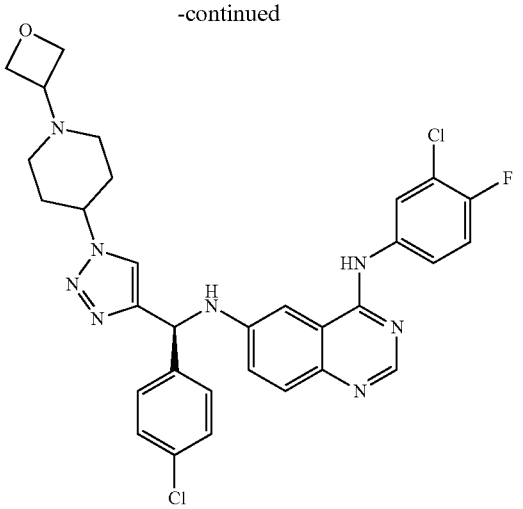

(S)—N4-(3-chloro-4-fluorophenyl)-N6-((4-chlorophenyl)(1-(1-(oxetan-3-yl)piperidin-4-yl)-1H-1,2,3-triazol-4-yl)methyl)quinazoline-4,6-diamine To (S)—N4-(3-chloro-4-fluorophenyl)-N6-((4-chlorophenyl)(1-(piperidin-4-yl)-1H-1,2,3-triazol-4-yl)methyl) quinazoline-4,6-diamine (75 mg, 0.13 mmol) in dichloroethane (1 mL) was added oxetan-3-one (18 mg, 0.25 mmol) and acetic acid (41 mg, 0.68 mmol) followed by sodium triacetoxyborohydride (42 mg, 0.20 mmol). The reaction mixture was stirred at room temperature for two days, quenched with water and extracted into EtOAc (×2). Combined organics were washed with water, brine, dried (Na$_2$SO$_4$) and concentrated to give the crude product, which was purified by silica chromatography (3% NH$_4$OH in MeOH and EtOAc). The product was taken in acetonitrile/water (1 mL/1 mL), frozen and dried on the lyophilizer to give the title compound as a cream solid. 1H NMR (400 MHz, DMSO-d$_6$) δ 9.35 (s, 1H), 8.37 (s, 1H), 8.14 (dd, J=6.9, 2.6 Hz, 1H), 8.09 (s, 1H), 7.77 (ddd, J=9.1, 4.3, 2.6 Hz, 1H), 7.59-7.54 (m, 4H), 7.48-7.38 (m, 5H), 7.33 (d, J=2.4 Hz, 1H), 7.20 (d, J=8.9 Hz, 1H), 6.17 (d, J=8.8 Hz, 1H), 4.54 (t, J=6.5 Hz, 3H), 4.42 (t, J=6.1 Hz, 2H), 1.99 (m, 8H). ES/MS (M+H$^+$) 619.16.

General Procedure 4

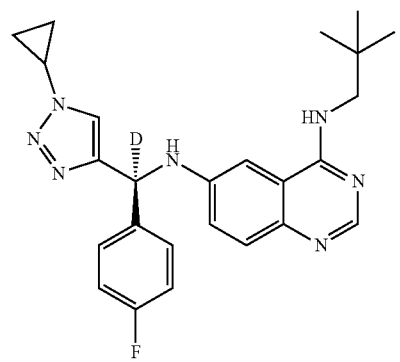

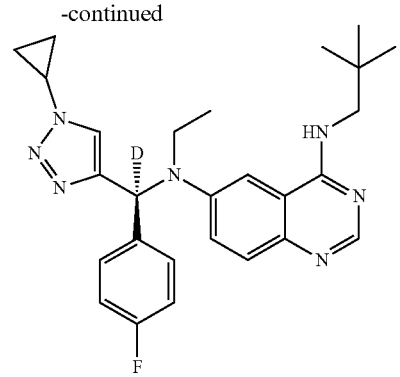

(S)—N6-((1-cyclopropyl-1H-1,2,3-triazol-4-yl)(4-fluorophenyl)methyl-d)-N6-ethyl-N4-neopentylquinazoline-4,6-diamine To (S)—N6-((1-cyclopropyl-1H-1,2,3-triazol-4-yl)(4-fluorophenyl)methyl-d)-N4-neopentylquinazoline-4,6-diamine (made by general procedure 1; 90 mg, 0.20 mmol) was added acetaldehyde (44 mg, 1.01 mmol), acetic acid (24 mg, 0.40 mmol) and sodium triacetoxy borohydride (85 mg, 0.40 mmol) and the reaction was stirred at room temperature overnight. It was then filtered on celite and washed with EtOAc. The filtrate was concentrated and purified by silica gel chromatography (MeOH/EtOAc/hexanes). Desired fractions were concentrated to give the title compound as a yellow solid. 1H NMR (400 MHz, DMSO-d$_6$) δ 8.10 (s, 1H), 7.75 (t, J=6.3 Hz, 1H), 7.44 (s, 3H), 7.38-7.31 (m, 2H), 7.16 (t, J=8.9 Hz, 2H), 4.01-3.94 (m, 1H), 3.54-3.39 (m, 4H), 1.18-1.05 (m, 4H), 0.91 (s, 9H), 0.83 (t, J=6.9 Hz, 3H). ES/MS (M+H$^+$) 475.25.

General Procedure 5

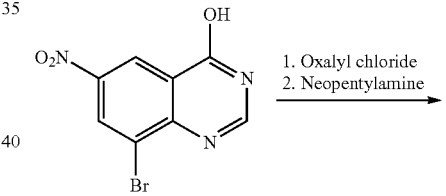

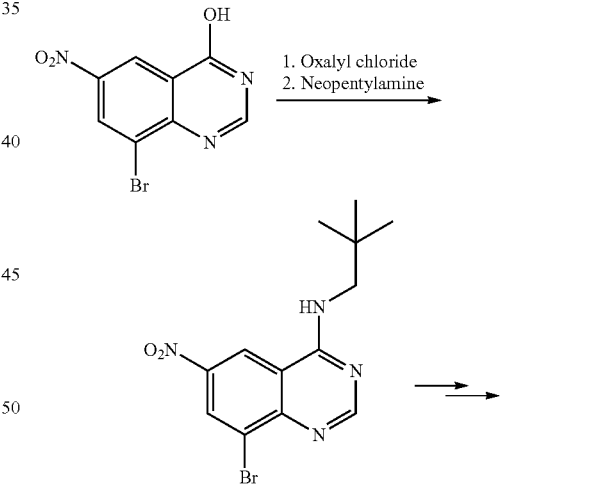

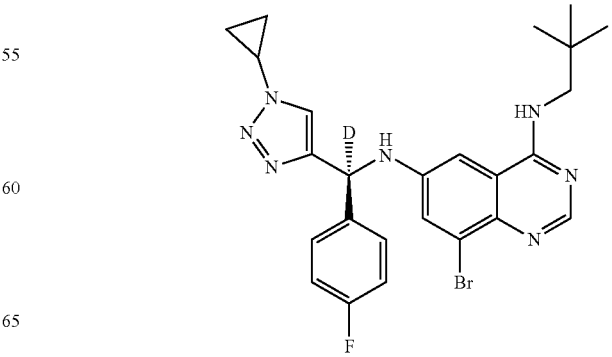

8-bromo-N-neopentyl-6-nitroquinazolin-4-amine

To 8-bromo-6-nitroquinazolin-4-ol (250 mg, 0.93 mmol) in methylene chloride (5 mL) was added DMF (0.5 mL) followed by oxalyl chloride (141 mg, 1.11 mmol) drop wise. After gas evolution ceased, the reaction mixture was capped and heated to 55° C. After 4 hours, the reaction mixture was cooled and neopentyl amine was added (fuming seen). The reaction was heated again to 55° C. overnight. The mixture cooled to room temperature, quenched with water and EtOAc and sat. sodium bicarbonate was added. The organic layer was washed with water, dried ($Na_2SO_4$), filtered and concentrated to give the title compound. ES/MS (M+H$^+$) 339.22.

(S)-8-bromo-N6-((1-cyclopropyl-1H-1,2,3-triazol-4-yl)(4-fluorophenyl)methyl-d)-N4-neopentylquinazoline-4,6-diamine Made by general procedure 1 starting from 8-bromo-N-neopentyl-6-nitroquinazolin-4-amine. 1H NMR (400 MHz, DMSO-d$_6$) δ 8.45 (s, 1H), 8.06 (d, J=1.9 Hz, 1H), 7.82 (d, J=2.3 Hz, 1H), 7.56 (ddd, J=9.3, 5.4, 2.0 Hz, 3H), 7.34 (d, J=2.3 Hz, 1H), 7.16 (td, J=8.9, 2.0 Hz, 2H), 3.96 (td, J=5.5, 4.8, 2.6 Hz, 1H), 3.82-3.74 (m, 1H), 3.40 (d, J=25.3 Hz, 1H), 1.18-1.05 (m, 4H), 0.92 (d, J=1.9 Hz, 9H). ES/MS (M+H+) 525.14.

General Procedure 6

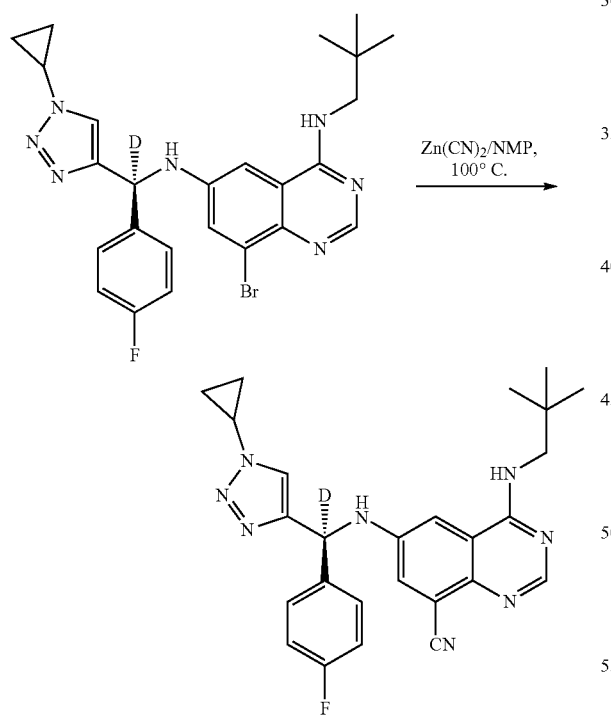

(S)-6-(((1-cyclopropyl-1H-1,2,3-triazol-4-yl)(4-fluorophenyl)methyl-d)amino)-4-(neopentylamino)quinazoline-8-carbonitrile To (S)-8-bromo-N6-((1-cyclopropyl-1H-1,2,3-triazol-4-yl)(4-fluorophenyl)methyl-d)-N4-neopentylquinazoline-4,6-diamine (33 mg, 0.06 mmol) in NMP (0.6 mL) was added zinc cyanide (18 mg, 0.16 mmol) and the mixture degassed and heated at 100° C. overnight. The reaction was quenched with water and extracted into EtOAc (×2). Combined organics were washed with water, brine, dried ($Na_2SO_4$) and concentrated. Crude material was purified by RP-HPLC (eluent: water/MeCN*0.1% TFA) to yield the product as a trifluoro acetate salt. 1H NMR (400 MHz, DMSO-d$_6$) δ 8.30 (d, J=1.9 Hz, 1H), 8.05 (d, J=1.9 Hz, 1H), 7.79 (t, J=2.2 Hz, 1H), 7.59-7.53 (m, 2H), 7.50 (d, J=2.7 Hz, 1H), 7.34 (s, 2H), 7.19-7.12 (m, 2H), 3.94 (d, J=16.8 Hz, 1H), 3.66 (d, J=6.7 Hz, 1H), 3.29 (s, 1H), 1.17-1.05 (m, 4H), 0.91 (d, J=1.9 Hz, 9H). ES/MS (M+H$^+$) 472.30.

Alternative Procedure for Cyanation:

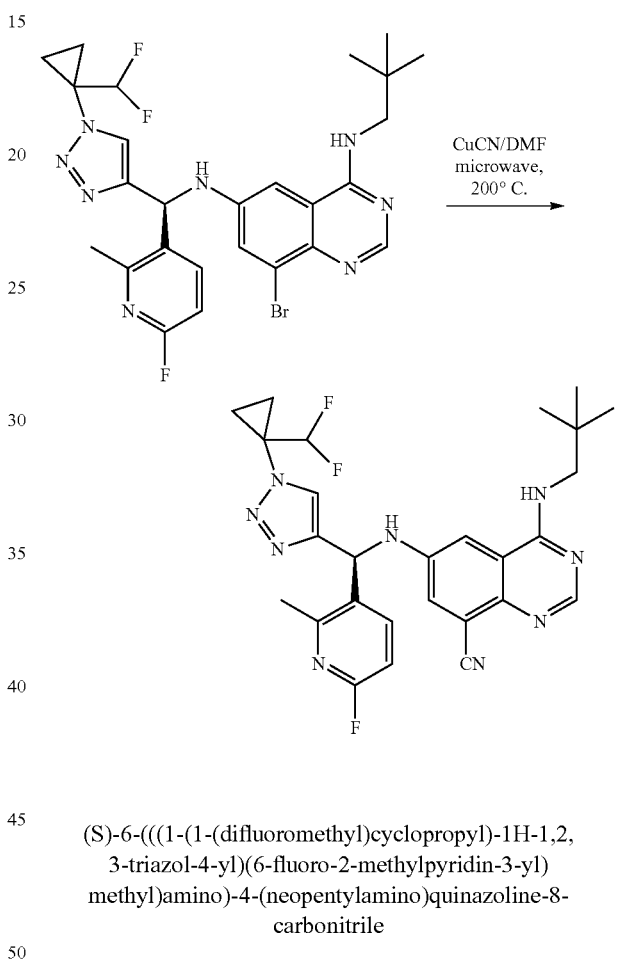

(S)-6-(((1-(1-(difluoromethyl)cyclopropyl)-1H-1,2,3-triazol-4-yl)(6-fluoro-2-methylpyridin-3-yl)methyl)amino)-4-(neopentylamino)quinazoline-8-carbonitrile To (S)-8-bromo-N6-((1-(1-(difluoromethyl)cyclopropyl)-1H-1,2,3-triazol-4-yl)(6-fluoro-2-methylpyridin-3-yl)methyl)-N4-neopentylquinazoline-4,6-diamine (42 mg, 0.07 mmol) in DMF (1.5 mL) was added copper cyanide (32 mg, 0.36 mmol) and the mixture heated in the microwave at 200° C. for 15 minutes. After cooling to room temperature, the reaction was quenched with water and extracted into EtOAc (×2). Combined organics were washed with water, brine, dried ($Na_2SO_4$) and concentrated. Crude material was purified by RP-HPLC (eluent: water/MeCN*0.1% TFA) to yield the product as a trifluoro acetate salt. 1H NMR (400 MHz, DMSO-d$_6$) δ 8.33 (d, J=2.0 Hz, 1H), 8.20 (d, J=2.0 Hz, 1H), 7.83 (d, J=17.0 Hz, 2H), 7.38 (d, J=13.9 Hz, 2H), 6.98 (s, 1H), 6.27-5.93 (m, 2H), 3.32 (s, 2H), 2.50 (s, 3H), 1.50 (s, 4H), 0.87 (t, J=3.7 Hz, 9H). ES/MS (M+H$^+$) 536.30.

General Procedure 7

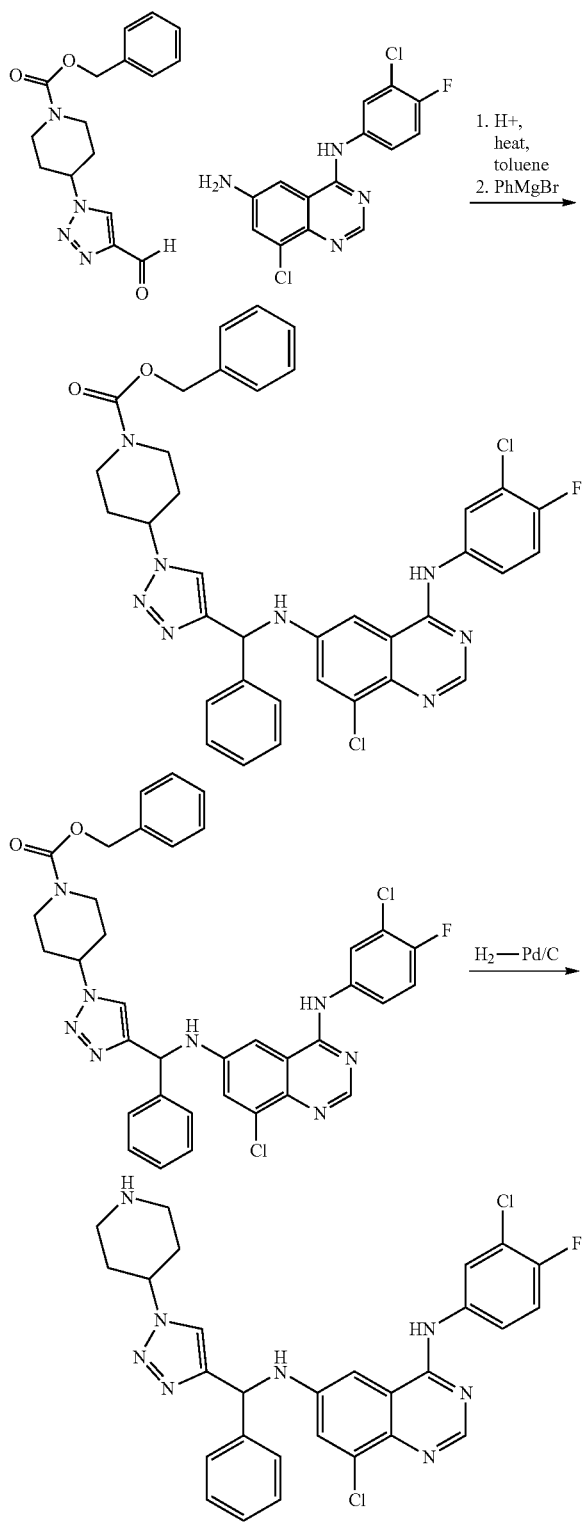

A suspension of the 8-chloro-N4-(3-chloro-4-fluorophenyl)quinazoline-4,6-diamine (130 mg, 0.4 mmol), benzyl 4-(4-formyl-1H-1,2,3-triazol-1-yl)piperidine-1-carboxylate (126.5 mg, 0.4 mmol), and pTSA in toluene was heated at reflux with azeotropic water removal. After 4 hours the solvent was removed under reduced pressure. The solid was dissolved in MeTHF and phenylmagnesium bromide was added. After 60 min, the reaction was quenched with sat NH4Cl (30 mL). The layers were separated and the aqueous phase was extracted with EtOAc. The combined organic phases were washed with brine, dried over sodium sulfate and concentrated. The residue was subjected to flash chromatography (EtOAc/hexanes). The fractions containing product were combined and the solvent was removed to give the product II-1. $^1$H NMR (400 MHz, DMSO-$d_6$) δ 9.84 (s, 1H), 8.45 (s, 1H), 8.04 (m, 2H), 7.69 (m, 2H), 7.52-7.22 (m, 13H), 6.14 (s, 1H), 5.07 (s, 2H), 4.71 (m, 1H), 4.08 (m, 2H), 2.95 (m, 2H), 2.04 (m, 2H), 1.86 (m, 2H).

Benzyl 4-(4-(((8-chloro-4-((3-chloro-4-fluorophenyl)amino)quinazolin-6-yl)amino)(phenyl)methyl)-1H-1,2,3-triazol-1-yl)piperidine-1-carboxylate (32 mg, 0.046 mmol) and Pd—C in EtOH were stirred under and atmosphere of hydrogen. After 4.5 hrs, the reaction mixture was filtered and the volatiles were removed in vacuo and the crude was purified via RP-HPLC (eluent: water/MeCN 0.1% TFA). The product was isolated as TFA salt. 1H NMR (400 MHz, DMSO-$d_6$) δ 9.73 (s, 1H), 8.72 (m, 1H), 8.44 (m, 2H), 8.04 (m, 2H), 7.69 (m, 2H), 7.52-7.22 (m, 9H), 6.17 (m, 1H), 4.77 (m, 1H), 3.39 (m, 2H), 3.06 (m, 2H), 2.24 (m, 2H), 2.10 (m, 2H).

Example Procedure 8

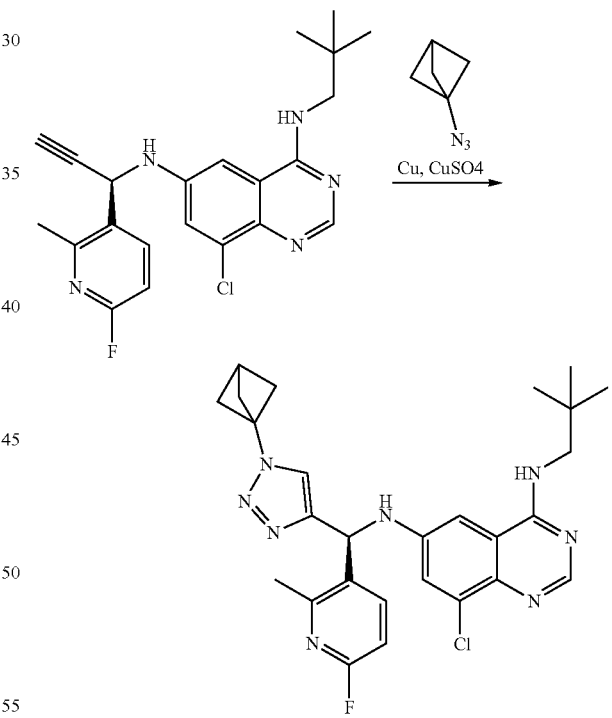

To a solution of (R)-8-chloro-N6-(1-(6-fluoro-2-methylpyridin-3-yl)prop-2-yn-1-yl)-N4-neopentylquinazoline-4,6-diamine (53 mg, 0.13 mmol) in THF was added biclyclo [1.1.1]pentyl-1-azide solution in MeOH, Copper (41 mg) and aqueous copper sulfate solution (0.1 mL) and the suspension was stirred at room temperature. After 1 hr, the reaction mixture was filtered and diluted with EtOAc, washed with saturated aqueous sodium bicarbonate solution, brine, and was dried over sodium sulfate. Filtration and evaporation of volatiles gave the crude reaction product. The material was subjected to RP-chromatography (water/

MeCN*0.1% TFA). The fractions containing product were combined and lyophilized give the product I-26. 1H NMR (400 MHz, Methanol-d4) δ 8.47 (s, 1H), 7.92 (s, 1H), 7.78 (t, J=8.1 Hz, 1H), 7.59 (d, J=2.3 Hz, 1H), 7.04 (d, J=2.3 Hz, 1H), 6.88 (dd, J=8.4, 2.8 Hz, 1H), 6.17 (s, 1H), 3.68 (s, 2H), 2.67 (d, J=17.2 Hz, 1H), 2.52 (s, 3H), 2.37 (s, 6H), 0.96 (s, 9H).

Example Procedure 9

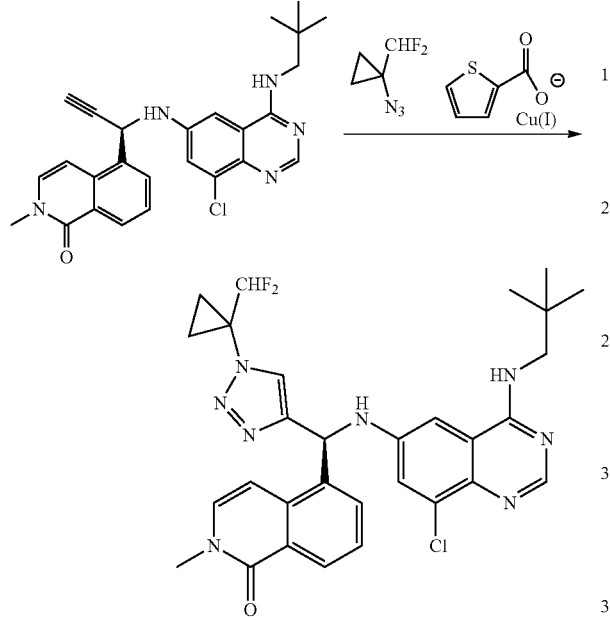

To a solution of (R)-5-(1-((8-chloro-4-(neopentylamino)quinazolin-6-yl)amino)prop-2-yn-1-yl)-2-methylisoquinolin-1(2H)-one (68 mg, 0.15 mmol) in THF was added 1-azido-1-(difluoromethyl)cyclopropane solution in MeOH, copper (I) thiophene carboxylate (5.7 mg) and the reaction was stirred at room temperature. After the reaction was complete, the reaction mixture was filtered and diluted with EtOAc, washed with saturated aqueous sodium bicarbonate solution, brine, and was dried over sodium sulfate. Filtration and evaporation of volatiles gave the crude reaction product. The material was subjected to RP-chromatography (water/MeCN*0.1% TFA). The fractions containing product were combined and lyophilized to give the product I-25. 1H NMR (400 MHz, Methanol-d4) δ 8.45 (s, 1H), 8.35 (d, J=8.1 Hz, 1H), 7.94 (s, 1H), 7.76-7.65 (m, 1H), 7.60 (d, J=2.3 Hz, 1H), 7.49 (t, J=7.8 Hz, 1H), 7.41 (d, J=7.7 Hz, 1H), 7.05 (d, J=2.3 Hz, 1H), 6.83 (d, J=7.7 Hz, 1H), 6.54 (s, 1H), 5.91 (t, J=54.7 Hz, 1H), 3.71 (d, J=13.0 Hz, 1H), 3.63-3.51 (m, 4H), 1.50 (d, J=3.7 Hz, 4H), 0.89 (s, 9H).

Example Procedure 10

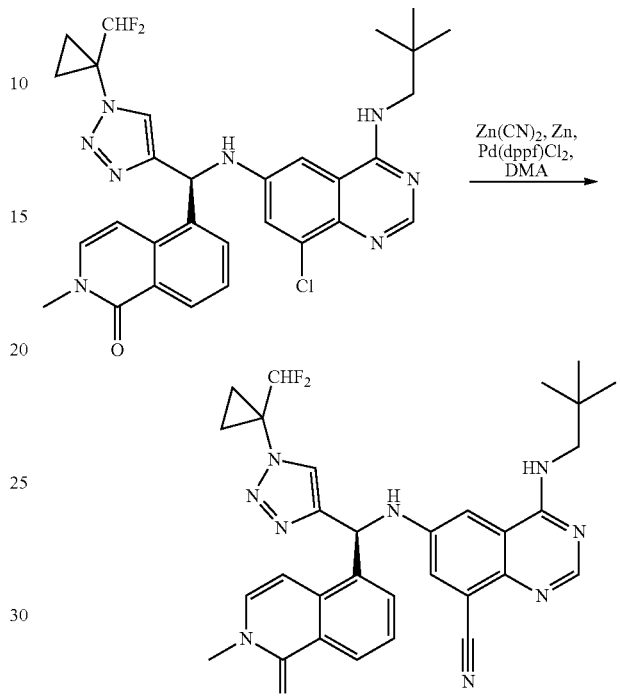

A mixture of (S)-5-(((8-chloro-4-(neopentylamino)quinazolin-6-yl)amino)(1-(1-(difluoromethyl)cyclopropyl)-1H-1,2,3-triazol-4-yl)methyl)-2-methylisoquinolin-1(2H)-one (35 mg, 0.06 mmol), Pd(dppf)Cl$_2$ (1 mg), Zn powder (0.5 mg) and Zn(CN)2 (69 mg) in dimethyl acetamide was purged with argon and heated at 200° C. in for 15 minutes in a microwave reactor. The reaction mixture was filtered and the crude reaction was purified via RP-HPLC purification (eluent: water/MeCN*0.1% TFA). The product containing fractions were combined and lyophilized to give the product. 1H NMR (400 MHz, DMSO-d$_6$) δ 8.44 (s, 1H), 8.34 (d, J=8.1 Hz, 1H), 7.96 (s, 1H), 7.84 (d, J=2.5 Hz, 1H), 7.71 (dd, J=7.5, 1.2 Hz, 1H), 7.49 (t, J=7.8 Hz, 1H), 7.41 (d, J=7.7 Hz, 1H), 7.32 (d, J=2.5 Hz, 1H), 6.83 (d, J=7.6 Hz, 1H), 6.56 (s, 1H), 5.91 (t, J=54.7 Hz, 1H), 3.67 (d, J=13.1 Hz, 1H), 3.60 (s, 3H), 3.53 (d, J=13.1 Hz, 1H), 1.50 (d, J=3.6 Hz, 4H), 0.88 (s, 9H).

Example Procedure 11

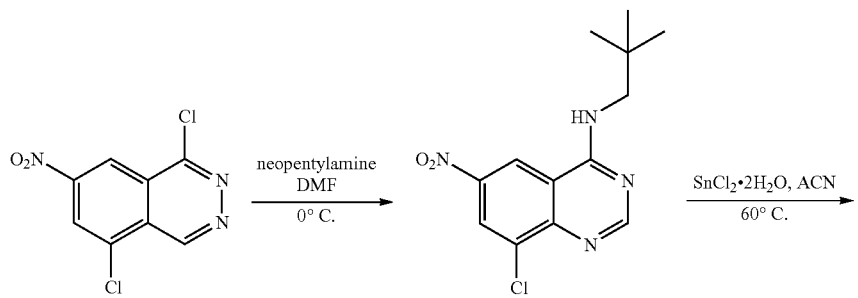

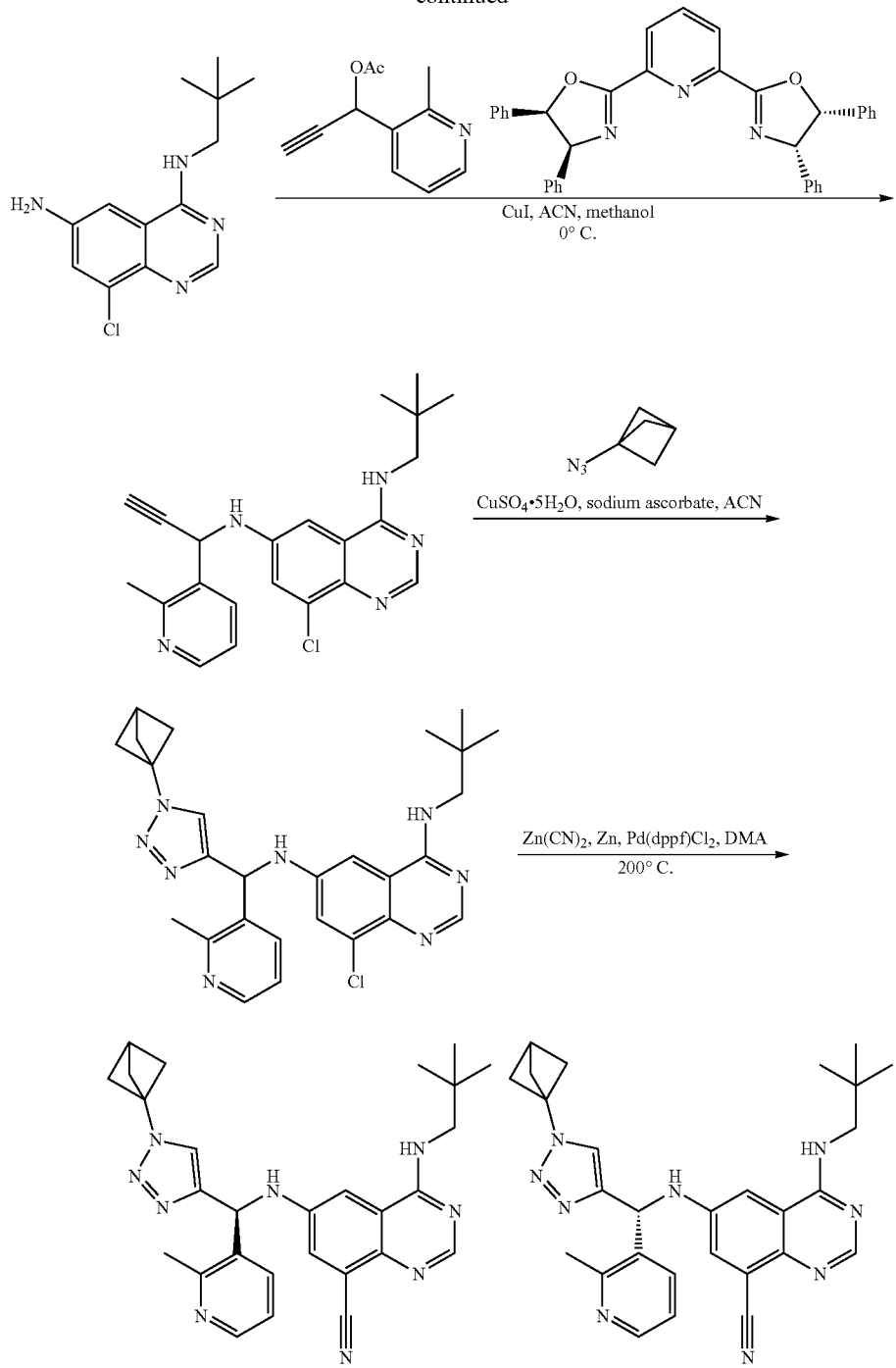

8-chloro-N4-neopentylquinazoline-4,6-diamine 8-chloro-N-neopentyl-6-nitroquinazolin-4-amine To a solution of 4,8-dichloro-6-nitroquinazoline (0.52 g, 2.13 mmol) in DMF (3 ml) was added dropwise neopentylamine (0.5 ml, 4.26 mmol) at 0° C. The mixture was warmed to room temperature and stirred for 1 hour. The product was precipitated from water (30 mL) and the solids were filtered, washed with water, and dried under vacuum. The crude product was taken to next step without further purification. ES/MS (M+H$^+$) 295.41.

To a solution of 4,8-dichloro-6-nitroquinazoline in acetonitrile (5 ml) was added tin(II) chloride dihydrate (2.17 g, 9.62 mmol). After stirring for 1.5 hours at 60° C., 0.5M NaOH (aq, 50 ml) was added and the product was extracted with dichloromethane (2×25 ml). The organic layers were washed with water (50 ml), dried with anhydrous sodium sulfate, filtered, and concentrated. The product was purified by silica chromatography using EtOAc in hexane to give the title compound (360 mg). ES/MS (M+H$^+$) 265.42.

8-chloro-N6-(1-(2-methylpyridin-3-yl)prop-2-yn-1-yl)-N4-neopentylquinazoline-4,6-diamine A suspension of CuI (12.95 mg, 0.07 mmol) and oxazoline ligand (53.19 mg, 0.1 mmol) in methanol (2 ml) and acetonitrile (2 ml) was sonicated for 5 minutes. To the stirring solution was added 8-chloro-N4-neopentylquinazoline-4,6-diamine (360 mg, 1.36 mmol), followed by 1-(2-methylpyridin-3-yl)prop-2-yn-1-yl acetate (308.74 mg, 1.63 mmol), and N,N-diisopropylethylamine (355.26 µl, 2.04 mmol). After stirring at 5° C. for 24 hours, the mixture was filtered through celite and concentrated. The crude mixture was extracted with 2-methyltetrahydrofuran and water. The organic layer was dried with anhydrous sodium sulfate, filtered, and concentrated. The product was purified by silica chromatography using ethyl acetate in hexanes to give the title compound (360 mg). ES/MS (M+H$^+$) 394.68.

N6-((1-(bicyclo[1.1.1]pentan-1-yl)-1H-1,2,3-triazol-4-yl)(2-methylpyridin-3-yl)methyl)-8-chloro-N4-neopentylquinazoline-4,6-diamine To a solution of 1-azidobicyclo[1.1.1]pentane (25.92 mg, 0.24 mmol) in acetonitrile (2 ml) was added 8-chloro-N6-(1-(2-methylpyridin-3-yl)prop-2-yn-1-yl)-N4-neopentylquinazoline-4,6-diamine (115 mg, 0.29 mmol) followed by copper(II) sulfate pentahydrate (72.98 mg, 0.29 mmol), sodium ascorbate (11.56 mg, 0.06 mmol) and water (0.4 ml). The mixture was sonicated for 30 minutes, diluted with 2:1 Hexane:EtOAc (5 ml) and water (10 mL). The mixture was vigorously stirred and filtered. The solids were dissolved in acetonitrile (15 mL), concentrated, and dried under vacuum. The product was purified purified via RP-HPLC purification (eluent: water/MeCN*0.1% TFA) to give the title compound (41 mg). ES/MS (M+H$^+$) 503.62.

(S)-6-(((1-(bicyclo[1.1.1]pentan-1-yl)-1H-1,2,3-triazol-4-yl)(2-methylpyridin-3-yl)methyl)amino)-4-(neopentylamino)quinazoline-8-carbonitrile and (R)-6-(((1-(bicyclo[1.1.1]pentan-1-yl)-1H-1,2,3-triazol-4-yl)(2-methylpyridin-3-yl)methyl)amino)-4-(neopentylamino)quinazoline-8-carbonitrile To a solution of N6-((1-(bicyclo[1.1.1]pentan-1-yl)-1H-1,2,3-triazol-4-yl)(2-methylpyridin-3-yl)methyl)-8-chloro-N4-neopentylquinazoline-4,6-diamine (40 mg, 79.51 µmol) in N,N-dimethylacetamide (0.5 ml) was added Pd(dppf)Cl$_2$ (2.3 mg, 3.2 µmol), Zn powder (1.0 mg, 16.0 µmol), and Zn(CN)$_2$ (11.2 mg, 95.4 µmol). Argon was bubbled through the mixture, sealed, and heated in a microwave reactor at 200° C. for 30 minutes. The product was purified purified via RP-HPLC purification (eluent: water/MeCN*0.1% TFA) to give the title compound. The enantiomers were separated by chiral supercritical fluid chromatography using CHIRALCEL®OD-H/SFC, 5 um 21×250 mm (eluent: 30% ethanol).

First eluting peak: (S)-6-(((1-(bicyclo[1.1.1]pentan-1-yl)-1H-1,2,3-triazol-4-yl)(2-methylpyridin-3-yl)methyl)amino)-4-(neopentylamino)quinazoline-8-carbonitrile. 1H NMR (400 MHz, Methanol-d4) δ 8.51 (d, J=5.2 Hz, 1H), 8.34 (s, 1H), 8.06 (d, J=7.9 Hz, 1H), 8.01 (s, 1H), 7.74 (d, J=2.5 Hz, 1H), 7.53 (dd, J=7.9, 5.2 Hz, 1H), 7.27 (d, J=2.5 Hz, 1H), 6.28 (s, 1H), 3.55 (s, 2H), 2.69 (s, 1H), 2.69 (s, 3H), 2.38 (s, 6H), 0.94 (s, 9H). ES/MS (M+H$^+$) 494.54.

Second eluting peak: (R)-6-(((1-(bicyclo[1.1.1]pentan-1-yl)-1H-1,2,3-triazol-4-yl)(2-methylpyridin-3-yl)methyl)amino)-4-(neopentylamino)quinazoline-8-carbonitrile. $^1$H NMR (400 MHz, Methanol-d4) δ 8.48 (s, 1H), 8.33 (s, 1H), 8.04-7.95 (m, 2H), 7.73 (d, J=2.5 Hz, 1H), 7.49 (dd, J=7.9, 5.2 Hz, 1H), 7.25 (s, 1H), 6.27 (s, 1H), 3.54 (d, J=1.4 Hz, 2H), 2.69 (s, 1H), 2.68 (s, 3H), 2.38 (s, 6H), 0.93 (s, 9H). ES/MS (M+H$^+$) 494.61.

Example Procedure 12

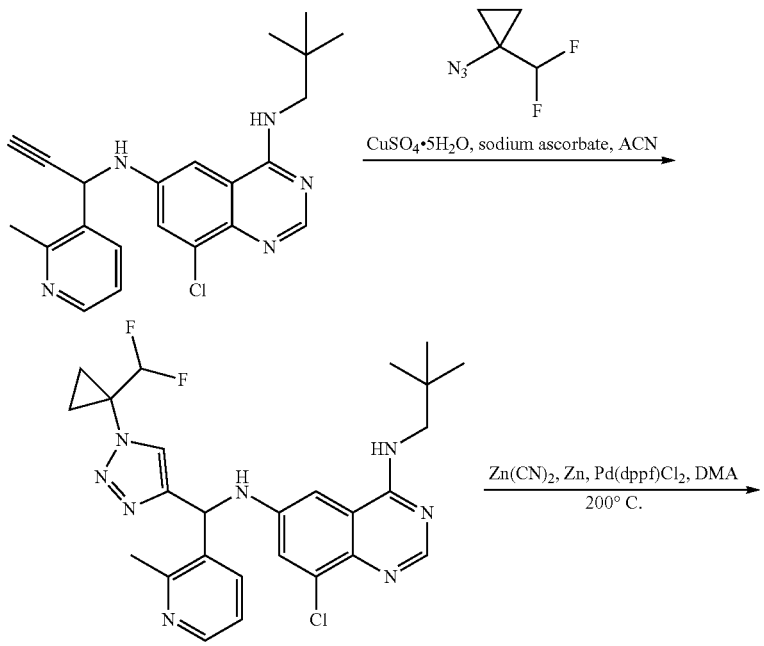

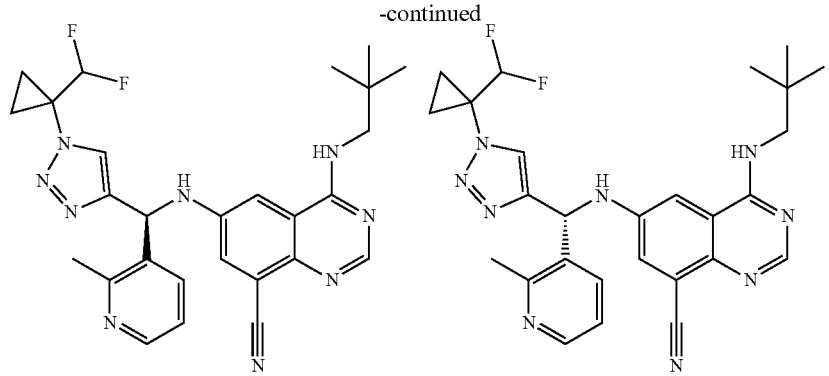

8-chloro-N6-((1-(1-(difluoromethyl)cyclopropyl)-1H-1,2,3-triazol-4-yl)(2-methylpyridin-3-yl)methyl)-N4-neopentylquinazoline-4,6-diamine To a solution of 1-1-azido-1-(difluoromethyl)cyclopropane (31.62 mg, 0.24 mmol) in acetonitrile (2 ml) was added 8-chloro-N6-(1-(2-methylpyridin-3-yl)prop-2-yn-1-yl)-N4-neopentylquinazoline-4,6-diamine (115 mg, 0.29 mmol) followed by copper(II) sulfate pentahydrate (72.98 mg, 0.29 mmol), sodium ascorbate (11.56 mg, 0.06 mmol) and water (0.4 ml). The mixture was sonicated for 30 minutes, diluted with 2:1 Hexane:EtOAc (5 ml) and water (10 mL). The mixture was vigorously stirred and filtered. The solids were dissolved in acetonitrile (15 mL), concentrated, and dried under vacuum. The product was purified purified via RP-HPLC purification (eluent: water/MeCN*0.1% TFA) to give the title compound (24 mg). ES/MS (M+H$^+$) 527.56.

The following compounds were prepared according to the Examples and Procedures described herein (and indicated in Table 1A and Table 1B under Example/Procedure) using the appropriate starting material(s) and appropriate protecting group chemistry as needed.

TABLE 1A

| Cmpd | Structure | Name | Example Procedure | ES/MS m/z (M + H+) |
|---|---|---|---|---|
| I-1 | 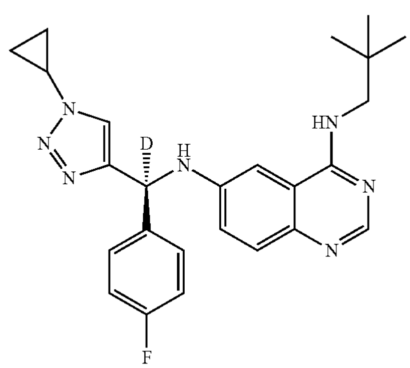 | (S)-N$^6$-((1-cyclopropyl-1H-1,2,3-triazol-4-yl)(4-fluorophenyl)methyl-d)-N$^4$-neopentylquinazoline-4,6-diamine | 1 | 447.2 |
| I-2 | 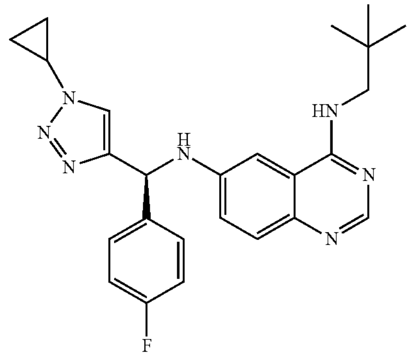 [SMILES: CC(C)(C)CNc1ncnc2ccc(N[C@@H](c3ccc(F)cc3)c3cn(C4CC4)nn3)cc12] | (S)-N$^6$-((1-cyclopropyl-1H-1,2,3-triazol-4-yl)(4-fluorophenyl)methyl)-N$^4$-neopentylquinazoline-4,6-diamine | 1 | 446.2 |

TABLE 1A-continued

| Cmpd | Structure | Name | Example Procedure | ES/MS m/z (M + H+) |
|---|---|---|---|---|
| I-3 | 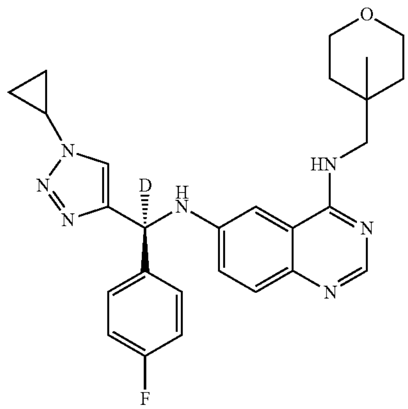 | (S)-N$^6$-((1-cyclopropyl-1H-1,2,3-triazol-4-yl)(4-fluorophenyl)methyl-d)-N$^4$-((4-methyltetrahydro-2H-pyran-4-yl)methyl)quinazoline-4,6-diamine | 1 | 489.26 |
| I-4 | 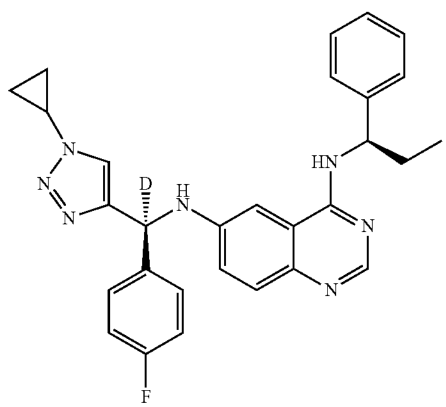 | N$^6$-((S)-(1-cyclopropyl-1H-1,2,3-triazol-4-yl)(4-fluorophenyl)methyl-d)-N$^4$-((R)-1-phenylpropyl)quinazoline-4,6-diamine | 1 | 495.36 |
| I-5 | 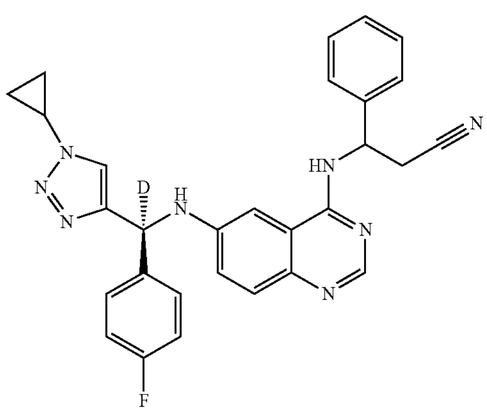 | 3-((6-(((S)-(1-cyclopropyl-1H-1,2,3-triazol-4-yl)(4-fluorophenyl)methyl-d)amino)quinazolin-4-yl)amino)-3-phenylpropanenitrile | 1 | 506.41 |
| I-6 | 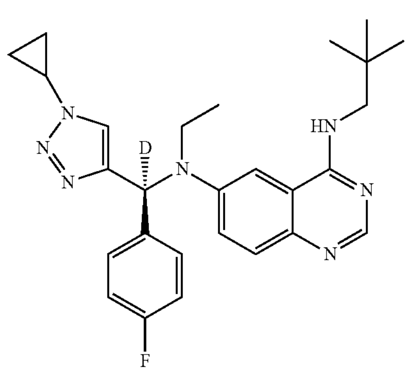 | (S)-N6-((1-cyclopropyl-1H-1,2,3-triazol-4-yl)(4-fluorophenyl)methyl-d)-N6-ethyl-N4-neopentylquinazoline-4,6-diamine | 4 | 475.25 |

TABLE 1A-continued

| Cmpd | Structure | Name | Example Procedure | ES/MS m/z (M + H+) |
|---|---|---|---|---|
| I-7 | 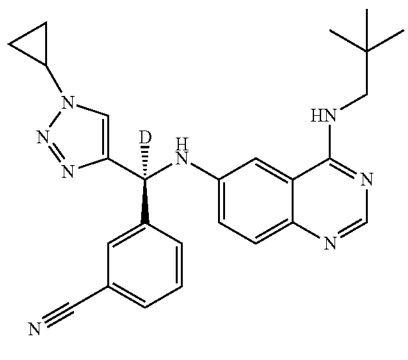 | (S)-3-((1-cyclopropyl-1H-1,2,3-triazol-4-yl)((4-(neopentylamino)quinazolin-6-yl)amino)methyl-d)benzonitrile | 1 | 454.29 |
| I-8 | 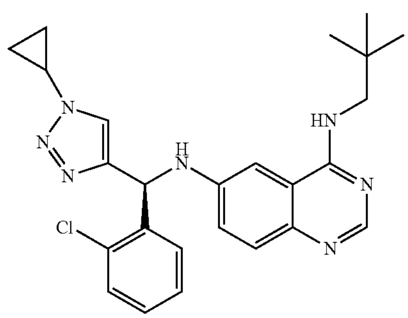 [SMILES: CC(C)(C)CNc1ncnc2ccc(N[C@H](c3cn(C4CC4)nn3)c3ccccc3Cl)cc12] | (S)-$N^6$-((2-chlorophenyl)(1-cyclopropyl-1H-1,2,3-triazol-4-yl)methyl)-$N^4$-neopentylquinazoline-4,6-diamine | 1 | 462.35 |
| I-9 | 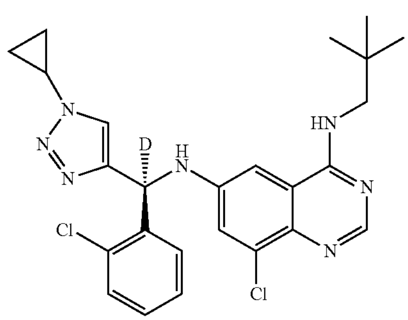 | (S)-8-chloro-N6-((2-chlorophenyl)(1-cyclopropyl-1H-1,2,3-triazol-4-yl)methyl-d)-N4-neopentylquinazoline-4,6-diamine | 1 | 497.33 |
| I-10 | 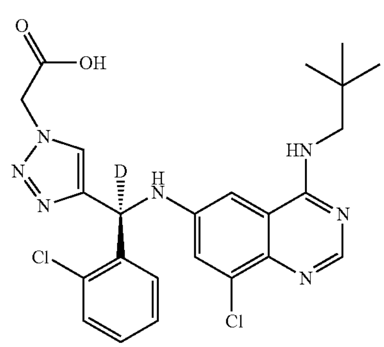 | (S)-2-(4-(((8-chloro-4-(neopentylamino)quinazolin-6-yl)amino)(2-chlorophenyl)methyl-d)-1H-1,2,3-triazol-1-yl)acetic acid | 1 | 515.34 |

TABLE 1A-continued

| Cmpd | Structure | Name | Example Procedure | ES/MS m/z (M + H+) |
|---|---|---|---|---|
| I-11 | 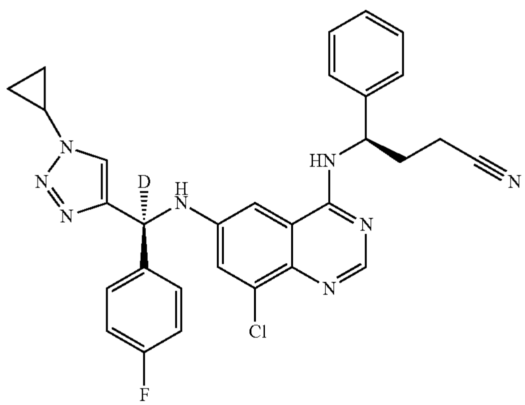 | (R)-4-((8-chloro-6-(((S)-(1-cyclopropyl-1H-1,2,3-triazol-4-yl)(4-fluorophenyl)methyl-d)amino)quinazolin-4-yl)amino)-4-phenylbutanenitrile | 1 | 553.98 |
| I-12 | 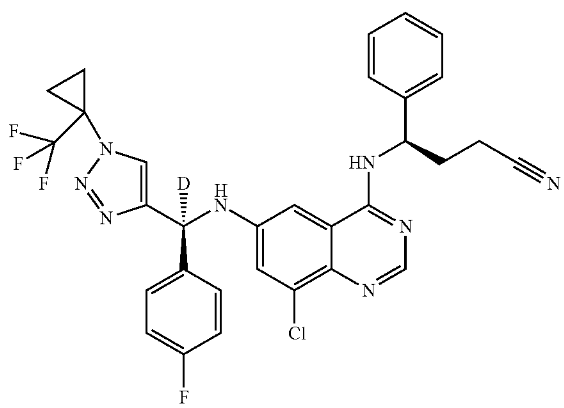 | (R)-4-((8-chloro-6-(((S)-(4-fluorophenyl)(1-(1-(trifluoromethyl)cyclopropyl)-1H-1,2,3-triazol-4-yl)methyl-d)amino)quinazolin-4-yl)amino)-4-phenylbutanenitrile | 1 | 621.96 |
| I-13 | 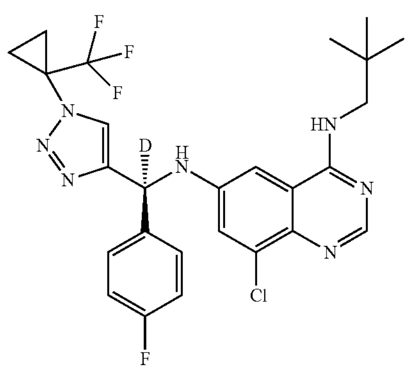 | (S)-8-chloro-N$^6$-((4-fluorophenyl)(1-(1-(trifluoromethyl)cyclopropyl)-1H-1,2,3-triazol-4-yl)methyl-d)-N$^4$-neopentylquinazoline-4,6-diamine | 1 | 549.37 |
| I-14 | 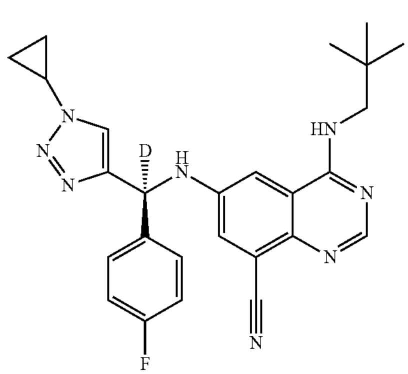 | (S)-6-(((1-cyclopropyl-1H-1,2,3-triazol-4-yl)(4-fluorophenyl)methyl-d)amino)-4-(neopentylamino)quinazoline-8-carbonitrile | 6 | 472.3 |

TABLE 1A-continued

| Cmpd | Structure | Name | Example Procedure | ES/MS m/z (M + H+) |
|---|---|---|---|---|
| I-15 | 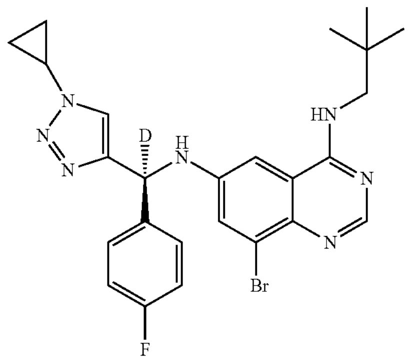 | (S)-8-bromo-N6-((1-cyclopropyl-1H-1,2,3-triazol-4-yl)(4-fluorophenyl)methyl-d)-N4-neopentylquinazoline-4,6-diamine | 5 | 525.14 |
| I-16 | 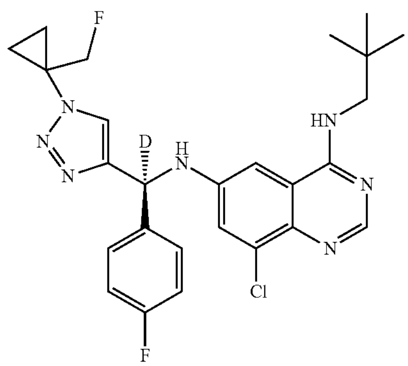 | (S)-8-chloro-$N^6$-((1-(1-(fluoromethyl)cyclopropyl)-1H-1,2,3-triazol-4-yl)(4-fluorophenyl)methyl-d)-$N^4$-neopentylquinazoline-4,6-diamine | 1 | 512.97 |
| I-17 | 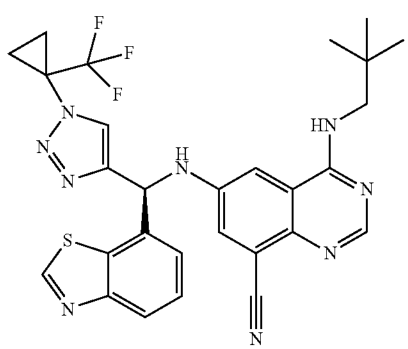 [SMILES: CC(C)(C)CNc1ncnc2c(C#N)cc(N[C@H](c3cn(C4(C(F)(F)F)CC4)nn3)c3cccc4ncsc34)cc12] | (S)-6-((benzo[d]thiazol-7-yl(1-(1-(trifluoromethyl)cyclopropyl)-1H-1,2,3-triazol-4-yl)methyl)amino)-4-(neopentylamino)quinazoline-8-carbonitrile | 6 | 578.21 |
| I-18 | 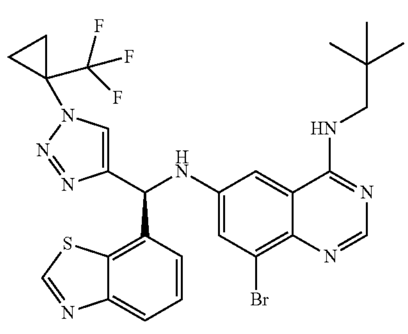 [SMILES: CC(C)(C)CNc1ncnc2c(Br)cc(N[C@H](c3cn(C4(C(F)(F)F)CC4)nn3)c3cccc4ncsc34)cc12] | (S)-$N^6$-(benzo[d]thiazol-7-yl(1-(1-(trifluoromethyl)cyclopropyl)-1H-1,2,3-triazol-4-yl)methyl)-8-bromo-N4-neopentylquinazoline-4,6-diamine | 5 | 631.20 |

TABLE 1A-continued

| Cmpd | Structure | Name | Example Procedure | ES/MS m/z (M + H+) |
|---|---|---|---|---|
| I-19 | 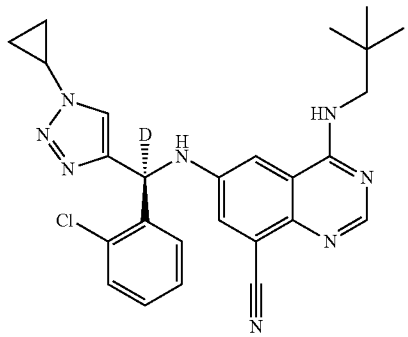 | (S)-6-(((2-chlorophenyl)(1-cyclopropyl-1H-1,2,3-triazol-4-yl)methyl-d)amino)-4-(neopentylamino)quinazoline-8-carbonitrile | 6 | 488.30 |
| I-20 | 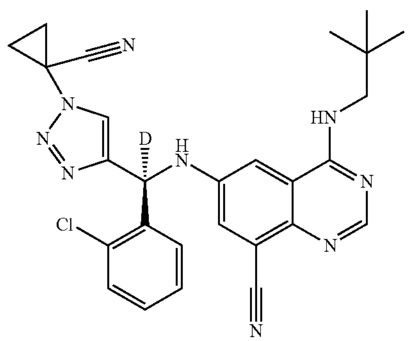 | (S)-6-(((2-chlorophenyl)(1-(1-cyanocyclopropyl)-1H-1,2,3-triazol-4-yl)methyl-d)amino)-4-(neopentylamino)quinazoline-8-carbonitrile | 6 | 513.31 |
| I-21 | 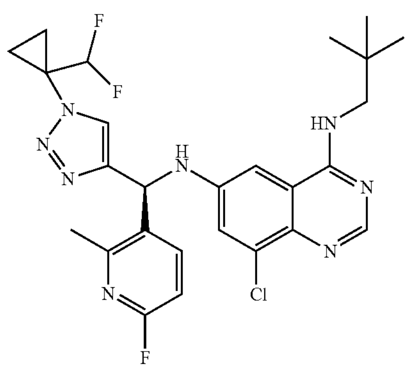 [SMILES: Cc1nc(F)ccc1[C@H](Nc1cc(Cl)c2ncnc(NCC(C)(C)C)c2c1)c1cn(C2(C(F)F)CC2)nn1] | (S)-8-chloro-$N^6$-((1-(1-(difluoromethyl)cyclopropyl)-1H-1,2,3-triazol-4-yl)(6-fluoro-2-methylpyridin-3-yl)methyl)-$N^4$-neopentylquinazoline-4,6-diamine | 1 | 545.17 |
| I-22 | 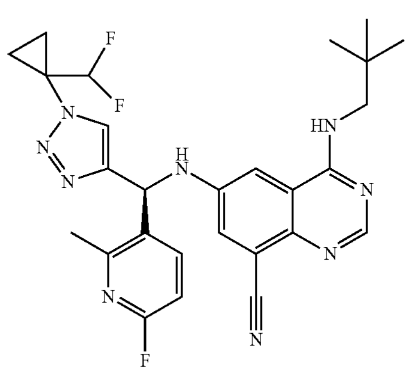 [SMILES: Cc1nc(F)ccc1[C@H](Nc1cc(C#N)c2ncnc(NCC(C)(C)C)c2c1)c1cn(C2(C(F)F)CC2)nn1] | (S)-6-(((1-(1-(difluoromethyl)cyclopropyl)-1H-1,2,3-triazol-4-yl)(6-fluoro-2-methylpyridin-3-yl)methyl)amino)-4-(neopentylamino)quinazoline-8-carbonitrile | 6 | 536.30 |

| Cmpd | Structure | Name | Example Procedure | ES/MS m/z (M + H+) |
|---|---|---|---|---|
| I-23 | 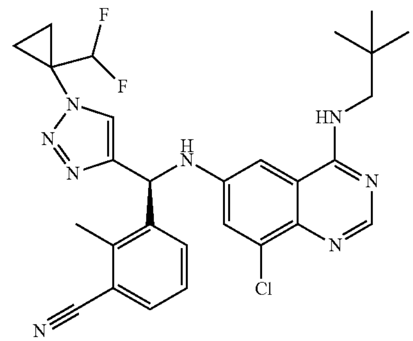 [SMILES: Cc1c(C#N)cccc1[C@H](Nc1cc(Cl)c2ncnc(NCC(C)(C)C)c2c1)c1cn(C2(C(F)F)CC2)nn1] | (S)-3-(((8-chloro-4-(neopentylamino)quinazolin-6-yl)amino)(1-(1-(difluoromethyl)cyclopropyl)-1H-1,2,3-triazol-4-yl)methyl)-2-methylbenzonitrile | 9 | 551.51 |
| I-24 | 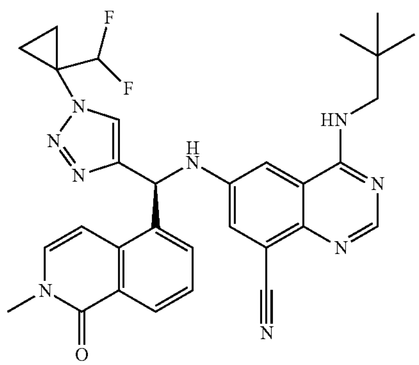 [SMILES: Cn1ccc2c([C@H](Nc3cc(C#N)c4ncnc(NCC(C)(C)C)c4c3)c3cn(C4(C(F)F)CC4)nn3)cccc2c1=O] | (S)-6-(((1-(1-(difluoromethyl)cyclopropyl)-1H-1,2,3-triazol-4-yl)(2-methyl-1-oxo-1,2-dihydroisoquinolin-5-yl)methyl)amino)-4-(neopentylamino)quinazoline-8-carbonitrile | 10 | 584.28 |
| I-25 | 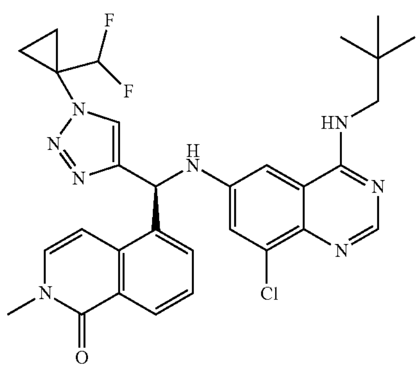 [SMILES: Cn1ccc2c([C@H](Nc3cc(Cl)c4ncnc(NCC(C)(C)C)c4c3)c3cn(C4(C(F)F)CC4)nn3)cccc2c1=O] | (S)-5-(((8-chloro-4-(neopentylamino)quinazolin-6-yl)amino)(1-(1-(difluoromethyl)cyclopropyl)-1H-1,2,3-triazol-4-yl)methyl)-2-methylisoquinolin-1(2H)-one | 9 | 593.4 |
| I-26 | 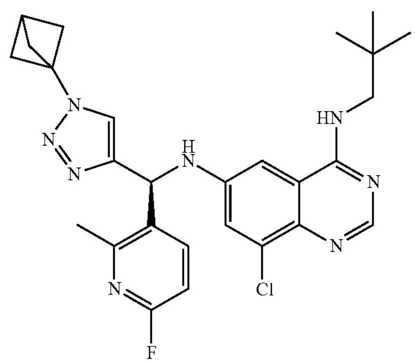 [SMILES: Cc1nc(F)ccc1[C@H](Nc1cc(Cl)c2ncnc(NCC(C)(C)C)c2c1)c1cn(C23CC(C2)C3)nn1] | (S)-N6-((1-(bicyclo[1.1.1]pentan-1-yl)-1H-1,2,3-triazol-4-yl)(6-fluoro-2-methylpyridin-3-yl)methyl)-8-chloro-N4-neopentylquinazoline-4,6-diamine | 8 | 521.4 |

TABLE 1A-continued

| Cmpd | Structure | Name | Example Procedure | ES/MS m/z (M + H+) |
|---|---|---|---|---|
| I-27 | 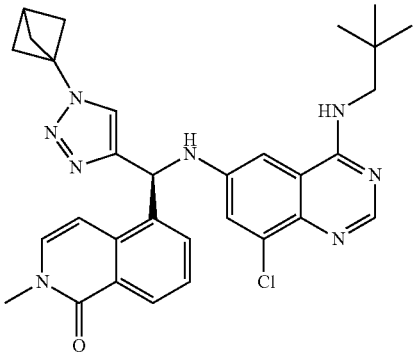 [SMILES: Cn1ccc2c([C@H](Nc3cc(Cl)c4ncnc(NCC(C)(C)C)c4c3)c3cn(C45CC(C4)C5)nn3)cccc2c1=O] | (S)-5-((1-(bicyclo[1.1.1]pentan-1-yl)-1H-1,2,3-triazol-4-yl)((8-chloro-4-(neopentylamino)quinazolin-6-yl)amino)methyl)-2-methylisoquinolin-1(2H)-one | 8 | 569.29 |

TABLE 1B

| Cmpd | Structure | Name | Example Procedure | ES/MS m/z (M + H+) |
|---|---|---|---|---|
| II-1 | 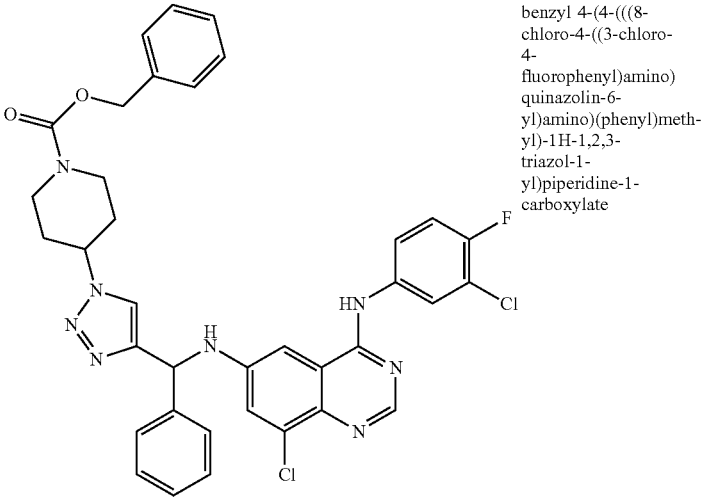 | benzyl 4-(4-(((8-chloro-4-((3-chloro-4-fluorophenyl)amino)quinazolin-6-yl)amino)(phenyl)methyl)-1H-1,2,3-triazol-1-yl)piperidine-1-carboxylate | 7 | |
| II-2 | 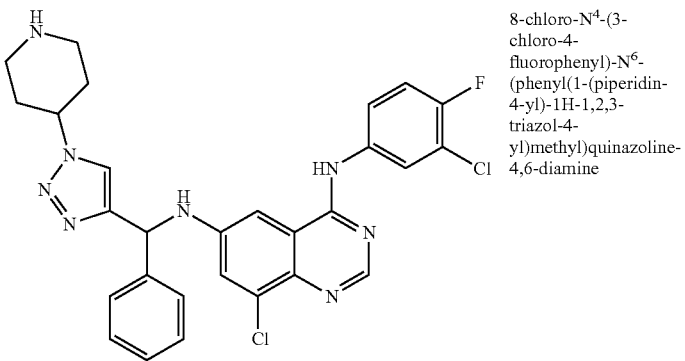 | 8-chloro-$N^4$-(3-chloro-4-fluorophenyl)-$N^6$-(phenyl(1-(piperidin-4-yl)-1H-1,2,3-triazol-4-yl)methyl)quinazoline-4,6-diamine | 7 | |

TABLE 1B-continued

| Cmpd | Structure | Name | Example Procedure | ES/MS m/z (M + H+) |
|---|---|---|---|---|
| II-3 | 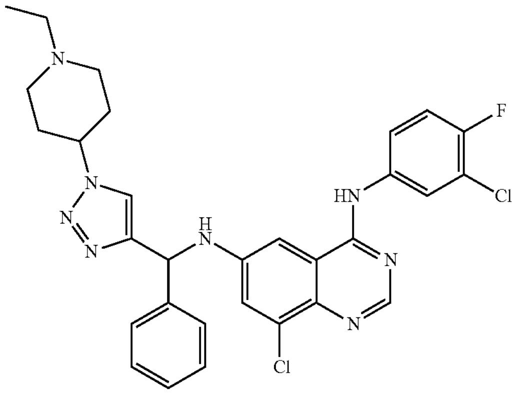 [SMILES: CCN1CCC(n2cc(C(Nc3cc(Cl)c4ncnc(Nc5ccc(F)c(Cl)c5)c4c3)c3ccccc3)nn2)CC1] | 8-chloro-$N^4$-(3-chloro-4-fluorophenyl)-$N^6$-((1-(1-ethylpiperidin-4-yl)-1H-1,2,3-triazol-4-yl)(phenyl)methyl)quinazoline-4,6-diamine | 3 | |
| II-4 | 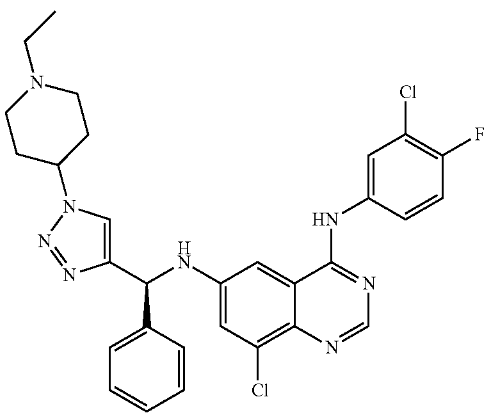 [SMILES: CCN1CCC(n2cc([C@@H](Nc3cc(Cl)c4ncnc(Nc5ccc(F)c(Cl)c5)c4c3)c3ccccc3)nn2)CC1] | (S)-8-chloro-$N^4$-(3-chloro-4-fluorophenyl)-$N^6$-((1-(1-ethylpiperidin-4-yl)-1H-1,2,3-triazol-4-yl)(phenyl)methyl)quinazoline-4,6-diamine | 3 | |
| II-5 | 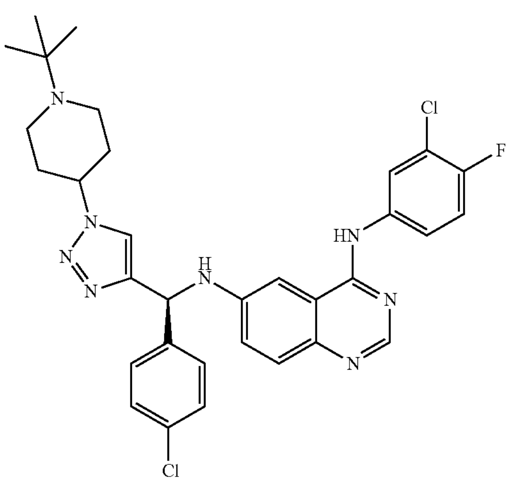 [SMILES: CC(C)(C)N1CCC(n2cc([C@@H](Nc3ccc4ncnc(Nc5ccc(F)c(Cl)c5)c4c3)c3ccc(Cl)cc3)nn2)CC1] | (S)-$N^6$-((1-(1-(tert-butyl)piperidin-4-yl)-1H-1,2,3-triazol-4-yl)(4-chlorophenyl)methyl)-$N^4$-(3-chloro-4-fluorophenyl)quinazoline-4,6-diamine | 1 | 619.2 |

TABLE 1B-continued

| Cmpd | Structure | Name | Example Procedure | ES/MS m/z (M + H+) |
|---|---|---|---|---|
| II-6 | 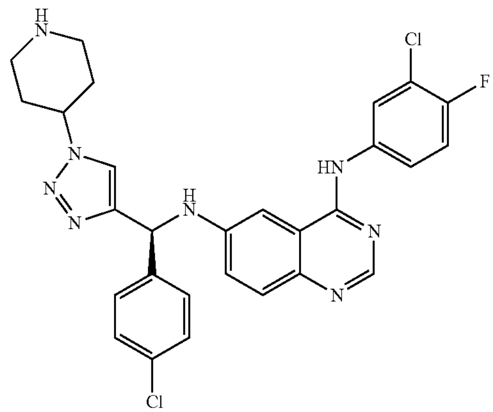 [SMILES: Fc1ccc(Nc2ncnc3ccc(N[C@@H](c4ccc(Cl)cc4)c4cn(C5CCNCC5)nn4)cc23)cc1Cl] | (S)-N4-(3-chloro-4-fluorophenyl)-N6-((4-chlorophenyl)(1-(piperidin-4-yl)-1H-1,2,3-triazol-4-yl)methyl)quinazoline-4,6-diamine | 2 | 563.14 |
| II-7 | 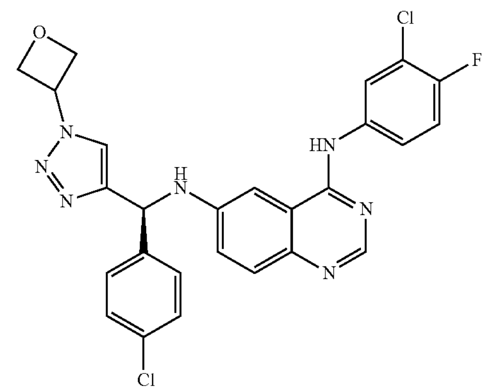 [SMILES: Fc1ccc(Nc2ncnc3ccc(N[C@@H](c4ccc(Cl)cc4)c4cn(C5COC5)nn4)cc23)cc1Cl] | (S)-N4-(3-chloro-4-fluorophenyl)-N6-((4-chlorophenyl)(1-(oxetan-3-yl)-1H-1,2,3-triazol-4-yl)methyl)quinazoline-4,6-diamine | 1 | 536.11 |
| II-8 | 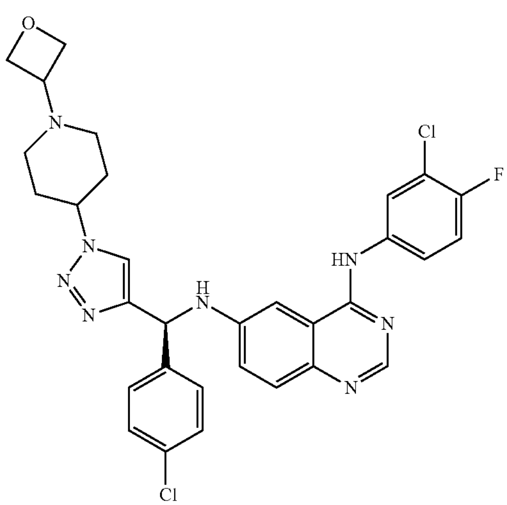 [SMILES: Fc1ccc(Nc2ncnc3ccc(N[C@@H](c4ccc(Cl)cc4)c4cn(C5CCN(C6COC6)CC5)nn4)cc23)cc1Cl] | (S)-N4-(3-chloro-4-fluorophenyl)-N6-((4-chlorophenyl)(1-(1-(oxetan-3-yl)piperidin-4-yl)-1H-1,2,3-triazol-4-yl)methyl)quinazoline-4,6-diamine | 3 | 619.16 |

TABLE 1B-continued

| Cmpd | Structure | Name | Example Procedure | ES/MS m/z (M + H+) |
|---|---|---|---|---|
| II-9 | 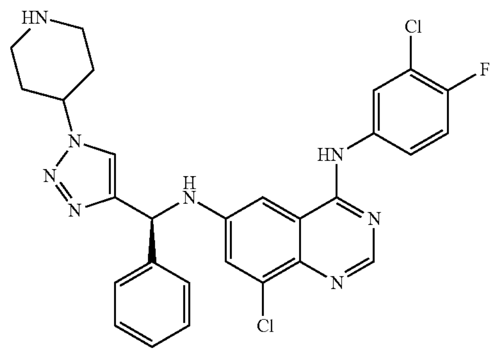 [SMILES: Fc1ccc(Nc2ncnc3c(Cl)cc(N[C@@H](c4ccccc4)c4cn(C5CCNCC5)nn4)cc23)cc1Cl] | (S)-8-chloro-N4-(3-chloro-4-fluorophenyl)-N6-(phenyl(1-(piperidin-4-yl)-1H-1,2,3-triazol-4-yl)methyl)quinazoline-4,6-diamine | 7 | |
| II-10 | 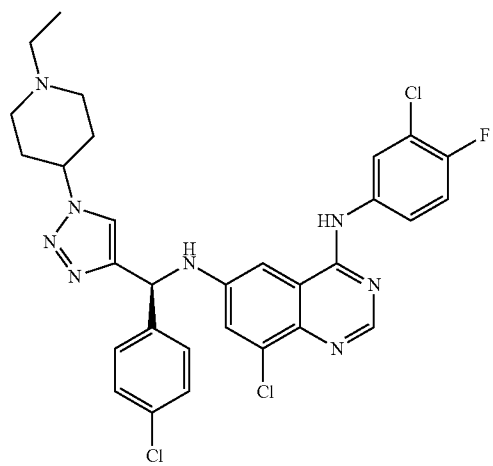 [SMILES: CCN1CCC(n2cc([C@@H](Nc3cc(Cl)c4ncnc(Nc5ccc(F)c(Cl)c5)c4c3)c3ccc(Cl)cc3)nn2)CC1] | (S)-8-chloro-N$^4$-(3-chloro-4-fluorophenyl)-N$^6$-((4-chlorophenyl)(1-(1-ethylpiperidin-4-yl)-1H-1,2,3-triazol-4-yl)methyl)quinazoline-4,6-diamine | 3 | 625.5 |
| II-11 | 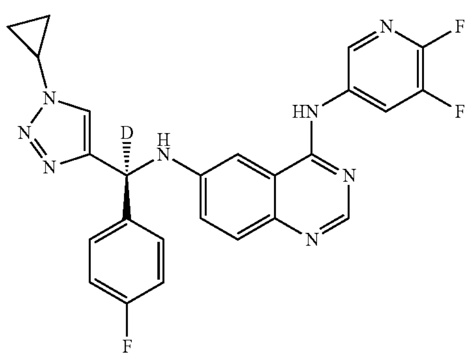 | (S)-N$^6$-((1-cyclopropyl-1H-1,2,3-triazol-4-yl)(4-fluorophenyl)methyl-d)-N$^4$-(5,6-difluoropyridin-3-yl)quinazoline-4,6-diamine | 1 | 490.19 |
| III-1 | 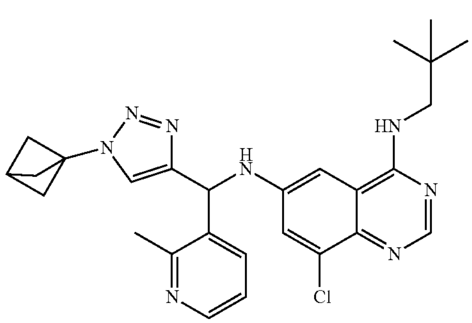 [SMILES: Cc1ncccc1C(Nc1cc(Cl)c2ncnc(NCC(C)(C)C)c2c1)c1cn(C23CC(C2)C3)nn1] | N$^6$-((1-(bicyclo[1.1.1]pentan-1-yl)-1H-1,2,3-triazol-4-yl)(2-methylpyridin-3-yl)methyl)-8-chloro-N4-neopentylquinazoline-4,6-diamine | 11 | 503.62 |

TABLE 1B-continued

| Cmpd | Structure | Name | Example Procedure | ES/MS m/z (M + H+) |
|---|---|---|---|---|
| III-2 | 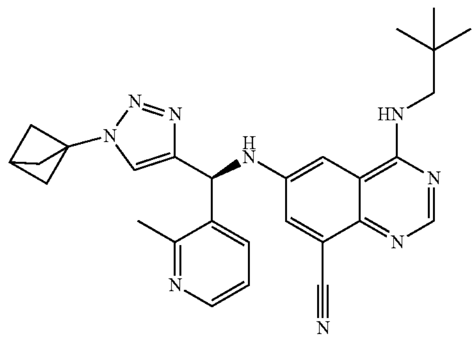 [SMILES: Cc1ncccc1[C@H](Nc1cc(C#N)c2ncnc(NCC(C)(C)C)c2c1)c1cn(C23CC(C2)C3)nn1] | (S)-6-(((1-(bicyclo[1.1.1]pentan-1-yl)-1H-1,2,3-triazol-4-yl)(2-methylpyridin-3-yl)methyl)amino)-4-(neopentylamino)quinazoline-8-carbonitrile | 11 | 494.54 |
| III-3 | 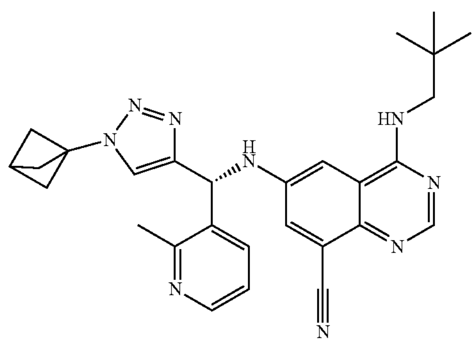 [SMILES: Cc1ncccc1[C@@H](Nc1cc(C#N)c2ncnc(NCC(C)(C)C)c2c1)c1cn(C23CC(C2)C3)nn1] | (R)-6-(((1-(bicyclo[1.1.1]pentan-1-yl)-1H-1,2,3-triazol-4-yl)(2-methylpyridin-3-yl)methyl)amino)-4-(neopentylamino)quinazoline-8-carbonitrile | 11 | 494.61 |
| III-4 | 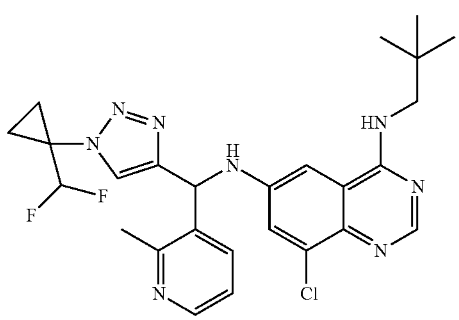 [SMILES: Cc1ncccc1C(Nc1cc(Cl)c2ncnc(NCC(C)(C)C)c2c1)c1cn(C2(C(F)F)CC2)nn1] | 8-chloro-N6-((1-(1-(difluoromethyl)cyclopropyl)-1H-1,2,3-triazol-4-yl)(2-methylpyridin-3-yl)methyl)-N4-neopentylquinazoline-4,6-diamine | 12 | 527.56 |
| III-5 | 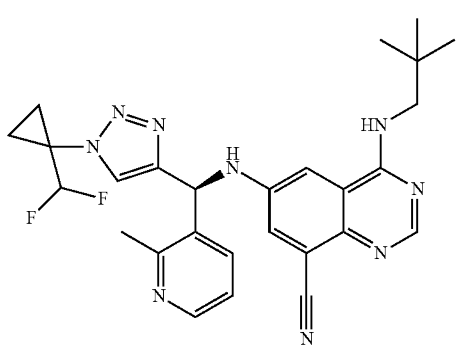 [SMILES: Cc1ncccc1[C@H](Nc1cc(C#N)c2ncnc(NCC(C)(C)C)c2c1)c1cn(C2(C(F)F)CC2)nn1] | (S)-6-(((1-(1-(difluoromethyl)cyclopropyl)-1H-1,2,3-triazol-4-yl)(2-methylpyridin-3-yl)methyl)amino)-4-(neopentylamino)quinazoline-8-carbonitrile | 12 | 518.52 |

TABLE 1B-continued

| Cmpd | Structure | Name | Example Procedure | ES/MS m/z (M + H+) |
|------|-----------|------|-------------------|---------------------|
| III-6 | 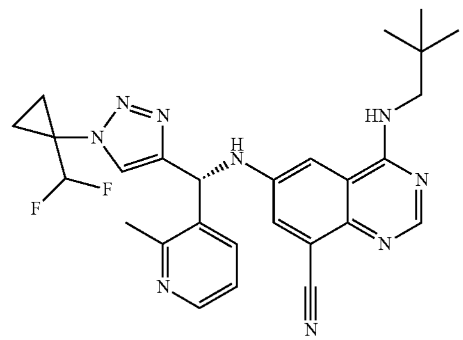 [SMILES: Cc1ncccc1[C@@H](Nc1cc(C#N)c2ncnc(NCC(C)(C)C)c2c1)c1cn(C2(C(F)F)CC2)nn1] | (R)-6-(((1-(1-(difluoromethyl)cyclopropyl)-1H-1,2,3-triazol-4-yl)(2-methylpyridin-3-yl)methyl)amino)-4-(neopentylamino)quinazoline-8-carbonitrile | 12 | 518.45 |

Proton NMR data for select compounds is shown below in Table 2.

TABLE 2

| Cmpd | $^1$H-NMR |
|------|-----------|
| I-1 | $^1$H NMR (400 MHz, DMSO-d$_6$) δ 9.39-9.32 (m, 1H), 8.64 (s, 1H), 8.06 (s, 1H), 7.64-7.51 (m, 5H), 7.36 (d, J = 2.1 Hz, 1H), 7.22-7.08 (m, 2H), 4.00-3.92 (m, 1H), 3.81 (dd, J = 12.9, 7.2 Hz, 1H), 3.41 (dd, J = 12.9, 5.5 Hz, 1H), 1.19-1.05 (m, 4H), 0.93 (s, 9H). |
| I-2 | $^1$H NMR (400 MHz, DMSO-d$_6$) δ 9.35 (t, J = 6.4 Hz, 1H), 8.65 (s, 1H), 8.06 (s, 1H), 7.64-7.50 (m, 5H), 7.35 (d, J = 2.2 Hz, 1H), 7.21-7.09 (m, 2H), 6.04 (d, J = 7.7 Hz, 1H), 4.01-3.91 (m, 1H), 3.81 (dd, J = 12.9, 7.1 Hz, 1H), 3.41 (dd, J = 12.9, 5.5 Hz, 1H), 1.19-1.04 (m, 4H), 0.93 (s, 9H). |
| I-3 | $^1$H NMR (400 MHz, DMSO-d$_6$) δ 9.34 (t, J = 6.5 Hz, 1H), 8.66 (s, 1H), 8.07 (s, 1H), 7.64-7.52 (m, 5H), 7.44-7.28 (m, 3H), 7.16 (dtd, J = 8.8, 6.5, 6.1, 2.2 Hz, 2H), 4.00-3.89 (m, 1H), 3.74-3.65 (m, 2H), 3.59-3.45 (m, 3H), 1.50 (tt, J = 9.5, 4.7 Hz, 2H), 1.24 (dd, J = 14.8, 10.8 Hz, 2H), 1.18-1.07 (m, 4H), 1.01 (s, 3H). |
| I-4 | $^1$H NMR (400 MHz, DMSO-d$_6$) δ 9.52 (d, J = 8.2 Hz, 1H), 8.65 (s, 1H), 8.08 (s, 1H), 7.65-7.55 (m, 5H), 7.50 (d, J = 1.9 Hz, 1H), 7.47-7.34 (m, 5H), 7.33-7.25 (m, 1H), 7.22-7.13 (m, 2H), 5.54 (td, J = 8.6, 6.3 Hz, 1H), 3.97 (td, J = 7.2, 3.6 Hz, 1H), 2.05 (ddt, J = 18.0, 14.0, 6.9 Hz, 2H), 1.20-1.06 (m, 4H), 0.97 (t, J = 7.3 Hz, 3H). |
| I-5 | $^1$H NMR (400 MHz, DMSO-d$_6$) δ 9.80 (dd, J = 23.4, 8.2 Hz, 1H), 8.74 (d, J = 3.9 Hz, 1H), 8.08 (d, J = 3.0 Hz, 1H), 7.68 (d, J = 5.8 Hz, 1H), 7.66-7.55 (m, 4H), 7.53-7.47 (m, 3H), 7.46-7.33 (m, 3H), 7.17 (td, J = 8.9, 6.4 Hz, 2H), 6.05 (dtd, J = 17.9, 8.9, 5.8 Hz, 1H), 4.03-3.91 (m, 1H), 3.47-3.26 (m, 2H), 1.20-1.03 (m, 4H). |
| I-6 | $^1$H NMR (400 MHz, DMSO-d$_6$) δ 8.10 (s, 1H), 7.75 (t, J = 6.3 Hz, 1H), 7.44 (s, 3H), 7.38-7.31 (m, 2H), 7.16 (t, J = 8.9 Hz, 2H), 4.01-3.94 (m, 1H), 3.54-3.39 (m, 4H), 1.18-1.05 (m, 4H), 0.91 (s, 9H), 0.83 (t, J = 6.9 Hz, 3H). |
| I-7 | $^1$H NMR (400 MHz, DMSO-d$_6$) δ 9.32 (t, J = 6.3 Hz, 1H), 8.65 (s, 1H), 8.15 (s, 1H), 8.00 (t, J = 1.7 Hz, 1H), 7.89-7.84 (m, 1H), 7.74 (dt, J = 7.7, 1.4 Hz, 1H), 7.70 (s, 1H), 7.62-7.52 (m, 3H), 7.32 (d, J = 2.2 Hz, 1H), 4.01-3.87 (m, 2H), 3.32 (dd, J = 12.9, 5.2 Hz, 1H), 1.19-1.05 (m, 4H), 0.93 (s, 9H). |
| I-8 | $^1$H NMR (400 MHz, DMSO-d$_6$) δ 9.41 (t, J = 6.4 Hz, 1H), 8.64 (s, 1H), 8.04 (s, 1H), 7.59 (d, J = 9.1 Hz, 1H), 7.55-7.44 (m, 4H), 7.37-7.29 (m, 3H), 6.33 (d, J = 7.9 Hz, 1H), 4.01-3.91 (m, 1H), 3.65 (dd, J = 12.9, 6.5 Hz, 1H), 3.52 (dd, J = 12.9, 6.0 Hz, 1H), 1.17-1.03 (m, 4H), 0.92 (s, 9H). |
| I-9 | $^1$H NMR (400 MHz, DMSO-d$_6$) δ 9.39 (s, 1H), 8.51 (s, 1H), 8.07 (s, 1H), 7.63 (d, J = 2.2 Hz, 1H), 7.53 (s, 1H), 7.51-7.45 (m, 2H), 7.38-7.29 (m, 3H), 3.96 (td, J = 7.3, 3.7 Hz, 1H), 3.64 (dd, J = 13.0, 6.6 Hz, 1H), 3.51 (dd, J = 12.9, 6.0 Hz, 1H), 1.19-1.04 (m, 4H), 0.92 (s, 9H). |
| I-10 | $^1$H NMR (400 MHz, DMSO-d$_6$) δ 9.39 (s, 1H), 8.51 (s, 1H), 7.99 (s, 1H), 7.66 (d, J = 2.3 Hz, 1H), 7.61 (s, 1H), 7.52-7.45 (m, 2H), 7.42-7.29 (m, 3H), 5.26 (s, 2H), 3.72 (dd, J = 13.0, 6.9 Hz, 1H), 3.43 (dd, J = 12.9, 5.6 Hz, 1H), 0.93 (s, 9H). |
| I-11 | $^1$H NMR (400 MHz, DMSO-d$_6$) δ 9.30 (s, 1H), 8.50 (d, J = 6.9 Hz, 1H), 8.08-8.03 (m, 1H), 7.66 (d, J = 2.2 Hz, 1H), 7.62-7.54 (m, 3H), 7.49-7.27 (m, 7H), 7.23-7.13 (m, 3H), 5.70 (d, J = 7.2 Hz, 1H), 3.96 (ddt, J = 12.6, 8.4, 3.7 Hz, 1H), 3.23 (d, J = 0.8 Hz, 1H), 2.70-2.57 (m, 2H), 2.43-2.25 (m, 2H), 1.21-1.01 (m, 4H). |
| I-12 | 1H NMR (400 MHz, DMSO-d6) δ 8.48 (d, J = 6.1 Hz, 1H), 8.37 (t, J = 1.3 Hz, 1H), 7.66 (d, J = 2.3 Hz, 1H), 7.59 (ddd, J = 8.2, 5.4, 1.5 Hz, 3H), 7.49-7.27 (m, 7H), 7.20 (tdd, J = 8.9, 3.2, 2.1 Hz, 2H), 5.74-5.57 (m, 1H), 2.71-2.54 (m, 2H), 2.32 (dq, J = 13.4, 7.6 Hz, 2H), 1.83-1.65 (m, 4H). |
| I-13 | 1H NMR (400 MHz, DMSO-d6) δ 9.19 (s, 1H) 8.49 (d, J = 1.8 Hz, 1H), 8.37 (s, 1H), 7.67 (d, J = 2.3 Hz, 1H), 7.63 (s, 2H), 7.61-7.55 (m, 2H), 7.36 (d, J = 2.3 Hz, 1H), 7.22-7.15 (m, 2H), 3.71 (dd, J = 12.9, 6.8 Hz, 1H), 3.46 (dd, J = 13.0, 5.8 Hz, 1H), 1.81-1.62 (m, 4H), 0.93 (s, 9H). |
| I-14 | 1H NMR (400 MHz, DMSO-d6) δ 8.30 (d, J = 1.9 Hz, 1H), 8.05 (d, J = 1.9 Hz, 1H), 7.79 (t, J = 2.2 Hz, 1H), 7.59-7.53 (m, 2H), 7.50 (d, J = 2.7 Hz, 1H), 7.34 (s, 2H), 7.19-7.12 (m, 2H), 3.94 (d, J = 16.8 Hz, 1H), 3.66 (d, J = 6.7 Hz, 1H), 3.29 (s, 1H), 1.17-1.05 (m, 4H), 0.91 (d, J = 1.9 Hz, 9H). |
| I-15 | 1H NMR (400 MHz, DMSO-d6) δ 8.45 (s, 1H), 8.06 (d, J = 1.9 Hz, 1H), 7.82 (d, J = 2.3 Hz, 1H), 7.56 (ddd, J = 9.3, 5.4, 2.0 Hz, 3H), 7.34 (d, J = 2.3 Hz, 1H), 7.16 (td, J = 8.9, 2.0 Hz, 2H), 3.96 (td, J = 5.5, 4.8, 2.6 Hz, 1H), 3.82-3.74 (m, 1H), 3.40 (d, J = 25.3 Hz, 1H), 1.18-1.05 (m, 4H), 0.92 (d, J = 1.9 Hz, 9H). |
| I-16 | 1H NMR (400 MHz, DMSO-d6) δ 9.30 (s, 1H), 8.51 (s, 1H), 8.15 (s, 1H), 7.67 (d, J = 2.3 Hz, 2H), 7.62-7.54 (m, 2H), 7.35 (d, J = 2.4 Hz, 1H), 7.17 (t, J = 8.8 Hz, 2H), 4.68 (d, J = 48.5 Hz, 2H), 3.76 (m, 1H), 3.46-3.38 (m, 1H), 1.41 (m, 2H), 1.35 (d, J = 5.5 Hz, 2H), 0.93 (s, 9H). |
| I-19 | 1H NMR (400 MHz, DMSO-d6) δ 8.35 (d, J = 3.7 Hz, 1H), 8.10-8.04 (m, 1H), 7.80 (q, J = 2.5 Hz, 1H), 7.48 (t, J = 4.3 Hz, 4H), 7.34 (q, J = 4.4 Hz, 2H), 3.97 (m, 1H), 3.54 (m, 1H), 3.39 ms, 1H), 1.17-1.06 (m, 4H), 0.95-0.88 (m, 9H). |
| I-20 | 1H NMR (400 MHz, DMSO-d6) δ 8.46-8.42 (m, 1H), 8.34 (d, J = 6.8 Hz, 1H), 7.79 (d, J = 7.3 Hz, 1H), 7.54-7.44 (m, 3H), 7.37 (d, J = 5.8 Hz, 3H), 3.60-3.35 (m, 2H), 1.99 (d, J = 51.7 Hz, 4H), 0.91 (dd, J = 6.0, 2.5 Hz, 9H). |
| I-21 | 1H NMR (400 MHz, DMSO-d6) δ 9.23 (s, 1H), 8.51 (s, 1H), 8.22 (s, 1H), 7.85 (t, J = 7.5 Hz, 1H), 7.73-7.55 (m, 2H), 7.24 (d, J = 2.8 Hz, 1H), 7.08-6.96 (m, 1H), 6.30-5.94 (m, 2H), 3.69 (dd, J = 12.9, 6.7 Hz, 1H), 3.53-3.40 (m, 1H), 2.61-2.43 (s, 3H), 1.51 (s, 4H), 0.90 (d, J = 3.2 Hz, 9H). |
| I-22 | 1H NMR (400 MHz, DMSO-d6) δ 8.33 (d, J = 2.0 Hz, 1H), 8.20 (d, J = 2.0 Hz, 1H), 7.83 (d, J = 17.0 Hz, 2H), 7.38 (d, J = 13.9 Hz, 2H), 6.98 (s, 1H), 6.27-5.93 (m, 2H), 3.32 (s, 2H), 2.50 (s, 3H), 1.50 (s, 4H), 0.87 (t, J = 3.7 Hz, 9H). |

TABLE 2-continued

| Cmpd | ¹H-NMR |
|---|---|
| I-23 | ¹H NMR (400 MHz, Methanol-d₄) δ 8.47 (s, 1H), 8.00 (s, 1H), 7.67 (dd, J = 7.7, 1.3 Hz, 1H), 7.62-7.54 (m, 2H), 7.35 (t, J = 7.8 Hz, 1H), 6.99 (d, J = 2.3 Hz, 1H), 6.25 (s, 1H), 5.93 (t, J = 54.7 Hz, 1H), 3.74 (d, J = 13.0 Hz, 1H), 3.61 (d, J = 13.0 Hz, 1H), 2.59 (s, 3H), 1.53 (d, J = 1.4 Hz, 4H), 0.95 (s, 9H). |
| I-24 | ¹H NMR (400 MHz, Methanol-d₄) δ 8.44 (s, 1H), 8.34 (d, J = 8.1 Hz, 1H), 7.96 (s, 1H), 7.84 (d, J = 2.5 Hz, 1H), 7.71 (dd, J = 7.5, 1.2 Hz, 1H), 7.49 (t, J = 7.8 Hz, 1H), 7.41 (d, J = 7.7 Hz, 1H), 7.32 (d, J = 2.5 Hz, 1H), 6.83 (d, J = 7.6 Hz, 1H), 6.56 (s, 1H), 5.91 (t, J = 54.7 Hz, 1H), 3.67 (d, J = 13.1 Hz, 1H), 3.60 (s, 3H), 3.53 (d, J = 13.1 Hz, 1H), 1.50 (d, J = 3.6 Hz, 4H), 0.88 (s, 9H). |
| I-25 | ¹H NMR (400 MHz, Methanol-d₄) δ 8.45 (s, 1H), 8.35 (d, J = 8.1 Hz, 1H), 7.94 (s, 1H), 7.76-7.65 (m, 1H), 7.60 (d, J = 2.3 Hz, 1H), 7.49 (t, J = 7.8 Hz, 1H), 7.41 (d, J = 7.7 Hz, 1H), 7.05 (d, J = 2.3 Hz, 1H), 6.83 (d, J = 7.7 Hz, 1H), 6.54 (s, 1H), 5.91 (t, J = 54.7 Hz, 1H), 3.71 (d, J = 13.0 Hz, 1H), 3.63-3.51 (m, 4H), 1.50 (d, J = 3.7 Hz, 4H), 0.89 (s, 9H). |
| I-26 | ¹H NMR (400 MHz, Methanol-d₄) δ 8.47 (s, 1H), 7.92 (s, 1H), 7.78 (t, J = 8.1 Hz, 1H), 7.59 (d, J = 2.3 Hz, 1H), 7.04 (d, J = 2.3 Hz, 1H), 6.88 (dd, J = 8.4, 2.8 Hz, 1H), 6.17 (s, 1H), 3.68 (s, 2H), 2.67 (d, J = 17.2 Hz, 1H), 2.52 (s, 3H), 2.37 (s, 6H), 0.96 (s, 9H). |
| I-27 | ¹H NMR (400 MHz, Methanol-d₄) δ 8.31 (d, J = 8.1 Hz, 1H), 8.21 (s, 1H), 7.80 (s, 1H), 7.73 (dd, J = 7.5, 1.3 Hz, 1H), 7.54-7.33 (m, 3H), 6.91 (d, J = 7.6 Hz, 1H), 6.74 (d, J = 2.4 Hz, 1H), 6.49 (s, 1H), 3.59 (s, 3H), 3.47 (d, J = 13.3 Hz, 1H), 2.66 (s, 1H), 2.35 (s, 6H), 2.01 (d, J = 8.8 Hz, 1H), 1.33-1.14 (m, 2H), 0.81 (s, 9H). |
| II-1 | ¹H NMR (400 MHz, DMSO-d₆) δ 9.84 (s, 1H), 8.45 (s, 1H), 8.04 (m, 2H), 7.69 (m, 2H), 7.52-7.22 (m, 13H), 6.14 (s, 1H), 5.07 (s, 2H), 4.71 (m, 1H), 4.08 (m, 2H), 2.95 (m, 2H), 2.04 (m, 2H), 1.86 (m, 2H). |
| II-2 | ¹H NMR (400 MHz, DMSO-d₆) δ 9.73 (s, 1H), 8.72 (m, 1H), 8.44 (m, 2H), 8.04 (m, 2H), 7.69 (m, 2H), 7.52-7.22 (m, 9H), 6.17 (m, 1H), 4.77 (m, 1H), 3.39 (m, 2H), 3.06 (m, 2H), 2.24 (m, 2H), 2.10 (m, 2H). |
| II-3 | ¹H NMR (400 MHz, DMSO-d₆) δ 9.67 (s, 1H), 9.38 (s, 1H), 8.43 (s, 1H), 8.05 (m, 2H), 7.69 (m, 2H), 7.52-7.22 (m, 9H), 6.17 (m, 1H), 4.74 (m, 1H), 3.61 (m, 2H), 3.10 (m, 4H), 2.34 (m, 2H), 2.18 (m, 2H), 1.22 (m, 3H). |
| II-4 | ¹H NMR (400 MHz, DMSO-d₆) δ 9.67 (s, 1H), 9.38 (s, 1H), 8.43 (s, 1H), 8.05 (m, 2H), 7.69 (m, 2H), 7.52-7.22 (m, 9H), 6.17 (m, 1H), 4.74 (m, 1H), 3.61 (m, 2H), 3.10 (m, 4H), 2.34 (m, 2H), 2.18 (m, 2H), 1.22 (m, 3H). |
| II-5 | ¹H NMR (400 MHz, DMSO-d₆) δ 10.56 (s, 1H), 9.24 (s, 1H), 8.67 (s, 1H), 8.10-7.97 (m, 2H), 7.71-7.60 (m, 3H), 7.59-7.51 (m, 3H), 7.47-7.42 (m, 2H), 6.18 (d, J = 8.8 Hz, 1H), 4.89-4.75 (m, 1H), 3.67 (d, J = 12.2 Hz, 2H), 3.13 (q, J = 11.2 Hz, 2H), 2.45-2.19 (m, 4H), 1.36 (s, 9H). |
| II-6 | ¹H NMR (400 MHz, DMSO-d₆) δ 8.71 (s, 1H), 8.48 (s, 1H), 8.06 (s, 1H), 8.00 (dd, J = 6.8, 2.6 Hz, 1H), 7.74-7.61 (m, 3H), 7.59-7.50 (m, 5H), 7.47-7.40 (m, 2H), 6.16 (d, J = 8.7 Hz, 1H), 4.86-4.73 (m, 1H), 3.42 (d, J = 13.4 Hz, 2H), 3.10 (t, J = 11.6 Hz, 2H), 2.27 (d, J = 13.2 Hz, 2H), 2.12 (d, J = 12.5 Hz, 2H). |
| II-7 | ¹H NMR (400 MHz, DMSO-d₆) δ 10.76 (s, 1H), 9.17 (s, 0H), 8.73 (s, 1H), 8.33-8.26 (m, 1H), 8.23 (s, 1H), 7.99 (dd, J = 6.8, 2.6 Hz, 1H), 7.76 (d, J = 8.9 Hz, 1H), 7.72-7.62 (m, 3H), 7.59-7.51 (m, 3H), 7.48-7.41 (m, 2H), 6.18 (d, J = 8.7 Hz, 1H), 5.83 (tt, J = 7.6, 6.1 Hz, 1H), 5.08-4.95 (m, 3H), 4.89 (dddd, J = 9.0, 6.9, 6.1, 0.6 Hz, 2H). |
| II-8 | ¹H NMR (400 MHz, DMSO-d₆) δ 9.35 (s, 1H), 8.37 (s, 1H), 8.14 (dd, J = 6.9, 2.6 Hz, 1H), 8.09 (s, 1H), 7.77 (ddd, J = 9.1, 4.3, 2.6 Hz, 1H), 7.59-7.54 (m, 4H), 7.48-7.38 (m, 5H), 7.33 (d, J = 2.4 Hz, 1H), 7.20 (d, J = 8.9 Hz, 1H), 6.17 (d, J = 8.8 Hz, 1H), 4.54 (t, J = 6.5 Hz, 3H), 4.42 (t, J = 6.1 Hz, 2H), 1.99 (dd, J = 24.0, 11.8 Hz, 8H). |
| II-9 | ¹H NMR (400 MHz, DMSO-d₆) δ 9.73 (s, 1H), 8.72 (m, 1H), 8.44 (m, 2H), 8.04 (m, 2H), 7.69 (m, 2H), 7.52-7.22 (m, 9H), 6.17 (m, 1H), 4.77 (m, 1H), 3.39 (m, 2H), 3.06 (m, 2H), 2.24 (m, 2H), 2.10 (m, 2H) |
| II-10 | ¹H NMR (400 MHz, DMSO-d₆) δ 9.69 (s, 1H), 9.34 (d, J = 11.9 Hz, 1H), 8.45 (s, 1H), 8.15-7.96 (m, 2H), 7.78-7.62 (m, 2H), 7.60-7.31 (m, 8H), 6.17 (d, J = 8.2 Hz, 1H), 4.91-4.65 (m, 1H), 3.62 (m, 2H), 3.28-2.95 (m, 4H), 2.43-2.28 (m, 2H), 2.28-2.06 (m, 2H), 1.33-1.10 (m, 3H). |
| II-11 | ¹H NMR (400 MHz, DMSO-d₆) δ 11.10 (s, 1H), 8.78 (s, 1H), 8.47 (ddd, J = 10.9, 8.7, 2.3 Hz, 1H), 8.35 (t, J = 2.1 Hz, 1H), 8.06 (s, 1H), 7.80-7.66 (m, 3H), 7.61-7.52 (m, 3H), 7.24-7.15 (m, 2H), 4.03-3.92 (m, 1H), 1.20-1.03 (m, 4H). |
| III-2 | ¹H NMR (400 MHz, Methanol-d4) δ 8.51 (d, J = 5.2 Hz, 1H), 8.34 (s, 1H), 8.06 (d, J = 7.9 Hz, 1H), 8.01 (s, 1H), 7.74 (d, J = 2.5 Hz, 1H), 7.53 (dd, J = 7.9, 5.2 Hz, 1H), 7.27 (d, J = 2.5 Hz, 1H), 6.28 (s, 1H), 3.55 (s, 2H), 2.69 (s, 1H), 2.69 (s, 3H), 2.38 (s, 6H), 0.94 (s, 9H). |
| III-3 | ¹H NMR (400 MHz, Methanol-d4) δ 8.48 (s, 1H), 8.33 (s, 1H), 8.04-7.95 (m, 2H), 7.73 (d, J = 2.5 Hz, 1H), 7.49 (dd, J = 7.9, 5.2 Hz, 1H), 7.25 (s, 1H), 6.27 (s, 1H), 3.54 (d, J = 1.4 Hz, 2H), 2.69 (s, 1H), 2.68 (s, 3H), 2.38 (s, 6H), 0.93 (s, 9H). |
| III-5 | ¹H NMR (400 MHz, Methanol-d4) δ 8.58 (dd, J = 5.4, 1.5 Hz, 1H), 8.40 (s, 1H), 8.23 (dd, J = 7.9, 1.5 Hz, 1H), 8.20 (s, 1H), 7.80 (d, J = 2.5 Hz, 1H), 7.67 (dd, J = 8.0, 5.5 Hz, 1H), 7.39 (d, J = 2.5 Hz, 1H), 6.35 (s, 1H), 5.94 (t, J = 54.6 Hz, 1H), 3.67-3.53 (m, 2H), 2.72 (s, 3H), 1.54 (s, 4H), 0.95 (s, 9H). |
| III-6 | ¹H NMR (400 MHz, Methanol-d4) δ 8.58-8.53 (m, 1H), 8.38 (s, 1H), 8.18 (s, 1H), 7.78 (d, J = 2.6 Hz, 1H), 7.62 (dd, J = 8.0, 5.5 Hz, 1H), 7.35 (d, J = 2.5 Hz, 1H), 6.33 (s, 1H), 5.94 (t, J = 54.6 Hz, 1H), 3.58 (d, J = 3.6 Hz, 2H), 2.71 (s, 3H), 1.54 (s, 4H), 0.95 (s, 9H). |

Biological Assays

The following examples, from Examples 23 to 25, describe biological assays for measuring certain test compounds' activity against TNFα, Cot (also known as Tpl2), and EGFR. As summarized in Table 3, the test compounds are effective inhibitors of Cot.

Example 23: Cot Monocyte TNFα Cell Based Assay

Cryopreserved human monocytes (Stem Cell Technologies) were thawed, diluted in RPMI with Glutamax (10 mM HEPES, 1× Pen-Strep, 55 µM β-mercaptoethanol, 1 mM Sodium pyruvate) media containing 10% FBS to 0.125× 10^6 cells/ml and recovered at 37° C. for 2 hours. The cell suspension was then plated at a density of 5,000 cells/well onto black 384 well Greiner clear bottom plates. Plates were pre-spotted with test compounds and serially diluted in DMSO where 200 nL/well were delivered using the Echo 550 acoustic liquid dispenser (Labcyte®) for a final DMSO concentration of 0.5%. Plated cells were treated with compound for 1 hour at 37° C. Cells were then stimulated with 50 pg/ml of LPS (Sigma) excluding outside columns of plate used for unstimulated cell control wells. Cells were incubated for an additional 4 hours at 37° C. Cells were then spun out of the media and 5 ul of sample were taken and analyzed for total TNFα content using the TR-FRET Human TNFα detection system (CisBio). This system utilizes two labeled antibodies (cryptate and XL665) that bind to two different epitopes of the TNFα molecule and produce FRET signal proportional to the concentration of TNFα in the sample. Detection antibodies are mixed 50:50 and 5 µL were dispensed into each well. Plates were covered with clear seals and incubated at room temp overnight. The following morning plates were read using an Envision 2103 Multilabeled reader (PerkinElmer) with excitation/emission/FRET emission at 340 nm/615 nm/665 nm, respectively. Fluorescence intensities at 615 nm and 665 nm emission wavelengths were expressed as a ratio (665 nm/615 nm). Percent of control was calculated as follows:

$$\% \text{ Control} = 100 \times (\text{Ratio}_{Sample} - \text{Ratio}_{0\% \ stimulation}) / (\text{Ratio}_{100\% \ Stimulation} - \text{Ratio}_{0\% \ Stimulation})$$

where unstimulated cells (0% stimulation) were the negative control and stimulated cells (100% stimulation) were used as the positive control.

Example 24: High Throughput Cot Biochemical Assay

Human Cot enzyme activity was measured using KinEASE (Cisbio), a time-resolved fluorescence resonance energy transfer (TR-FRET) immunoassay. In this assay, Cot-catalyzes the phosporylation of a XL665-labeled peptide substrate. Europium conjugated phospho-tyrosine specific antibody binds the resulting phosphorylated peptide. Formation of phosphorylated peptide is quantified by TR-FRET with Europium as the donor and XL665 the acceptor in a 2-step endpoint assay. Purified recombinant human Cot catalytic domain (30-397 amino acids) was purchased from Carna Biosciences. In brief, test compounds serially diluted in DMSO were delivered into Proxy white, low volume, 384 well plates using the Echo 550 acoustic liquid dispenser (Labcyte®). Cot enzyme and substrates were dispensed into assay plates using a Multi-Flo (Bio-Tek Instruments). The standard 5 µL reaction mixture contained 400 µM ATP, 1 µM STK3 peptide, 5 nM of Cot in reaction buffer (10 mM MOPS, pH 7.0, 0.02% $NaN_3$, 0.5 mg/mL BSA, 10 mM MgOAc, 1 mM DTT, 0.025% NP-40, 1.5% glycerol) and 0.1% DMSO. After 2.5 hrs of incubation at room temperature, 5 µL of Stop and Detect Solution (1:200 Europium Cryptate labeled anti-phosphorylated peptide antibody solution and 125 nM strepavidin-XL665 Tracer in a 50 mM Hepes pH 7.0 detection buffer containing sufficient EDTA) was added. The plate was then further incubated for 120 minutes at room temperature and read using an Envision 2103 Multilabeled reader (PerkinElmer) with excitation/emission/FRET emission at 340 nm/615 nm/665 nm, respectively. Fluorescence intensities at 615 nm and 665 nm emission wavelengths were expressed as a ratio (665 nm/615 nm). Percent inhibition was calculated as follows:

$$\% \text{ Inhibition} = 100 \times (\text{Ratio}_{Sample} - \text{Ratio}_{0\% \ Inhibition}) / (\text{Ratio}_{100\% \ Inhibition} - \text{Ratio}_{0\% \ Inhibition})$$

where 0.1% DMSO (0% inhibition) was the negative control and 100 µM Comparative Example 1 (100% inhibition) was used as the positive control.

Example 25: High Throughput EGFR Biochemical Assay

EGFR activity was measured using KinEASE (Cisbio), a time-resolved fluorescence resonance energy transfer (TR-FRET) immunoassay. In this assay, EGFR-catalyzes the phosphorylation of a universal Tyrosine kinase peptide substrate labeled with XL665. Europium conjugated phosphortyrosine specific antibody binds the resulting phosphorylated peptide. Formation of phosphorylated peptide is quantified by TR-FRET with Europium as the donor and XL665 the acceptor. The assay was performed in two main steps. The first step is the kinase reaction step and the second step is the detection step with TR-FRET reagents. In brief, test compounds 1:3 serially diluted in DMSO were delivered into Corning white, low volume, non-binding 384 well plates using the Echo 550 acoustic liquid dispenser (Labcyte®). EGFR enzyme (Human EGFR, cytoplasmic domain [669-1210] from Carna Biosciences Cat. No. 08-115) and substrates TK substrate-biotin (included in Cisbio HTRF KinEASE-TK kit Cat. No. 62TK0PEJ) were dispensed into assay plates using a Multi-Flo (Bio-Tek Instruments). The standard 10 µL reaction mixture contained 6 µM ATP (1×Km) or 12 µM ATP (2×Km), 1 µM biotinylated peptide, 0.3 nM EGFR (for 1×Km ATP) or 0.1 nM EGFR (for 2×Km ATP) in reaction buffer (10 mM MOPS, pH 7.0, 1.5% Glycerol, 0.5 mg/ml BSA, 10 mM Mg-Acetate, 1 mM DTT, 0.025% NP-40). After 60 min of incubation at room temperature, 10 µL of Stop and Detect Solution (1:400 Europium Cryptate labeled anti-phosphorylated peptide antibody solution and 125 nM strepavidin-XL665 Tracer in a 50 mM Hepes pH 7.0 detection buffer containing sufficient EDTA) was added. The plate was then further incubated for over 60 minutes at room temperature and read using an Envision 2103 Multilabeled reader (PerkinElmer) with excitation/emission/FRET emission at 340 nm/615 nm/665 nm, respectively. Fluorescence intensities at 615 nm and 665 nm emission wavelengths were expressed as a ratio (665 nm/615 nm). Percent inhibition was calculated as follows:

$$\% \text{ Inhibition} = 100 \times (\text{Ratio}_{Sample} - \text{Ratio}_{0\% \ Inhibition}) / (\text{Ratio}_{100\% \ Inhibition} - \text{Ratio}_{0\% \ Inhibition})$$

where 0.05% DMSO (0% inhibition) was the negative control and 100 µM Staurosporine and Gefitinib (100% inhibition) was used as the positive control.

As shown in Table 3, the compounds provided herein are inhibitors of Cot (cancer Osaka thyroid).

TABLE 3

| Cmpd | $IC_{50}$ (nM) | $EC_{50}$ (nM) |
| --- | --- | --- |
| I-1 | 5 | 101 |
| I-2 | 7.7 | 85 |
| I-3 | 11 | 296 |
| I-4 | 43 | 796 |
| I-5 | 53 | 2503 |
| I-6 | 276 | 4231 |
| I-7 | 2.6 | 102 |
| I-8 | 13 | 169 |
| I-9 | 4.8 | 86 |
| I-10 | 13 | >1000 |
| I-11 | 46 | 671 |
| I-12 | 137 | >1000 |
| I-13 | 10 | 181 |
| I-14 | 2.1 | 42 |
| I-15 | 2.6 | 82 |
| I-16 | 3.1 | 46 |
| I-17 | 3.3 | 59 |
| I-18 | 8 | 195 |
| I-19 | 2.4 | 20 |
| I-20 | 3.3 | 35 |
| I-21 | 1.9 | 28 |
| I-22 | 1.7 | 36 |
| I-23 | 1.6 | |
| I-24 | 1.2 | 11.3 |
| I-25 | 2.4 | 25.5 |
| I-27 | 1.7 | 12.1 |
| II-1 | 8480 | |
| II-2 | 28 | |
| II-3 | 19 | |
| II-4 | 5.9 | 254 |
| II-5 | 72 | |
| II-6 | 49 | |
| II-7 | 284 | |
| II-8 | 318 | 1238 |
| II-9 | 8.3 | 337 |
| II-10 | 17 | 527 |
| II-11 | 74 | 645 |

The invention claimed is:

1. A method for inhibiting cancer Osaka thyroid (Cot) comprising administering, to a human patient in need thereof, an effective amount of a compound of Formula I:

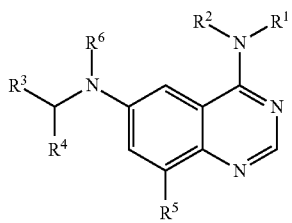

wherein
$R^1$ is $C_{1-9}$ alkyl, $C_{3-15}$ cycloalkyl, heterocyclyl, heteroaryl, or $C_{6-10}$ aryl;
wherein each $C_{1-9}$ alkyl, $C_{3-15}$ cycloalkyl, heterocyclyl, heteroaryl, and $C_{6-10}$ aryl may be optionally substituted with one to four $Z^1$;
$R^2$ is hydrogen, —C(O)—$R^7$, —C(O)O—$R^7$, —C(O)N$(R^7)_2$, or $C_{1-9}$ alkyl;
$R^3$ is heterocyclyl or heteroaryl;
wherein each heterocyclyl or heteroaryl is optionally substituted with one to four $Z^3$;
$R^4$ is aryl, heterocyclyl, or heteroaryl;
wherein each aryl, heterocyclyl, or heteroaryl is optionally substituted with one to four $Z^4$;
$R^5$ is hydrogen, halo, cyano, —$NO_2$, —O—$R^7$, —N($R^8$)($R^9$), —S(O)—$R^7$, —S(O)$_2R^7$, —S(O)$_2$N($R^7)_2$, —C(O)$R^7$, —OC(O)—$R^7$, —C(O)O—$R^7$, —OC(O)O—$R^7$, —OC(O)N($R^{10}$)($R^{11}$), —C(O)N($R^7)_2$, —N($R^7$)C(O)($R^7$), $C_{1-9}$ alkyl, $C_{2-6}$ alkenyl, $C_{2-6}$ alkynyl, $C_{1-9}$ alkylthio, $C_{1-6}$ haloalkyl, $C_{3-15}$ cycloalkyl, aryl, heterocyclyl, or heteroaryl;
wherein each $C_{1-9}$ alkyl, $C_{2-6}$ alkenyl, $C_{2-6}$ alkynyl, $C_{1-9}$ alkylthio, $C_{1-6}$ haloalkyl, $C_{3-15}$ cycloalkyl, aryl, heterocyclyl, and heteroaryl may be optionally substituted with one to four $Z^5$;
$R^6$ is hydrogen, —C(O)—$R^7$, —C(O)O—$R^7$, —C(O)N$(R^7)_2$, $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl;
wherein each $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, and heteroaryl may be optionally substituted with one to four $Z^6$;
each $R^7$ is independently hydrogen, $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl;
wherein each $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, and heteroaryl may be optionally substituted with one to four $Z^7$;
$R^8$ and $R^9$ at each occurrence are independently hydrogen, —S(O)$_2R^{10}$, —C(O)—$R^{10}$, —C(O)O—$R^{10}$, —C(O)N$(R^{10})(R^{11})$, $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl;
wherein each $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl may be optionally substituted with one to four $Z^8$;
$R^{10}$ and $R^{11}$ at each occurrence are independently hydrogen, $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl, wherein each $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, and heteroaryl optionally is substituted with one to four $Z^{1b}$;
each $Z^1$, $Z^3$, $Z^4$, $Z^5$, $Z^6$, $Z^7$ and $Z^8$ is independently hydrogen, oxo, halo, —$NO_2$, —$N_3$, cyano, thioxo, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O—$R^{12}$, —C(O)—$R^{12}$, —C(O)O—$R^{12}$, —C(O)—N($R^{13}$)($R^{14}$), —N($R^{13}$)($R^{14}$), —N($R^{13})_2(R^{14})^+$, —N($R^{12}$)C(O)—$R^{12}$, —N($R^{12}$)C(O)O—$R^{12}$, —N($R^{12}$)C(O)N($R^{13}$)($R^{14}$), —N($R^{12}$)S(O)$_2$($R^{12}$), —NR$^{12}$S(O)$_2$N($R^{13}$)($R^{14}$), —NR$^{12}$S(O)$_2$O($R^{12}$), —OC(O)$R^{12}$, —OC(O)—N($R^{13}$)($R^{14}$), —P(O)(O$R^{12})_2$, —OP(O)(O$R^{12})_2$, —CH$_2$P(O)(O$R^{12})_2$, —OCH$_2$P(O)(O$R^{12})_2$, —C(O)OCH$_2$P(O)(O$R^{12})_2$, —P(O)($R^{12}$)(O$R^{12}$), —OP(O)($R^{12}$)(O$R^{12}$), —CH$_2$P(O)($R^{12}$)(O$R^{12}$), —OCH$_2$P(O)($R^{12}$)(O$R^{12}$), —C(O)OCH$_2$P(O)($R^{12}$)(O$R^{12}$), —P(O)(N($R^{12})_2)_2$, —OP(O)(N($R^{12})_2)_2$, —CH$_2$P(O)(N($R^{12})_2)_2$, —OCH$_2$P(O)(N($R^{12})_2)_2$, —C(O)OCH$_2$P(O)(N($R^{12})_2)_2$, —P(O)(N($R^{12})_2)(O$R^{12}$), —OP(O)(N($R^{12})_2)(O$R^{12}$), —CH$_2$P(O)(N($R^{12})_2)(O$R^{12}$), —OCH$_2$P(O)(N($R^{12})_2)(O$R^{12}$), —C(O)OCH$_2$P(O)(N($R^{12})_2)(O$R^{12}$), —P(O)($R^{12}$)(N($R^{12})_2$), —OP(O)($R^{12}$)(N($R^{12})_2$), —CH$_2$P(O)($R^{12}$)(N($R^{12})_2$), —OCH$_2$P(O)($R^1$)($R^2$)(N($R^{12})_2$), —C(O)OCH$_2$P(O)($R^{12}$)(N($R^{12})_2$), —Si($R^{12})_3$, —S—$R^{12}$, —S(O)$R^{12}$, —S(O)(NH)$R^{12}$, —S(O)$_2R^{12}$ or —S(O)$_2$N($R^{13}$)($R^{14}$);
wherein any alkyl, alkenyl, alkynyl, cycloalkyl, haloalkyl, aryl, heteroaryl or heterocyclyl is optionally substituted with one to four $Z^{1a}$ groups;
each $Z^{1a}$ is independently oxo, halo, thioxo, —$NO_2$, cyano, —$N_3$, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O—$R^{12}$, —C(O)$R^{12}$, —C(O)O—$R^{12}$, —C(O)N($R^{13}$)($R^{14}$), —N($R^{13}$)($R^{14}$), —N($R^{13})_2(R^{14})^+$, —N($R^{12}$)—C(O)$R^{12}$, —N($R^{12}$)C(O)O($R^{12}$), —N($R^{12}$)C(O)N($R^{13}$)($R^4$), —N($R^{12}$)S(O)$_2$($R^{12}$), —N($R^{12}$)S(O)$_2$—N($R^{13}$)($R^{14}$), —N($R^{12}$)S(O)$_2$O($R^{12}$), —OC(O)$R^{12}$, —OC(O)O$R^{12}$, —OC(O)—N($R^{13}$)($R^{14}$), —Si($R^{12})_3$, —S—$R^{12}$, —S(O)$R^{12}$, —S(O)(NH)$R^{12}$, S(O)$_2R^{12}$ or —S(O)$_2$N($R^{13}$)($R^{14}$);
wherein any alkenyl, alkynyl, cycloalkyl, aryl, heteroaryl or heterocyclyl is optionally substituted with one to four $Z^{1b}$ groups;
each $R^{12}$ is independently hydrogen, $C_{1-9}$ alkyl, $C_{2-6}$ alkenyl, $C_{2-6}$ alkynyl, $C_{3-15}$ cycloalkyl, aryl, heteroaryl or heterocyclyl,
wherein any alkyl, alkenyl, alkynyl, cycloalkyl, aryl, heteroaryl or heterocyclyl is optionally substituted with one to four $Z^{1b}$ groups;
$R^{13}$ and $R^{14}$ at each occurrence are each independently hydrogen, $C_{1-9}$ alkyl, $C_{2-6}$ alkenyl, $C_{2-6}$ alkynyl, $C_{3-15}$ cycloalkyl, aryl, heteroaryl or heterocyclyl;
wherein any alkyl, alkenyl, alkynyl, cycloalkyl, aryl, heteroaryl or heterocyclyl is optionally substituted with one to four $Z^{1b}$ groups, or $R^{13}$ and $R^{14}$ together with the nitrogen to which they are attached form a heterocyclyl, wherein said heterocyclyl is optionally substituted with one to four $Z^{1b}$ groups;
each $Z^{1b}$ is independently oxo, thioxo, hydroxy, halo, —$NO_2$, —$N_3$, cyano, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O($C_{1-9}$ alkyl), —O($C_{2-6}$ alkenyl), —O($C_{2-6}$ alkynyl), —O($C_{3-15}$ cycloalkyl), —O($C_{1-8}$ haloalkyl), —O(aryl), —O(heteroaryl), —O(heterocyclyl), —$NH_2$, —NH($C_{1-9}$ alkyl), —NH($C_{2-6}$ alkenyl), —NH($C_{2-6}$ alkynyl), —NH($C_{3-5}$ cycloalkyl), —NH($C_{1-8}$ haloalkyl), —NH(aryl), —NH(heterocyclyl), —NH(heterocyclyl), —N($C_{1-9}$ alkyl)$_2$, —N($C_{3-15}$ cycloalkyl)$_2$, —N($C_{2-6}$ alkenyl)$_2$, —N($C_{2-6}$ alkynyl)$_2$, —N($C_{3-15}$ cycloalkyl)$_2$, —N($C_{1-8}$ haloalkyl)$_2$, —N(aryl)$_2$, —N(heteroaryl)$_2$, —N(heterocyclyl)$_2$, —N($C_{1-9}$ alkyl)($C_{3-15}$ cycloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)($C_{1-8}$ haloalkyl), —N($C_{1-9}$ alkyl)(aryl), —N($C_{1-9}$ alkyl)(heteroaryl), —N($C_{1-9}$ alkyl)(heterocyclyl), —C(O)($C_{1-9}$ alkyl), —C(O)($C_{2-6}$ alkenyl), —C(O)($C_{2-6}$ alkynyl), —C(O)($C_{3-15}$ cycloalkyl), —C(O)($C_{1-8}$haloalkyl), —C(O)(aryl), —C(O)(heteroaryl), —C(O)(heterocyclyl), —C(O)O$C_{1-9}$ alkyl), —C(O)O($C_{2-6}$ alkenyl), —C(O)O($C_{2-6}$ alkynyl), —C(O)O($C_{3-15}$cycloalkyl), —C(O)O($C_{1-8}$ haloalkyl), —C(O)O(aryl), —C(O)O(heteroaryl), —C(O)O(heterocyclyl), —C(O)NH$_2$, —C(O)NH($C_{1-9}$ alkyl), —C(O)NH($C_{2-6}$ alkenyl), —C(O)NH($C_{2-6}$ alkynyl), —C(O)NH($C_{3-15}$ cycloalkyl), —C(O)NH($C_{1-8}$ haloalkyl), —C(O)NH(aryl), —C(O)NH(heteroaryl), —C(O)NH(heterocyclyl), —C(O)N($C_{1-9}$ alkyl)$_2$, —C(O)N($C_{3-15}$ cycloalkyl)$_2$, —C(O)N($C_{2-6}$ alkenyl)$_2$, —C(O)N($C_{2-6}$ alkynyl)$_2$, —C(O)N($C_{3-15}$ cycloalkyl)$_2$, —C(O)N($C_{1-8}$ haloalkyl)$_2$, —C(O)N(aryl)$_2$, —C(O)N(heteroaryl)$_2$, —C(O)N(heterocyclyl)$_2$, —NHC(O)($C_{1-9}$ alkyl), —NHC(O)($C_{2-6}$ alkenyl), —NHC(O)($C_{2-6}$ alkynyl), —NHC(O)($C_{3-15}$ cycloalkyl), —NHC(O)($C_{1-8}$ haloalkyl), —NHC(O)(aryl), —NHC(O)(heteroaryl), —NHC(O)(heterocyclyl), —NHC(O)O($C_{1-9}$ alkyl), —NHC(O)O($C_{2-6}$ alkenyl), —NHC(O)O($C_{2-6}$ alkynyl), —NHC(O)O($C_{3-15}$ cycloalkyl), —NHC(O)O($C_{1-8}$ haloalkyl), —NHC(O)O(aryl), —NHC(O)O(heteroaryl), —NHC(O)O(heterocyclyl), —NHC(O)NH($C_{1-9}$ alkyl), —NHC(O)NH($C_{2-6}$ alkenyl), —NHC(O)NH($C_{2-6}$ alkynyl), —NHC(O)NH($C_{3-15}$ cycloalkyl), —NHC(O)NH($C_{1-8}$ haloalkyl), —NHC(O)NH(aryl), —NHC(O)NH(heteroaryl), —NHC(O)NH(heterocyclyl), —SH, —S($C_{1-9}$ alkyl), —S($C_{2-6}$ alkenyl), —S($C_{2-6}$ alkynyl), —S($C_{3-15}$ cycloalkyl), —S($C_{1-8}$ haloalkyl), —S(aryl), —S(heteroaryl), —S(heterocyclyl), —NHS(O)($C_{1-9}$ alkyl), —N($C_{1-9}$ alkyl)(S(O)($C_{1-9}$ alkyl), —S(O)N($C_{1-9}$ alkyl)$_2$, —S(O)($C_{1-9}$ alkyl), —S(O)(NH)($C_{1-9}$ alkyl), —S(O)($C_{2-6}$ alkenyl), —S(O)($C_{2-6}$ alkynyl), —S(O)($C_{3-15}$ cycloalkyl), —S(O)($C_{1-8}$ haloalkyl), —S(O)(aryl), —S(O)(heteroaryl), —S(O)(heterocyclyl), —S(O)$_2$($C_{1-9}$ alkyl), —S(O)$_2$($C_{2-6}$ alkenyl), —S(O)$_2$($C_{2-6}$ alkynyl), —S(O)$_2$($C_{3-15}$ cycloalkyl), —S(O)$_2$($C_{1-8}$ haloalkyl), —S(O)$_2$(aryl), —S(O)$_2$(heteroaryl), —S(O)$_2$(heterocyclyl), —S(O)$_2$NH($C_{1-9}$ alkyl), or —S(O)$_2$N($C_{1-9}$ alkyl)$_2$;

wherein any alkyl, cycloalkyl, aryl, heteroaryl, or heterocyclyl is optionally substituted with one to four halo, $C_{1-9}$ alkyl, $C_{1-8}$ haloalkyl, —OH, —NH$_2$, —NH($C_{1-9}$ alkyl), —NH($C_{3-15}$ cycloalkyl), —NH($C_{1-8}$ haloalkyl), —NH(aryl), —NH(heteroaryl), —NH(heterocyclyl), —N($C_{1-9}$ alkyl)$_2$, —N($C_{3-15}$ cycloalkyl)$_2$, —NHC(O)($C_{3-15}$ cycloalkyl), —NHC(O)($C_{1-8}$ haloalkyl), —NHC(O)(aryl), —NHC(O)(heteroaryl), —NHC(O)(heterocyclyl), —NHC(O)O($C_{1-9}$ alkyl), —NHC(O)O($C_{2-6}$ alkynyl), —NHC(O)O($C_{3-15}$ cycloalkyl), —NHC(O)O($C_{1-8}$ haloalkyl), —NHC(O)O(aryl), —NHC(O)O(heteroaryl), —NHC(O)O(heterocyclyl), —NHC(O)NH($C_{1-9}$ alkyl), —S(O)(NH)($C_{1-9}$ alkyl), S(O)$_2$($C_{1-9}$ alkyl), —S(O)$_2$($C_{3-15}$ cycloalkyl), —S(O)$_2$($C_{1-8}$ haloalkyl), —S(O)$_2$(aryl), —S(O)$_2$(heteroaryl), —S(O)$_2$(heterocyclyl), —S(O)$_2$NH($C_{1-9}$ alkyl), —S(O)$_2$N($C_{1-9}$ alkyl)$_2$, —O($C_{3-15}$ cycloalkyl), —O($C_{1-8}$ haloalkyl), —O(aryl), —O(heteroaryl), —O(heterocyclyl), or —O($C_{1-9}$ alkyl);

m is 0, 1, or 2;

or a pharmaceutically acceptable salt, stereoisomer, mixture of stereoisomers, or deuterated analog thereof.

2. The method of claim 1, wherein:

$R^1$ is $C_{1-9}$ alkyl or $C_{3-15}$ cycloalkyl;
  wherein each $C_{1-9}$ alkyl and $C_{3-15}$ cycloalkyl may be optionally substituted with one to four $Z^1$;

$R^2$ is hydrogen, —C(O)—$R^7$, —C(O)O—$R^7$, —C(O)N($R^7$)$_2$, or $C_{1-9}$ alkyl;

$R^3$ is heterocyclyl or heteroaryl;
  wherein each heterocyclyl or heteroaryl is optionally substituted with one to four $Z^3$;

$R^4$ is aryl, heterocyclyl, or heteroaryl;
  wherein each aryl, heterocyclyl, or heteroaryl is optionally substituted with one to four $Z^4$;

$R^5$ is hydrogen, halo, cyano, —NO$_2$, —O—$R^7$, —N($R^8$)($R^9$), —S(O)—$R^7$, —S(O)$_2R^7$, —S(O)$_2$N($R^7$)$_2$, —C(O)$R^7$, —OC(O)—$R^7$, —C(O)O—$R^7$, —OC(O)O—$R^7$, —OC(O)N($R^{10}$)($R^{11}$), —C(O)N($R^7$)$_2$, —N($R^7$)C(O)($R^7$), $C_{1-9}$ alkyl, $C_{2-6}$ alkenyl, $C_{2-6}$ alkynyl, $C_{1-9}$ alkylthio, $C_{1-6}$ haloalkyl, $C_{3-15}$ cycloalkyl, aryl, heterocyclyl, or heteroaryl;
  wherein each $C_{1-9}$ alkyl, $C_{2-6}$ alkenyl, $C_{2-6}$ alkynyl, $C_{1-9}$ alkylthio, $C_{1-6}$ haloalkyl, $C_{3-15}$ cycloalkyl, aryl, heterocyclyl, and heteroaryl may be optionally substituted with one to four $Z^5$;

$R^6$ is hydrogen, —C(O)—$R^7$, —C(O)O—$R^7$, —C(O)N($R^7$)$_2$, $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl;
  wherein each $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, and heteroaryl may be optionally substituted with one to four $Z^6$;

each $R^7$ is independently hydrogen, $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl;
  wherein each $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, and heteroaryl may be optionally substituted with one to four $Z^7$;

$R^8$ and $R^9$ at each occurrence are independently hydrogen, —S(O)$_2R^{10}$, —C(O)—$R^{10}$, —C(O)O—$R^{10}$, —C(O)N($R^{10}$)($R^{11}$), $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl;
  wherein each $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl may be optionally substituted with one to four $Z^8$;

$R^{10}$ and $R^{11}$ at each occurrence are independently hydrogen, $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl,
  wherein each $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, and heteroaryl optionally is substituted with one to four $Z^{1b}$;

each $Z^1$, $Z^3$, $Z^4$, $Z^5$, $Z^6$, $Z^7$ and $Z^8$ is independently hydrogen, oxo, halo, —NO$_2$, —N$_3$, cyano, thioxo, $C_{1-9}$ alkyl, $C_{2-6}$ alkenyl, $C_{2-6}$ alkynyl, $C_{3-15}$ cycloalkyl, $C_{1-8}$ haloalkyl, aryl, heterocyclyl, heterocyclyl, —O—$R^{12}$, —C(O)—$R^{12}$, —C(O)O—$R^{12}$, —C(O)—N($R^{13}$)($R^{14}$), —N(R$^{13}$)(R$^{14}$), —N(R$^{13}$)$_2$(R$^{14}$)$^+$, —N(R$^{12}$)C(O)—R$^{12}$, —N(R$^{12}$)C(O)O—R$^{12}$, —N(R$^{12}$)C(O)N(R$^{13}$)(R$^{14}$), —N(R$^{12}$)S(O)$_2$(R$^{12}$), —NR$^{12}$S(O)$_2$N(R$^{13}$)(R$^{14}$), —NR$^{12}$S(O)$_2$O(R$^{12}$), —OC(O)R$^{12}$, —OC(O)—N(R$^{13}$)(R$^{14}$), —P(O)(OR$^{12}$)$_2$, —OP(O)(OR$^{12}$)$_2$, —CH$_2$P(O)(OR$^{12}$)$_2$, —OCH$_2$P(O)(OR$^{12}$)$_2$, —C(O)OCH$_2$P(O)(OR$^{12}$)$_2$, —P(O)(R$^{12}$)(OR$^{12}$), —OP(O)(R$^{12}$)(OR$^{12}$), —CH$_2$P(O)(R$^{12}$)(OR$^{12}$), —OCH$_2$P(O)(R$^{12}$)(OR$^{12}$), —C(O)OCH$_2$P(O)(R$^{12}$)(OR$^{12}$), —P(O)(N(R$^{12}$)$_2$)$_2$, —OP(O)(N(R$^{12}$)$_2$)$_2$, —CH$_2$P(O)(N(R$^{12}$)$_2$)$_2$, —OCH$_2$P(O)(N(R$^{12}$)$_2$)$_2$, —C(O)OCH$_2$P(O)(N(R$^{12}$)$_2$)$_2$, —P(O)(N(R$^{12}$)$_2$)(OR$^{12}$), —OP(O)(N(R$^{12}$)$_2$)(OR$^{12}$), —CH$_2$P(O)(N(R$^{12}$)$_2$)(OR$^{12}$), —OCH$_2$P(O)(N(R$^{12}$)$_2$)(OR$^{12}$), —C(O)OCH$_2$P(O)(N(R$^{12}$)$_2$)(OR$^{12}$), —P(O)(R$^{12}$)(N(R$^{12}$)$_2$), —OP(O)(R$^{12}$)(N(R$^{12}$)$_2$), —CH$_2$P(O(R$^3$)(R$^{12}$)(N(R$^{12}$)$_2$), —OCH$_2$P(O)(R$^{12}$)(N(R$^{12}$)$_2$), —C(O)OCH$_2$P(O)(R$^{12}$)(N(R$^{12}$)$_2$), —Si(R$^{12}$)$_3$, —S—R$^{12}$, —S(O)R$^{12}$, —S(O)(NH)R$^{12}$, —S(O)$_2$R$^{12}$ or —S(O)$_2$N(R$^{13}$)(R$^{14}$);

wherein any alkyl, alkenyl, alkynyl, cycloalkyl, haloalkyl, aryl, heteroaryl or heterocyclyl is optionally substituted with one to four Z$^{1a}$ groups;

each Z$^{1a}$ is independently oxo, halo, thioxo, —NO$_2$, cyano, —N$_3$, C$_{1-9}$ alkyl, C$_{2-6}$ alkenyl, C$_{2-6}$ alkynyl, C$_{3-15}$ cycloalkyl, C$_{1-8}$ haloalkyl, aryl, heteroaryl, heterocyclyl, —O—R$^{12}$, —C(O)R$^{12}$, —C(O)O—R$^{12}$, —C(O)N(R$^{13}$)(R$^{14}$), —N(R$^{13}$)(R$^{14}$), —N(R$^{13}$)$_2$(R$^{14}$)$^+$, —N(R$^{12}$)—C(O)R$^{12}$, —N(R$^{12}$)C(O)O(R$^{12}$), —N(R$^{12}$)C(O)N(R$^{13}$)(R$^4$), —N(R$^{12}$)S(O)$_2$(R$^{12}$), —N(R$^{12}$)S(O)$_2$—N(R$^{13}$)(R$^{14}$), —N(R$^{12}$)S(O)$_2$O(R$^{12}$), —OC(O)R$^{12}$, —OC(O)OR$^{12}$, —OC(O)—N(R$^{13}$)(R$^{14}$), —Si(R$^{12}$)$_3$, —S—R$^{12}$, —S(O)R$^{12}$, —S(O)(NH)R$^{12}$, —S(O)$_2$R$^{12}$ or —S(O)$_2$N(R$^{13}$)(R$^{14}$);

wherein any alkenyl, alkynyl, cycloalkyl, aryl, heteroaryl or heterocyclyl is optionally substituted with one to four Z$^{1b}$ groups;

each R$^{12}$ is independently hydrogen, C$_{1-9}$ alkyl, C$_{2-6}$ alkenyl, C$_{2-6}$ alkynyl, C$_{3-15}$ cycloalkyl, aryl, heteroaryl or heterocyclyl,
wherein any alkyl, alkenyl, alkynyl, cycloalkyl, aryl, heteroaryl or heterocyclyl is optionally substituted with one to four Z$^{1b}$ groups;

R$^{13}$ and R$^{14}$ at each occurrence are each independently hydrogen, C$_{1-9}$ alkyl, C$_{2-6}$ alkenyl, C$_{2-6}$ alkynyl, C$_{3-15}$ cycloalkyl, aryl, heteroaryl or heterocyclyl;
wherein any alkyl, alkenyl, alkynyl, cycloalkyl, aryl, heteroaryl or heterocyclyl is optionally substituted with one to four Z$^{1b}$ groups, or R$^{13}$ and R$^{14}$ together with the nitrogen to which they are attached form a heterocyclyl, wherein said heterocyclyl is optionally substituted with one to four Z$^{1b}$ groups;

each Z$^{1b}$ is independently oxo, thioxo, hydroxy, halo, —NO$_2$, —N$_3$, cyano, C$_{1-9}$ alkyl, C$_{2-6}$ alkenyl, C$_{2-6}$ alkynyl, C$_{3-15}$ cycloalkyl, C$_{1-8}$ haloalkyl, aryl, heteroaryl, heterocyclyl, —O(C$_{1-9}$ alkyl), —O(C$_{2-6}$ alkenyl), —O(C$_{2-6}$ alkynyl), —O(C$_{3-15}$ cycloalkyl), —O(C$_{1-8}$ haloalkyl), —O(aryl), —O(heteroaryl), —O(heterocyclyl), —NH$_2$, —NH(C$_{1-9}$ alkyl), —NH(C$_{2-6}$ alkenyl), —NH(C$_{2-6}$ alkynyl), —NH(C$_{3-5}$ cycloalkyl), —NH(C$_{1-8}$ haloalkyl), —NH(aryl), —NH(heteroaryl), —NH(heterocyclyl), —N(C$_{1-9}$ alkyl)$_2$, —N(C$_{3-15}$ cycloalkyl)$_2$, —N(C$_{2-6}$ alkenyl)$_2$, —N(C$_{2-6}$ alkynyl)$_2$, —N(C$_{3-15}$ cycloalkyl)$_2$, —N(C$_{1-8}$ haloalkyl)$_2$, —N(aryl)$_2$, —N(heteroaryl)$_2$, —N(heterocyclyl)$_2$, —N(C$_{1-9}$ alkyl)(C$_{3-15}$ cycloalkyl), —N(C$_{1-9}$ alkyl)(C$_{2-6}$ alkenyl), —N(C$_{1-9}$ alkyl)(C$_{2-6}$ alkynyl), —N(C$_{1-9}$ alkyl)(C$_{3-15}$ cycloalkyl), —N(C$_{1-9}$ alkyl)(C$_{1-8}$ haloalkyl), —N(C$_{1-9}$ alkyl)(aryl), —N(C$_{1-9}$ alkyl)(heteroaryl), —N(C$_{1-9}$ alkyl)(heterocyclyl), —C(O)(C$_{1-9}$ alkyl), —C(O)(C$_{2-6}$ alkenyl), —C(O)(C$_{2-6}$ alkynyl), —C(O)(C$_{3-15}$ cycloalkyl), —C(O)(C$_{1-8}$haloalkyl), —C(O)(aryl), —C(O)(heteroaryl), —C(O)(heterocyclyl), —C(O)O(C$_{1-9}$ alkyl), —C(O)O(C$_{2-6}$ alkenyl), —C(O)O(C$_{2-6}$ alkynyl), —C(O)O(C$_{3-15}$cycloalkyl), —C(O)O(C$_{1-8}$ haloalkyl), —C(O)O(aryl), —C(O)O(heteroaryl), —C(O)O(heterocyclyl), —C(O)NH$_2$, —C(O)NH(C$_{1-9}$ alkyl), —C(O)NH(C$_{2-6}$ alkenyl), —C(O)NH(C$_{2-6}$ alkynyl), —C(O)NH(C$_{3-15}$ cycloalkyl), —C(O)NH(C$_{1-8}$ haloalkyl), —C(O)NH(aryl), —C(O)NH(heteroaryl), —C(O)NH(heterocyclyl), —C(O)N(C$_{1-9}$ alkyl)$_2$, —C(O)N(C$_{3-15}$ cycloalkyl)$_2$, —C(O)N(C$_{2-6}$ alkenyl)$_2$, —C(O)N(C$_{2-6}$ alkynyl)$_2$, —C(O)N(C$_{3-15}$ cycloalkyl)$_2$, —C(O)N(C$_{1-8}$ haloalkyl)$_2$, —C(O)N(aryl)$_2$, —C(O)N(heteroaryl)$_2$, —C(O)N(heterocyclyl)$_2$, —NHC(O)(C$_{1-9}$ alkyl), —NHC(O)(C$_{2-6}$ alkenyl), —NHC(O)(C$_{2-6}$ alkynyl), —NHC(O)(C$_{3-15}$ cycloalkyl), —NHC(O)(C$_{1-8}$ haloalkyl), —NHC(O)(aryl), —NHC(O)(heteroaryl), —NHC(O)(heterocyclyl), —NHC(O)O(C$_{1-9}$ alkyl), —NHC(O)O(C$_{2-6}$ alkenyl), —NHC(O)O(C$_{2-6}$ alkynyl), —NHC(O)O(C$_{3-15}$ cycloalkyl), —NHC(O)O(C$_{1-8}$ haloalkyl), —NHC(O)O(aryl), —NHC(O)O(heteroaryl), —NHC(O)O(heterocyclyl), —NHC(O)NH(C$_{1-9}$ alkyl), —NHC(O)NH(C$_{2-6}$ alkenyl), —NHC(O)NH(C$_{2-6}$ alkynyl), —NHC(O)NH(C$_{3-15}$ cycloalkyl), —NHC(O)NH(C$_{1-8}$ haloalkyl), —NHC(O)NH(aryl), —NHC(O)NH(heteroaryl), —NHC(O)NH(heterocyclyl), —SH, —S(C$_{1-9}$ alkyl), —S(C$_{2-6}$ alkenyl), —S(C$_{2-6}$ alkynyl), —S(C$_{3-15}$ cycloalkyl), —S(C$_{1-8}$ haloalkyl), —S(aryl), —S(heteroaryl), —S(heterocyclyl), —NHS(O)(C$_{1-9}$ alkyl), —N(C$_{1-9}$ alkyl)(S(O)(C$_{1-9}$ alkyl), —S(O)N(C$_{1-9}$ alkyl)$_2$, —S(O)(C$_{1-9}$ alkyl), —S(O)(NH)(C$_{1-9}$ alkyl), —S(O)(C$_{2-6}$ alkenyl), —S(O)(C$_{2-6}$ alkynyl), —S(O)(C$_{3-15}$ cycloalkyl), —S(O)(C$_{1-8}$ haloalkyl), —S(O)(aryl), —S(O)(heteroaryl), —S(O)(heterocyclyl), —S(O)$_2$(C$_{1-9}$ alkyl), —S(O)$_2$(C$_{2-6}$ alkenyl), —S(O)$_2$(C$_{2-6}$ alkynyl), —S(O)$_2$(C$_{3-15}$ cycloalkyl), —S(O)$_2$(C$_{1-8}$ haloalkyl), —S(O)$_2$(aryl), —S(O)$_2$(heteroaryl), —S(O)$_2$(heterocyclyl), —S(O)$_2$NH(C$_{1-9}$ alkyl), or —S(O)$_2$N(C$_{1-9}$ alkyl)$_2$;
wherein any alkyl, cycloalkyl, aryl, heteroaryl, or heterocyclyl is optionally substituted with one to four halo, C$_{1-9}$ alkyl, C$_{1-8}$ haloalkyl, —OH, —NH$_2$, —NH(C$_{1-9}$ alkyl), —NH(C$_{3-15}$ cycloalkyl), —NH(C$_{1-8}$ haloalkyl), —NH(aryl), —NH(heteroaryl), —NH(heterocyclyl), —N(C$_{1-9}$ alkyl)$_2$, —N(C$_{3-15}$ cycloalkyl)$_2$, —NHC(O)(C$_{3-15}$ cycloalkyl), —NHC(O)(C$_{1-8}$ haloalkyl), —NHC(O)(aryl), —NHC(O)(heteroaryl), —NHC(O)(heterocyclyl), —NHC(O)O(C$_{1-9}$ alkyl), —NHC(O)O(C$_{2-6}$ alkynyl), —NHC(O)O(C$_{3-15}$ cycloalkyl), —NHC(O)O(C$_{1-8}$ haloalkyl), —NHC(O)O(aryl), —NHC(O)O(heteroaryl), —NHC(O)O(heterocyclyl), —NHC(O)NH(C$_{1-9}$ alkyl), —S(O)(NH)(C$_{1-9}$ alkyl), S(O)$_2$(C$_{1-9}$ alkyl), —S(O)$_2$(C$_{3-15}$ cycloalkyl), —S(O)$_2$(C$_{1-8}$ haloalkyl), —S(O)$_2$(aryl), —S(O)$_2$(heteroaryl), —S(O)$_2$(heterocyclyl), —S(O)$_2$NH(C$_{1-9}$ alkyl), —S(O)$_2$N(C$_{1-9}$ alkyl)$_2$, —O(C$_{3-15}$ cycloalkyl), —O(C$_{1-8}$ haloalkyl), —O(aryl), —O(heteroaryl), —O(heterocyclyl), or —O(C$_{1-9}$ alkyl);

m is 0, 1, or 2;

or a pharmaceutically acceptable salt, stereoisomer, mixture of stereoisomers, or deuterated analog thereof.

3. The method of claim 1, wherein $R^2$ is hydrogen, or a pharmaceutically acceptable salt thereof.

4. The method of claim 1 comprising administering an effective amount of a compound of Formula II:

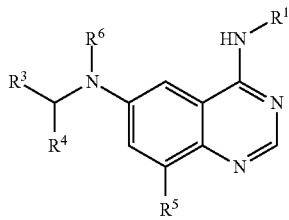

II wherein $R^1$, $R^3$, $R^4$, $R^5$ and $R^6$ are as defined in claim 1, or a pharmaceutically acceptable salt thereof.

5. The method of claim 1 comprising administering an effective amount of a compound of Formula IIA:

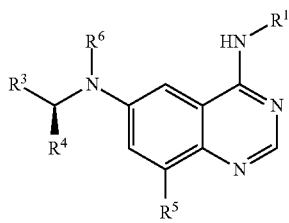

IIA wherein $R^1$, $R^3$, $R^4$, $R^5$ and $R^6$ are as defined in claim 1, or a pharmaceutically acceptable salt thereof.

6. The method of claim 1 comprising administering an effective amount of a Formula IIIA:

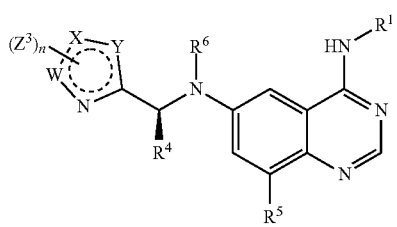

IIIA wherein $R^1$, $R^4$, $R^5$ and $R^6$ are as defined in claim 1,
W, X and Y are each independently N or C;
n is 1, 2, or 3;
each $Z^3$ is independently hydrogen, oxo, halo, —$NO_2$, —$N_3$, cyano, thioxo, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O—$R^{12}$, —C(O)—$R^{12}$, —C(O)O—$R^{12}$, —C(O)—N($R^{13}$)($R^{14}$), —N($R^{13}$)($R^{14}$), —N($R^{13}$)$_2$($R^{14}$)$^+$, —N($R^{12}$)C(O)—$R^{12}$, —N($R^{12}$)C(O)O—$R^{12}$, —N($R^{12}$)C(O)N($R^{13}$)($R^{14}$), —N($R^{12}$)S(O)$_2$($R^{12}$), —N$R^{12}$S(O)$_2$N($R^{13}$)($R^{14}$), —N$R^{12}$S(O)$_2$O($R^{12}$), —OC(O)$R^{12}$, —OC(O)—N($R^{13}$)($R^{14}$), —P(O)(O$R^{12}$)$_2$, —OP(O)(O$R^{12}$)$_2$, —CH$_2$P(O)(O$R^{12}$)$_2$, —OCH$_2$P(O)(O$R^{12}$)$_2$, —C(O)OCH$_2$P(O)(O$R^{12}$)$_2$, —P(O)($R^{12}$)(O$R^{12}$), —OP(O)($R^{12}$)(O$R^{12}$), —CH$_2$P(O)($R^{12}$)(O$R^{12}$), —OCH$_2$P(O)($R^{12}$)(O$R^{12}$), —C(O)OCH$_2$P(O)($R^{12}$)(O$R^{12}$), —P(O)(N($R^{12}$)$_2$)$_2$, —OP(O)(N($R^{12}$)$_2$)$_2$, —CH$_2$P(O)(N($R^{12}$)$_2$)$_2$, —OCH$_2$P(O)(N($R^{12}$)$_2$)$_2$, —C(O)OCH$_2$P(O)(N($R^{12}$)$_2$)$_2$, —P(O)(N($R^{12}$)$_2$)(O$R^{12}$), —OP(O)(N($R^{12}$)$_2$)($R^{12}$), —CH$_2$P(O)(N($R^{12}$)$_2$)(O$R^{12}$), —OCH$_2$P(O)(N($R^{12}$)$_2$)(O$R^{12}$), —C(O)OCH$_2$P(O)(N($R^{12}$)$_2$)(O$R^{12}$), —P(O)($R^{12}$)(N($R^{12}$)$_2$), —OP(O)($R^{12}$)(N($R^{12}$)$_2$), —CH$_2$P(O)($R^{12}$)(N($R^{12}$)$_2$), —(OCH$_2$P(O))($R^{12}$)(N($R^{12}$)$_2$), —C(O)OCH$_2$P(O)($R^{12}$)(N($R^{12}$)$_2$), —Si($R^{12}$)$_3$, —S—$R^{12}$, —S(O)$R^{12}$, —S(O)(NH)$R^{12}$, —S(O)$_2R^{12}$ or —S(O)$_2$N($R^{13}$)($R^{14}$);
wherein any alkyl, alkenyl, alkynyl, cycloalkyl, haloalkyl, aryl, heteroaryl or heterocyclyl is optionally substituted with one to four $Z^{1a}$ groups;
each $Z^{1a}$ is independently oxo, halo, thioxo, —$NO_2$, cyano, —$N_3$, $C_{1-9}$ alkyl, $C_{2-6}$ alkenyl, $C_{2-6}$ alkynyl, $C_{3-15}$ cycloalkyl, $C_{1-8}$ haloalkyl, $C_{1-8}$ hydroxyalkyl, aryl, heteroaryl, heterocyclyl, —O—$R^{12}$, —C(O)$R^{12}$, —C(O)O—$R^{12}$, —C(O)N($R^{13}$)($R^{14}$), —N($R^{13}$)($R^{14}$), —N($R^{13}$)$_2$($R^{14}$)$^+$, —N($R^{12}$)—C(O)$R^{12}$, —N($R^{12}$)C(O)O($R^{12}$), —N($R^{12}$)C(O)N($R^{13}$)($R^{14}$), —N($R^{12}$)S(O)$_2$($R^{12}$), —N($R^{12}$)S(O)$_2$—N($R^{13}$)($R^{14}$), —N($R^{12}$)S(O)$_2$O($R^{12}$), —OC(O)$R^{12}$, —OC(O)O$R^{12}$, —OC(O)—N($R^{13}$)($R^{14}$), —C(O)N($R^{12}$)—S(O)$_2R^{12}$, —Si($R^{12}$)$_3$, —S—$R^{12}$, —S(O)$R^{12}$, —S(O)(NH)$R^{12}$, —S(O)$_2R^{12}$ or —S(O)$_2$N($R^{13}$)($R^{14}$);
wherein any alkenyl, alkynyl, cycloalkyl, aryl, heteroaryl or heterocyclyl is optionally substituted with one to four $Z^{1b}$ groups;
each $R^{12}$ is independently hydrogen, $C_{1-9}$ alkyl, $C_{2-6}$ alkenyl, $C_{2-6}$ alkynyl, $C_{3-15}$ cycloalkyl, aryl, heteroaryl or heterocyclyl;
wherein any alkyl, alkenyl, alkynyl, cycloalkyl, aryl, heteroaryl or heterocyclyl is optionally substituted with one to four $Z^{1b}$ groups;
$R^{13}$ and $R^{14}$ at each occurrence are each independently hydrogen, $C_{1-9}$ alkyl, $C_{2-6}$ alkenyl, $C_{2-6}$ alkynyl, $C_{3-15}$ cycloalkyl, aryl, heteroaryl or heterocyclyl;
wherein any alkyl, alkenyl, alkynyl, cycloalkyl, aryl, heteroaryl or heterocyclyl is optionally substituted with one to four $Z^{1b}$ groups, or $R^{13}$ and $R^{14}$ together with the nitrogen to which they are attached form a heterocyclyl, wherein said heterocyclyl is optionally substituted with one to four $Z^{1b}$ groups; and
each $Z^{1b}$ is independently oxo, thioxo, hydroxy, halo, —$NO_2$, —$N_3$, cyano, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O($C_{1-9}$ alkyl), —O($C_{2-6}$ alkenyl), —O($C_{2-6}$ alkynyl), —O($C_{3-15}$ cycloalkyl), —O($C_{1-8}$ haloalkyl), —O(aryl), —O(heteroaryl), —O(heterocyclyl), —$NH_2$, —NH($C_{1-9}$ alkyl), —NH($C_{2-6}$ alkenyl), —NH($C_{2-6}$ alkynyl), —NH($C_{3-15}$ cycloalkyl), —NH($C_{1-8}$ haloalkyl), —NH(aryl), —NH(heteroaryl), —NH(heterocyclyl), —N($C_{1-9}$ alkyl)$_2$, —N($C_{3-15}$ cycloalkyl)$_2$, —N($C_{2-6}$ alkenyl)$_2$, —N($C_{2-6}$ alkynyl)$_2$, —N($C_{3-15}$ cycloalkyl)$_2$, —N($C_{1-8}$ haloalkyl)$_2$, —N(aryl)$_2$, —N(heteroaryl)$_2$, —N(heterocyclyl)$_2$, —N($C_{1-9}$ alkyl)($C_{3-15}$ cycloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)($C_{1-8}$ haloalkyl), —N($C_{1-9}$alkyl)(aryl), —N($C_{1-9}$ alkyl)(heteroaryl), —N($C_{1-9}$ alkyl)(heterocyclyl), —C(O)($C_{1-9}$ alkyl), —C(O)($C_{2-6}$ alkenyl), —C(O)($C_{2-6}$ alkynyl), —C(O)($C_{3-15}$ cycloalkyl), —C(O)($C_{1-8}$haloalkyl), —C(O)(aryl), —C(O)(heteroaryl), —C(O)(heterocyclyl), —C(O)O($C_{1-9}$ alkyl), —C(O)O($C_{2-6}$ alkenyl), —C(O)O($C_{2-6}$ alkynyl), —C(O)O($C_{3-15}$ cycloalkyl), —C(O)O($C_{1-8}$ haloalkyl), —C(O)O(aryl), —C(O)O(heteroaryl), —C(O)O(heterocyclyl), —C(O)

NH$_2$, —C(O)NH(C$_{1-9}$ alkyl), —C(O)NH(C$_{2-6}$ alkenyl), —C(O)NH(C$_{2-6}$ alkynyl), —C(O)NH(C$_{3-15}$ cycloalkyl), —C(O)NH(C$_{1-8}$ haloalkyl), —C(O)NH(aryl), —C(O)NH(heteroaryl), —C(O)NH(heterocyclyl), —C(O)N(C$_{1-9}$ alkyl)$_2$, —C(O)N(C$_{3-15}$ cycloalkyl)$_2$, —C(O)N(C$_{2-6}$ alkenyl)$_2$, —C(O)N(C$_{2-6}$ alkynyl)$_2$, —C(O)N(C$_{3-15}$ cycloalkyl)$_2$, —C(O)N(C$_{1-8}$ haloalkyl)$_2$, —C(O)N(aryl)$_2$, —C(O)N(heteroaryl)$_2$, —C(O)N(heterocyclyl)$_2$, —NHC(O)(C$_{1-9}$ alkyl), —NHC(O)(C$_{2-6}$ alkenyl), —NHC(O)(C$_{2-6}$ alkynyl), —NHC(O)(C$_{3-15}$ cycloalkyl), —NHC(O)(C$_{1-8}$ haloalkyl), —NHC(O)(aryl), —NHC(O)(heteroaryl), —NHC(O)(heterocyclyl), —NHC(O)O(C$_{1-9}$ alkyl), —NHC(O)O(C$_{2-6}$ alkenyl), —NHC(O)O(C$_{2-6}$ alkynyl), —NHC(O)O(C$_{3-15}$ cycloalkyl), —NHC(O)O(C$_{1-8}$ haloalkyl), —NHC(O)O(aryl), —NHC(O)O(heteroaryl), —NHC(O)O(heterocyclyl), —NHC(O)NH(C$_{1-9}$ alkyl), —NHC(O)NH(C$_{2-6}$ alkenyl), —NHC(O)NH(C$_{2-6}$ alkynyl), —NHC(O)NH(C$_{3-15}$ cycloalkyl), —NHC(O)NH(C$_{1-8}$ haloalkyl), —NHC(O)NH(aryl), —NHC(O)NH(heteroaryl), —NHC(O)NH(heterocyclyl), —SH, —S(C$_{1-9}$ alkyl), —S(C$_{2-6}$ alkenyl), —S(C$_{2-6}$ alkynyl), —S(C$_{3-15}$ cycloalkyl), —S(C$_{1-8}$ haloalkyl), —S(aryl), —S(heteroaryl), —S(heterocyclyl), —NHS(O)(C$_{1-9}$ alkyl), —N(C$_{1-9}$ alkyl)(S(O)(C$_{1-9}$ alkyl), —S(O)N(C$_{1-9}$ alkyl)$_2$, —S(O)(C$_{1-9}$ alkyl), —S(O)(NH)(C$_{1-9}$ alkyl), —S(O)(C$_{2-6}$ alkenyl), —S(O)(C$_{2-6}$ alkynyl), —S(O)(C$_{3-15}$ cycloalkyl), —S(O)(C$_{1-8}$ haloalkyl), —S(O)(aryl), —S(O)(heteroaryl), —S(O)(heterocyclyl), —S(O)$_2$(C$_{1-9}$ alkyl), —S(O)$_2$(C$_{2-6}$ alkenyl), —S(O)$_2$(C$_{2-6}$ alkynyl), —S(O)$_2$(C$_{3-15}$ cycloalkyl), —S(O)$_2$(C$_{1-8}$ haloalkyl), —S(O)$_2$(aryl), —S(O)$_2$(heteroaryl), —S(O)$_2$(heterocyclyl), —S(O)$_2$NH(C$_{1-9}$ alkyl), or —S(O)$_2$N(C$_{1-9}$ alkyl)$_2$;

wherein any alkyl, cycloalkyl, aryl, heteroaryl, or heterocyclyl is optionally substituted with one to four halo, C$_{1-9}$ alkyl, C$_{1-8}$ haloalkyl, —OH, —NH$_2$, —NH(C$_{1-9}$ alkyl), —NH(C$_{3-15}$ cycloalkyl), —NH(C$_{1-8}$ haloalkyl), —NH(aryl), —NH(heteroaryl), —NH(heterocyclyl), —N(C$_{1-9}$ alkyl)$_2$, —N(C$_{3-15}$ cycloalkyl)$_2$, —NHC(O)(C$_{3-15}$ cycloalkyl), —NHC(O)(C$_{1-8}$ haloalkyl), —NHC(O)(aryl), —NHC(O)(heteroaryl), —NHC(O)(heterocyclyl), —NHC(O)O(C$_{1-9}$ alkyl), —NHC(O)O(C$_{2-6}$ alkynyl), —NHC(O)O(C$_{3-15}$ cycloalkyl), —NHC(O)O(C$_{1-8}$ haloalkyl), —NHC(O)O(aryl), —NHC(O)O(heteroaryl), —NHC(O)O(heterocyclyl), —NHC(O)NH(C$_{1-9}$ alkyl), —S(O)(NH)(C$_{1-9}$ alkyl), S(O)$_2$(C$_{1-9}$ alkyl), —S(O)$_2$(C$_{3-15}$ cycloalkyl), —S(O)$_2$(C$_{1-8}$ haloalkyl), —S(O)$_2$(aryl), —S(O)$_2$(heteroaryl), —S(O)$_2$(heterocyclyl), —S(O)$_2$NH(C$_{1-9}$ alkyl), —S(O)$_2$N(C$_{1-9}$ alkyl)$_2$, —O(C$_{3-15}$ cycloalkyl), —O(C$_{1-8}$ haloalkyl), —O(aryl), —O(heteroaryl), —O(heterocyclyl), or —O(C$_{1-9}$ alkyl);

or a pharmaceutically acceptable salt, stereoisomer, mixture of stereoisomers, or deuterated analog thereof.

7. The method of claim 6, wherein W is N, X is N—Z$^3$, and Y is C—Z$^3$, or a pharmaceutically acceptable salt thereof.

8. The method of claim 7, wherein Z$^3$ is hydrogen, C$_{1-9}$ alkyl, C$_{3-15}$ cycloalkyl, heterocyclyl, aryl, or heteroaryl;
wherein said C$_{1-9}$ alkyl, C$_{3-15}$ cycloalkyl, aryl, or heterocyclyl, may be optionally substituted with one to four substituents independently selected from the group consisting of cyano, halo, —O—R$^{12}$, —C(O)—R$^{12}$, —OC(O)—R$^{12}$, —C(O)O—R$^{12}$, —C(O)—N(R$^{13}$)(R$^{14}$), —N(R$^{13}$)(R$^{14}$), —N(R$^{13}$)$_2$(R$^{14}$)$^+$, —S(O)$_2$—R$^{12}$, —Si(R$^{12}$)$_3$, C$_{1-9}$ alkyl, C$_{1-9}$ haloalkyl, C$_{3-15}$ cycloalkyl, aryl, heterocyclyl, and heteroaryl; and
wherein said C$_{1-9}$ alkyl, C$_{3-15}$ cycloalkyl, heterocyclyl, or aryl may be optionally substituted with one to three substituents independently selected from the group consisting of halo, —O(C$_{1-9}$ alkyl), —C(O)N(C$_{1-9}$ alkyl)$_2$, C$_{1-9}$ alkyl, and heterocyclyl, or a pharmaceutically acceptable salt thereof.

9. The method of claim 7, wherein Z$^3$ is hydrogen or C$_{1-9}$ alkyl;
wherein said C$_{1-9}$ alkyl may be optionally substituted with one to four substituents independently selected from the group consisting of cyano, halo, —O—R$^{12}$, —C(O)—R$^{12}$, —OC(O)—R$^{12}$, —C(O)O—R$^{12}$, —C(O)—N(R$^{13}$)(R$^{14}$), —N(R$^{13}$)(R$^{14}$), —N(R$^{13}$)$_2$(R$^{14}$)$^+$, —S(O)$_2$—R$^{12}$, —Si(R$^{12}$)$_3$, C$_{1-9}$ haloalkyl, C$_{3-15}$ cycloalkyl, aryl, heterocyclyl, and heteroaryl; and
wherein said C$_{3-15}$ cycloalkyl, aryl, heterocyclyl, or heteroaryl may be optionally substituted with one to three substituents independently selected from the group consisting of halo, —O(C$_{1-9}$ alkyl), —C(O)N(C$_{1-9}$ alkyl)$_2$, C$_{1-9}$ alkyl, and heterocyclyl, or a pharmaceutically acceptable salt thereof.

10. The method of claim 7, wherein Z$^3$ is hydrogen or C$_{1-9}$ alkyl optionally substituted with one to four substituents independently selected from the group consisting of cyano, halo, —O—R$^{12}$, —C(O)O—R$^{12}$, —OC(O)—R$^{12}$, —N(R$^{13}$)(R$^{14}$), —N(R$^{13}$)$_2$(R$^{14}$)$^+$, C$_{1-9}$ haloalkyl, heterocyclyl, and heteroaryl, or a pharmaceutically acceptable salt thereof.

11. The method of claim 7, wherein Z$^3$ is C$_{3-15}$ cycloalkyl, heterocyclyl, aryl, or heteroaryl;
wherein said C$_{1-9}$ alkyl, C$_{3-15}$ cycloalkyl, aryl, or heterocyclyl, may be optionally substituted with one to four substituents independently selected from the group consisting of cyano, halo, —O—R$^{12}$, —C(O)—R$^{12}$, —OC(O)—R$^{12}$, —C(O)O—R$^{12}$, —C(O)—N(R$^{13}$)(R$^{14}$), —N(R$^{13}$)(R$^{14}$), —N(R$^{13}$)$_2$(R$^{14}$)$^+$, —S(O)$_2$—R$^{12}$, —Si(R$^{12}$)$_3$, C$_{1-9}$ alkyl, C$_{1-9}$ haloalkyl, C$_{3-15}$ cycloalkyl, aryl, heterocyclyl, and heteroaryl; and
wherein said C$_{1-9}$ alkyl, C$_{3-15}$ cycloalkyl, heterocyclyl, or aryl may be optionally substituted with one to three substituents independently selected from the group consisting of halo, —O(C$_{1-9}$ alkyl), —C(O)N(C$_{1-9}$ alkyl)$_2$, C$_{1-9}$ alkyl, and heterocyclyl, or a pharmaceutically acceptable salt thereof.

12. The method of claim 7, wherein Z$^3$ is C$_{3-15}$ cycloalkyl optionally substituted with one to four substituents independently selected from the group consisting of cyano, halo, —O—R$^{12}$, —C(O)O—R$^{12}$, —OC(O)—R$^{12}$, —N(R$^{13}$)(R$^{14}$), —N(R$^{13}$)$_2$(R$^{14}$)$^+$, C$_{1-9}$ alkyl, C$_{1-9}$ haloalkyl, heterocyclyl, and heteroaryl, or a pharmaceutically acceptable salt thereof.

13. The method of claim 1 comprising administering an effective amount of a compound of Formula IVA:

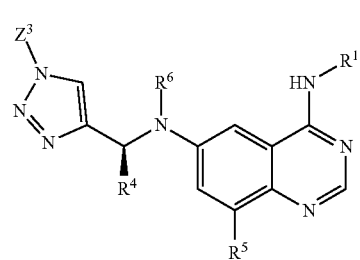

IVA wherein Z$^3$, R$^1$, R$^4$, R$^5$ and R$^6$ are as defined in claim 1, or a pharmaceutically acceptable salt thereof.

14. The method of claim 13, wherein:

$Z^3$ is hydrogen, $C_{1-9}$ alkyl, $C_{3-15}$ cycloalkyl, heterocyclyl, aryl, or heteroaryl;

wherein said $C_{1-9}$ alkyl, $C_{3-5}$ cycloalkyl, heterocyclyl, aryl, or heteroaryl may be optionally substituted with one to four substituents independently selected from the group consisting of cyano, halo, —O—$R^{12}$, —C(O)—$R^{12}$, —OC(O)—$R^{12}$, —C(O)O—$R^{12}$, —C(O)—N($R^{13}$)($R^{14}$), —N($R^{13}$)($R^{14}$), —N($R^{13}$)$_2$($R^{14}$)$^+$, —S(O)$_2$—$R^{12}$, —Si($R^{12}$)$_3$, $C_{1-9}$ alkyl, $C_{1-9}$ haloalkyl, $C_{3-15}$ cycloalkyl, aryl, heterocyclyl, and heteroaryl;

wherein said $C_{1-9}$ alkyl, $C_{3-5}$ cycloalkyl, aryl, heterocyclyl, and heteroaryl may be optionally substituted with one to three substituents independently selected from the group consisting of halo, —O($C_{1-9}$ alkyl), —C(O)—N($C_{1-9}$ alkyl)$_2$, $C_{1-9}$ alkyl, and heterocyclyl;

$R^1$ is $C_{1-9}$ alkyl;

wherein said $C_{1-9}$ alkyl may be optionally substituted with one to three substituents independently selected from the group consisting of cyano, halo, —O—$R^{12}$, —N($R^{13}$)($R^{14}$), —N($R^{12}$)C(O)O—$R^{12}$, —S(O)$_2$—$R^{12}$, —Si($R^{12}$)$_3$, $C_{1-9}$ alkyl, $C_{3-15}$ cycloalkyl, heterocyclyl, aryl, and heteroaryl;

wherein said $C_{1-9}$ alkyl, $C_{3-5}$ cycloalkyl, aryl, or heteroaryl may be optionally substituted with one to three substituents independently selected from the group consisting of cyano, halo, —O—$R^{12}$, —N($R^{13}$)($R^{14}$), $C_{1-9}$ alkyl, $C_{3-5}$ cycloalkyl, and aryl;

$R^4$ is aryl, heterocyclyl, or heteroaryl;

wherein said aryl, heterocyclyl, or heteroaryl is optionally substituted with one to three substituents independently selected from the group consisting of cyano, halo, —O—$R^{12}$, —C(O)—$R^{12}$, —C(O)O—$R^{12}$, —S(O)$_2$—$R^{12}$, —N($R^{12}$)C(O)—$R^{12}$, —N($R^{12}$)S(O)$_2$$R^{12}$, —C(O)N($R^{13}$)($R^{14}$), —N($R^{13}$)($R^{14}$), $C_{1-9}$ alkyl, heterocyclyl, aryl, and heteroaryl;

wherein said $C_{1-9}$ alkyl, or heteroaryl may be optionally substituted with one to three substituents independently selected from the group consisting of halo, —O—$R^{12}$, —N($R^{13}$)($R^{14}$), $C_{1-9}$ alkyl, and heterocyclyl;

$R^5$ is cyano, halo, —O—$R^7$, —C(O)$R^7$, —N($R^8$)C(O)($R^7$), —C(O)N($R^8$)($R^9$), $C_{1-9}$ alkyl, $C_{2-6}$ alkynyl, $C_{3-15}$ cycloalkyl, aryl, or heteroaryl;

wherein said $C_{1-9}$ alkyl, aryl, or heteroaryl may be optionally substituted with one to three substituents independently selected from the group consisting of halo, —O—$R^{12}$, and $C_{1-9}$ alkyl;

each $R^7$ is independently hydrogen, $C_{1-9}$ alkyl, $C_{3-15}$ cycloalkyl, heterocyclyl, or aryl;

wherein said $C_{1-9}$ alkyl, $C_{3-15}$ cycloalkyl, heterocyclyl, or aryl may be optionally substituted with one to three substituents independently selected from the group consisting of halo, —O—$R^{12}$, —N($R^{13}$)($R^{14}$), $C_{1-9}$ alkyl, aryl, and heteroaryl;

each $R^{12}$ is independently hydrogen, $C_{1-9}$ alkyl, $C_{3-15}$ cycloalkyl, heterocyclyl, or aryl;

wherein said $C_{1-9}$ alkyl, $C_{3-15}$ cycloalkyl, heterocyclyl, or aryl may be optionally substituted with one to three substituents independently selected from the group consisting of halo, hydroxy, —O($C_{1-9}$ alkyl), —N($C_{1-9}$ alkyl)$_2$, $C_{1-9}$ alkyl, aryl, and heteroaryl; and each $R^{13}$ and $R^{14}$ are independently hydrogen, $C_{1-9}$ alkyl, $C_{3-15}$ cycloalkyl, heterocyclyl, or aryl;

wherein said $C_{1-9}$ alkyl, $C_{3-15}$ cycloalkyl, heterocyclyl, or aryl may be optionally substituted with one to three substituents independently selected from the group consisting of halo, hydroxy, —O($C_{1-9}$ alkyl), —N($C_{1-9}$ alkyl)$_2$, $C_{1-9}$ alkyl, aryl, and heteroaryl, or a pharmaceutically acceptable salt thereof.

15. The method of claim 3, wherein $Z^3$ is cyclopropyl optionally substituted with $C_{1-9}$ haloalkyl, or a pharmaceutically acceptable salt thereof.

16. The method of claim 3, wherein $Z^3$ is cyclopropyl, 1-(fluoromethyl)cyclopropyl, 1-(difluoromethyl)cyclopropyl, 1-(trifluoromethyl)cyclopropyl, 1-cyanocyclopropyl, bicyclo[1.1.1]pentan-1-yl, or carboxymethyl, or a pharmaceutically acceptable salt thereof.

17. The method of claim 1, wherein R1 is $C_{1-9}$ alkyl optionally substituted with one to four substituents independently selected the group consisting of cyano, aryl and heterocyclyl, or a pharmaceutically acceptable salt thereof.

18. The method of claim 1, wherein R1 is $C_{1-9}$ alkyl optionally substituted with one to two substituents independently selected the group consisting of cyano, phenyl and tetrahydro-2H-pyran, or a pharmaceutically acceptable salt thereof.

19. The method of claim 1, wherein $R^1$ is 2,2-dimethylpropyl, (4-methyltetrahydro-2H-pyran-4-yl)methyl, or 3-cyano-1-phenylpropyl, or a pharmaceutically acceptable salt thereof.

20. The method of claim 1, wherein $R^4$ is aryl or heteroaryl, wherein said aryl or heteroaryl may be optionally substituted with one to three substituents independently selected from the group consisting of cyano, halo and $C_{1-9}$ alkyl, or a pharmaceutically acceptable salt thereof.

* * * * *